(12) United States Patent
Rafiee et al.

(10) Patent No.: US 11,950,827 B2
(45) Date of Patent: Apr. 9, 2024

(54) TISSUE EXCISION, CUTTING, AND REMOVAL SYSTEMS AND METHODS

(71) Applicant: Transmural Systems LLC, Andover, MA (US)

(72) Inventors: Nasser Rafiee, Andover, MA (US); Stuart Macdonald, Andover, MA (US); Rany Busold, Andover, MA (US); Alexis Balcom, Andover, MA (US); Morgan House, Andover, MA (US)

(73) Assignee: Transmural Systems LLC, Andover, MA (US)

( * ) Notice: Subject to any disclaimer, the term of this patent is extended or adjusted under 35 U.S.C. 154(b) by 361 days.

(21) Appl. No.: 17/086,431

(22) Filed: Nov. 1, 2020

(65) Prior Publication Data

US 2021/0137579 A1    May 13, 2021

Related U.S. Application Data

(63) Continuation of application No. PCT/US2020/055160, filed on Oct. 9, 2020.
(Continued)

(51) Int. Cl.
*A61B 18/14* (2006.01)
*A61B 18/08* (2006.01)
(Continued)

(52) U.S. Cl.
CPC ........ *A61B 18/082* (2013.01); *A61B 18/1442* (2013.01); *A61B 90/39* (2016.02);
(Continued)

(58) Field of Classification Search
CPC . A61B 17/22; A61B 17/221; A61B 17/32056; A61B 18/082; A61B 18/1442;
(Continued)

(56) References Cited

U.S. PATENT DOCUMENTS 5,417,697 A * 5/1995 Wilk ............... A61B 18/10
606/115
5,599,300 A    2/1997 Weaver et al.
(Continued)

FOREIGN PATENT DOCUMENTS

DE     10037660 A1    2/2002
DE    202010016945 U1    3/2011
(Continued)

OTHER PUBLICATIONS

Written Opinion of the International Searching Authority for International Application No. PCT/US2018/048177 dated Nov. 19, 2018.
(Continued)

*Primary Examiner* — Michael F Peffley
(74) *Attorney, Agent, or Firm* — DeWitt LLP; Brian R. Pollack, Esq.

(57) ABSTRACT

The disclosure provides various embodiments of catheters that can be used for various procedures. Embodiments of methods are also provided that can be performed with catheters in accordance with the present disclosure.

14 Claims, 72 Drawing Sheets

Related U.S. Application Data

(60) Provisional application No. 63/077,579, filed on Sep. 12, 2020, provisional application No. 63/052,450, filed on Jul. 15, 2020, provisional application No. 63/047,995, filed on Jul. 3, 2020, provisional application No. 62/939,877, filed on Nov. 25, 2019, provisional application No. 62/939,907, filed on Nov. 25, 2019, provisional application No. 62/924,358, filed on Oct. 22, 2019, provisional application No. 62/913,158, filed on Oct. 9, 2019, provisional application No. 62/913,150, filed on Oct. 9, 2019.

(51) Int. Cl.
*A61B 90/00* (2016.01)
*A61B 18/00* (2006.01)

(52) U.S. Cl.
CPC .............. *A61B 2018/00369* (2013.01); *A61B 2018/00577* (2013.01); *A61B 2018/141* (2013.01); *A61B 2018/1452* (2013.01); *A61B 2090/3966* (2016.02)

(58) Field of Classification Search
CPC ...... A61B 18/1492; A61B 2017/00353; A61B 2017/22044; A61B 2017/22097; A61B 2018/00267; A61B 2018/00369; A61B 2018/0041; A61B 2018/00577; A61B 2018/00601; A61B 2018/141; A61B 2018/1452; A61B 90/39; A61B 2090/3966
See application file for complete search history.

(56) References Cited

U.S. PATENT DOCUMENTS

| | | | |
|---|---|---|---|
| 5,759,187 A * | 6/1998 | Nakao | A61B 1/018 606/113 |
| 6,007,546 A * | 12/1999 | Snow | A61B 18/14 606/113 |
| 6,017,340 A | 1/2000 | Cassidy et al. | |
| 6,391,044 B1 * | 5/2002 | Yadav | A61F 2/013 606/200 |
| 6,517,551 B1 | 2/2003 | Driskill | |
| 6,533,782 B2 | 3/2003 | Howell et al. | |
| 6,582,425 B2 | 6/2003 | Simpson | |
| 6,695,836 B1 | 2/2004 | DeMello et al. | |
| 7,303,798 B2 | 12/2007 | Bavaro et al. | |
| 7,455,646 B2 | 11/2008 | Richardson et al. | |
| 7,653,438 B2 * | 1/2010 | Deem | A61N 5/00 607/44 |
| 8,827,948 B2 | 9/2014 | Romo et al. | |
| 9,282,993 B1 | 3/2016 | Cohen et al. | |
| 9,572,666 B2 | 2/2017 | Basude et al. | |
| 9,833,272 B2 | 12/2017 | Sweeney | |
| 9,980,716 B2 | 5/2018 | Harris et al. | |
| 10,143,481 B2 | 12/2018 | Golan | |
| 2003/0088195 A1 | 5/2003 | Vardi et al. | |
| 2004/0267161 A1 | 12/2004 | Osborne et al. | |
| 2008/0228209 A1 | 9/2008 | DeMello et al. | |
| 2012/0123328 A1 | 5/2012 | Williams | |
| 2014/0276605 A1 | 9/2014 | Tejani et al. | |
| 2017/0007277 A1 | 1/2017 | Drapeau et al. | |
| 2018/0008268 A1 | 1/2018 | Khairkhahan | |
| 2019/0175199 A1 | 6/2019 | Girdhar et al. | |
| 2019/0183571 A1 * | 6/2019 | De Marchena | A61B 18/02 |
| 2020/0383717 A1 | 12/2020 | Lederman et al. | |

FOREIGN PATENT DOCUMENTS

| | | |
|---|---|---|
| EP | 3175813 B1 | 1/2020 |
| RU | 2152757 C1 | 7/2000 |
| WO | 2019/040943 A1 | 2/2019 |
| WO | 2019164806 A1 | 8/2019 |
| WO | 2021007324 A1 | 1/2021 |
| WO | 2021072331 A1 | 4/2021 |
| WO | 2022066621 A1 | 3/2022 |

OTHER PUBLICATIONS

International Search Report for International Application No. PCT/US2018/048177 dated Dec. 20, 2018.

Khan et al., "Intentional Laceration of the Anterior Mitral Valve Leaflet to Prevent Left Ventricular Outflow Tract Obstruction During Transcatheter Mitral Valve Replacement", JACC: Cardiovascular Interventions vol. 9, No. 17, 2016.

Babaliaros et al., "Intentional Percutaneous Laceration of the Anterior Mitral Leaflet to Prevent Outflow Obstruction During Transcatheter Mitral Valve Replacement First-in-Human Experience", JACC: Cardiovascular Interventions vol. 10 , No. 8, 2017.

Lederman et al., "Preventing Coronary Obstruction During Transcatheter Aortic Valve Replacement From Computed Tomography to Basilica", JACC: Cardiovascular Interventions vol. 12 , No. 13. 2019, pp. 1197-1216.

Khan et al., "Predicting Left Ventricular Outflow Tract Obstruction Despite Anterior Mitral Leaflet Resection the "Skirt NeoLVOT"", JACC: Cardiovascular Interventions Sep. 2019, vol. 11 , No. 9, pp. 1356-1359.

Case, "Tip to Base LAMPOON to PRevent Left Ventricular Outflow Tract Obstruction in Valve in Valve Transcatheter Mitral Valve Replacement", JACC: Cardiovascular Interventions, May 2020, vol. 13, No. 9, pp. 1126-1128.

Greenbaum et al., "First-in-human transcatheter pledglet-assisted suture tricuspid annuloplasty for severe tricuspid insufficiency," Catheterization and Cardiovascular Interventions, May 2020, 5 pages.

Kamioka et al., "BI-SILICA During Transcatheter Aortic Valve Replacement for Noncalcific Aortic Insufficiency: Initial Human Experience", JACC: Cardiovascular Interventions, Nov., 2018, vol. 11, No. 21, pp. 2237-2239.

Kasel et al., "International Lampoon: First European experience with laceration of the anterior mitral valve leaflet prior to transseptal transcatheter mitral valve implantation", Eurointervention, Sep. 2018, col. 14, No. 7, pp. 746-749.

Khan et al., "The Basilica Trial: Prospective Multicenter Investigation of Intentional Leaflet Laceration to Prevent TAVR Coronary Obstruction", JACC: Cardiovascular Interventions, 2019, vol. 12, No. 13, pp. 1240-1252.

Khan et al., "Transcatheter Mitral Valve Replacement after Transcatheter Electrosurgical Laceration of Alfieri stitch (Elastic): First in human report," JACC: Cardiovascular Interventions, Apr. 2018, vol. 11, No. 8, pp. 1808-1811.

Khan et al., "Transcatheter Electrosurgery: JACC State of the art review," Journal of the American College of Cardiology, Mar. 2020, vol. 75, No. 12, pp. 1455-1470.

Khan et al., "Anterior Leaflet Laceration to Prevent Ventricular Outflow Tract Obstruction During Transcatheter Mitral Valve Replacement," Journal of the American College of Cardiology, May 2019, vol. 73, No. 20, pp. 2521-2534.

Khan et al., "Rescue LAMPOON to Treat Transcatheter Mitral Valve Replacement—Associated Left Ventricular Outflow Tract Obstruction", JACC: Cardiovascular Interventions, Jul. 2019, vol. 12, No. 13, pp. 1283-1284.

Lisko et al., "Pachyderm Shape guiding catheters to simplify Basilica leaflet traversal," Cardiovsacular Revascularization Medicine, Sep. 2019, vol. 20, No. 9, pp. 782-785.

Lisko et al., "Electrosurgical detachment of Mitraclips from the anterior mitral leaflet prior to transcatheter mitral valve implantation," JACC: Cardiovascular Interventions, Oct. 2020, vol. 13, No. 20, pp. 2361-2370.

Khan et al., "LAMPOON to facilitate tendyn Anterior Leaflet Laceration to Prevent Ventricular Outflow Tract Obstruction During Transcatehter Mitral Valve Replacement," Journal of the American College of Cardiology, May 2019, vol. 73, No. 20, pp. 2521-2534.

(56) References Cited

OTHER PUBLICATIONS

Written Opinion and International Search Report dated Mar. 1, 2021 for International Patent Application No. PCT/US2020/055160.

\* cited by examiner

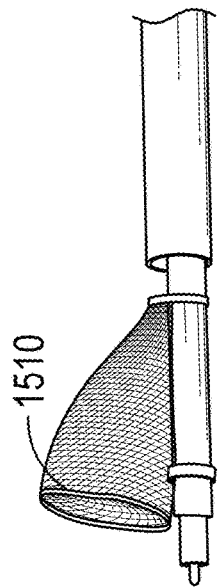
FIG. 10B
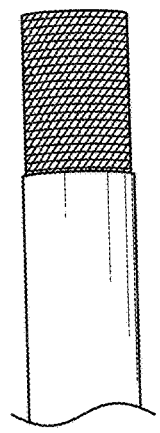
FIG. 10D
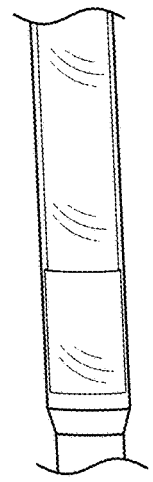
FIG. 10F
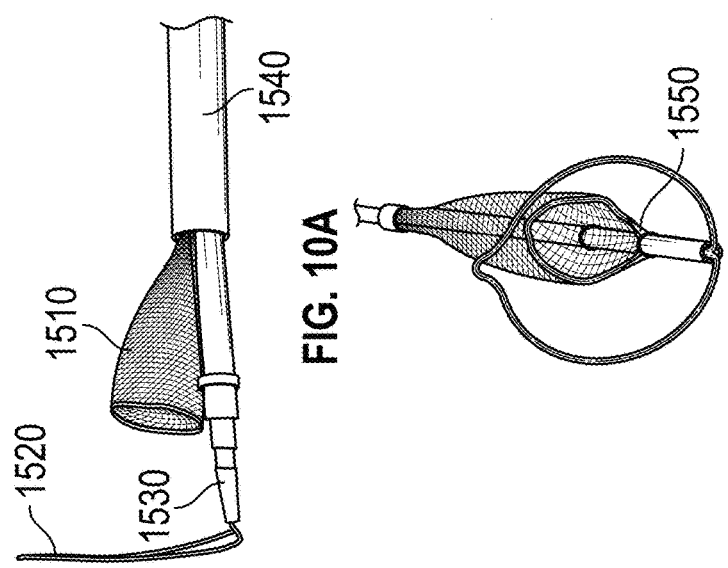
FIG. 10A
FIG. 10C
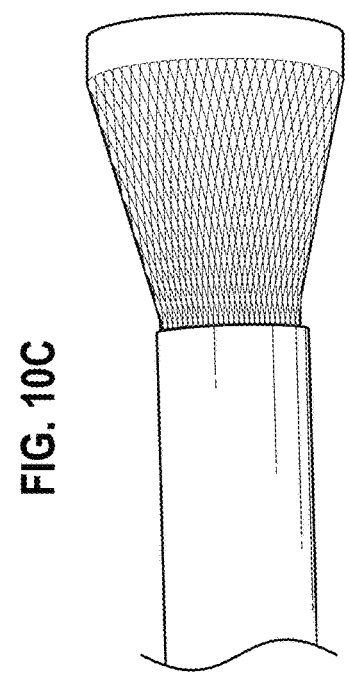
FIG. 10E

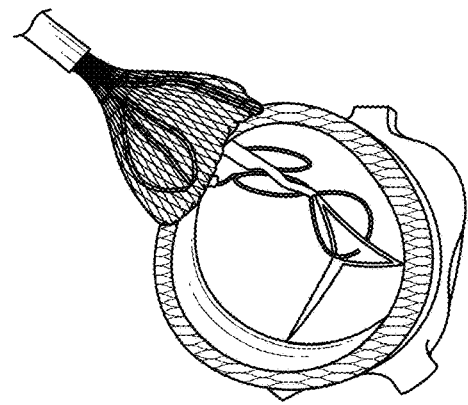
FIG. 21A
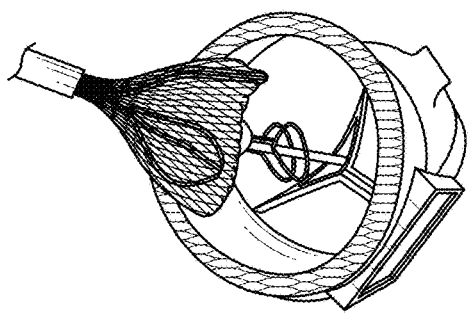
FIG. 21B
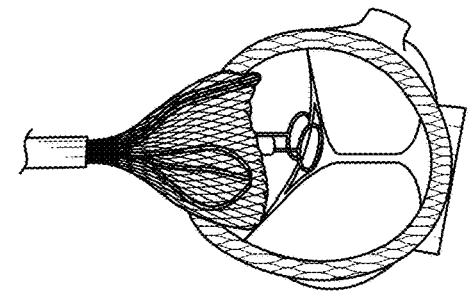
FIG. 21C
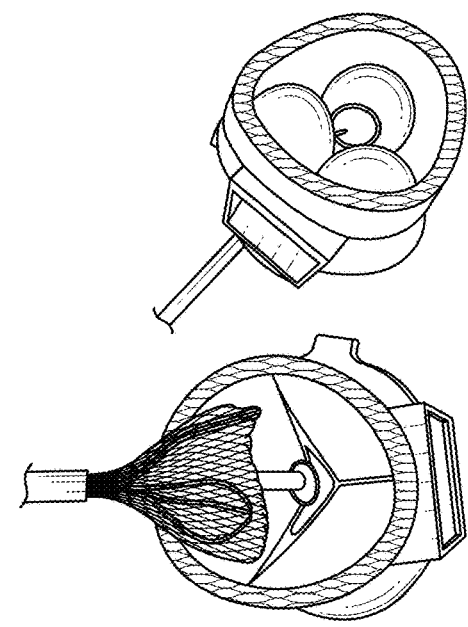
FIG. 21D
FIG. 21E
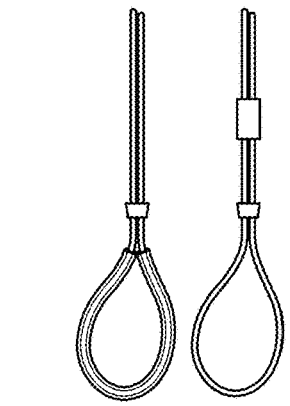
FIG. 22A
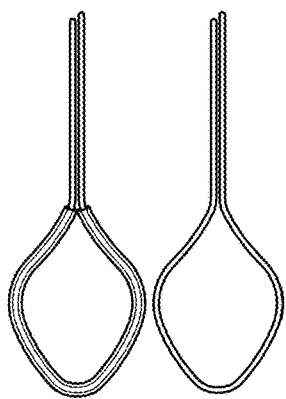
FIG. 22B
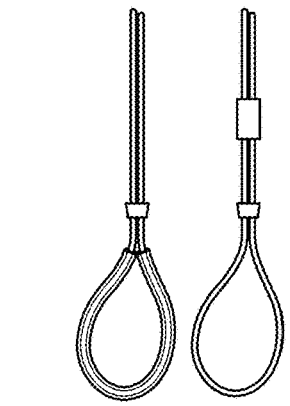
FIG. 22C

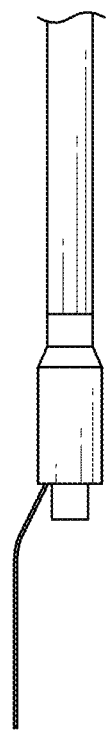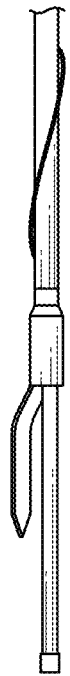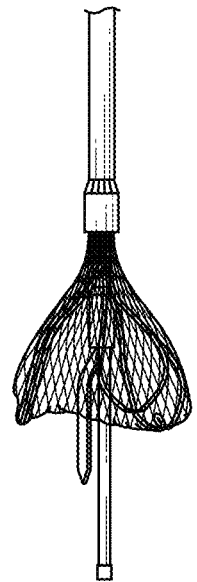

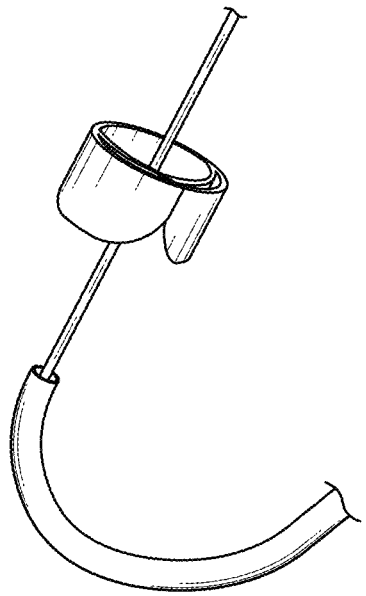
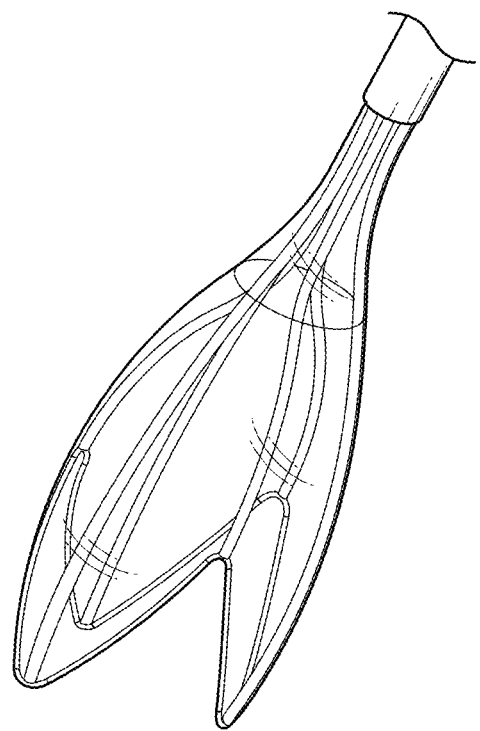
FIG. 39　　　　　　FIG. 40
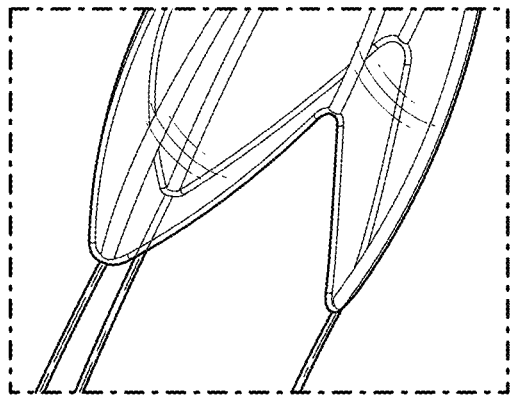
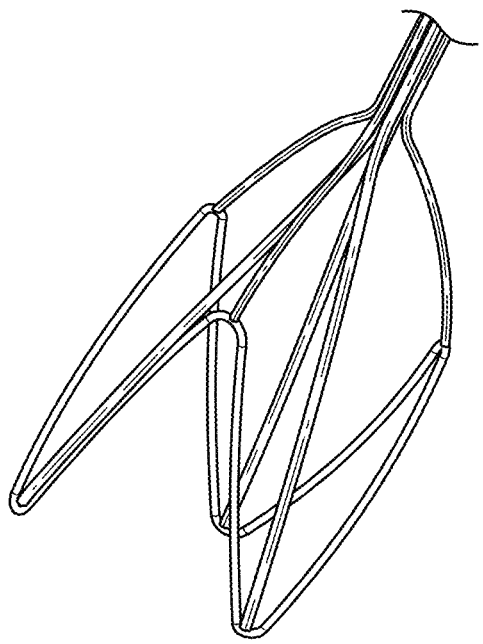
FIG. 41　　　　　　FIG. 42

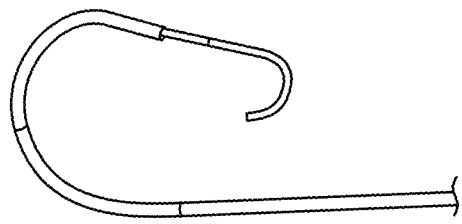
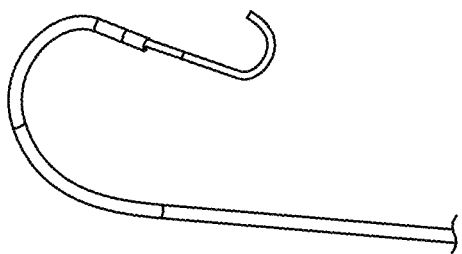
FIG. 74B
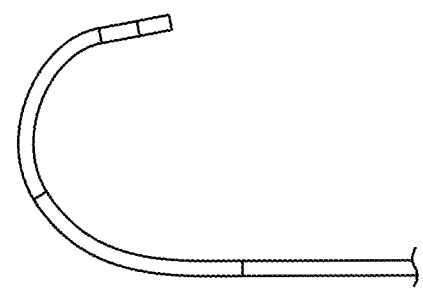
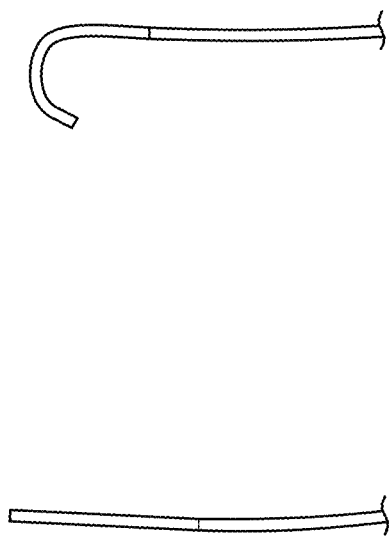
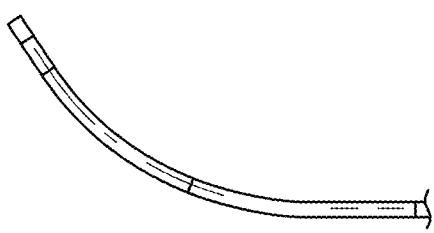
FIG. 74A

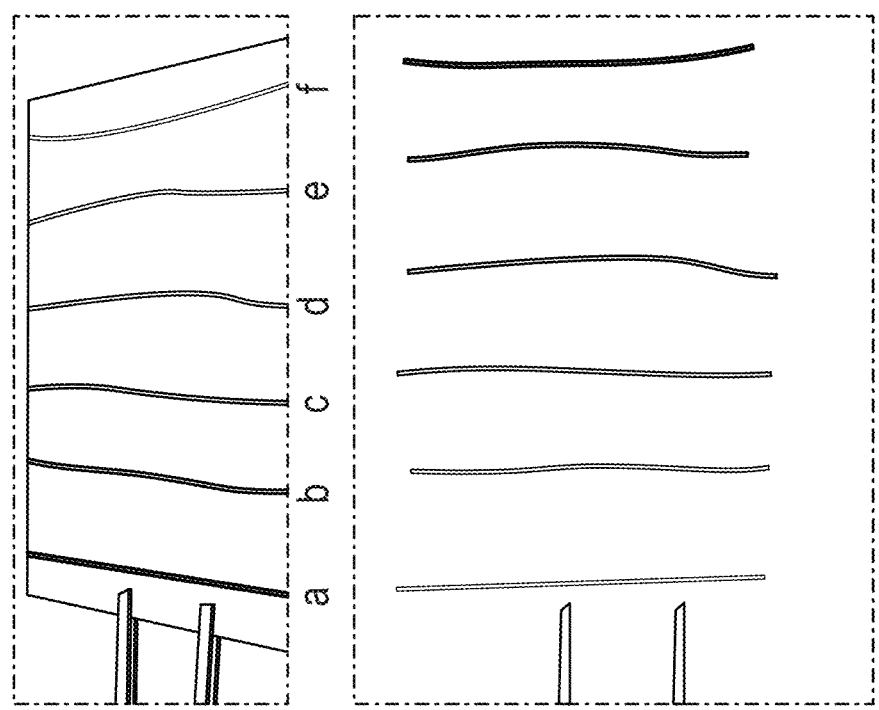
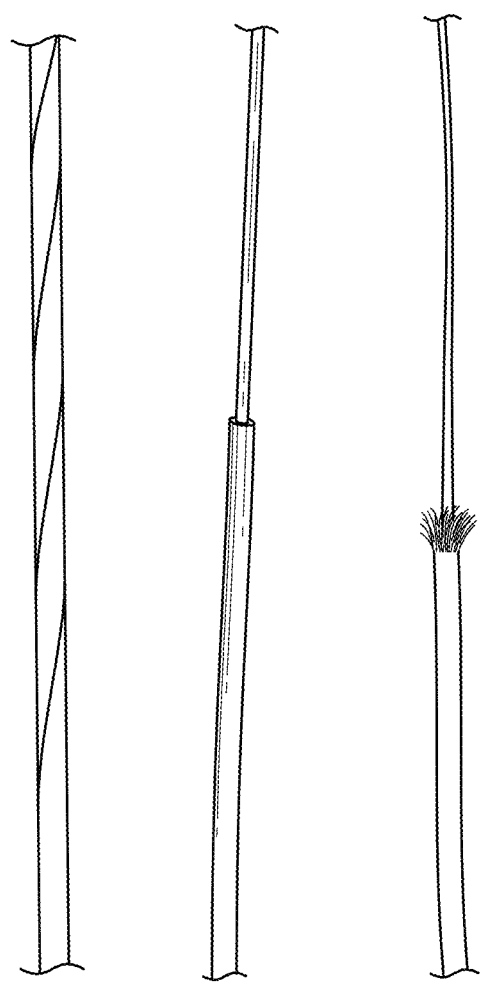
FIG. 78

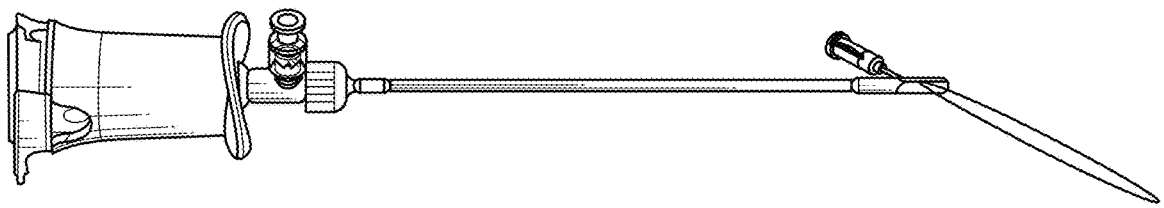
FIG. 82
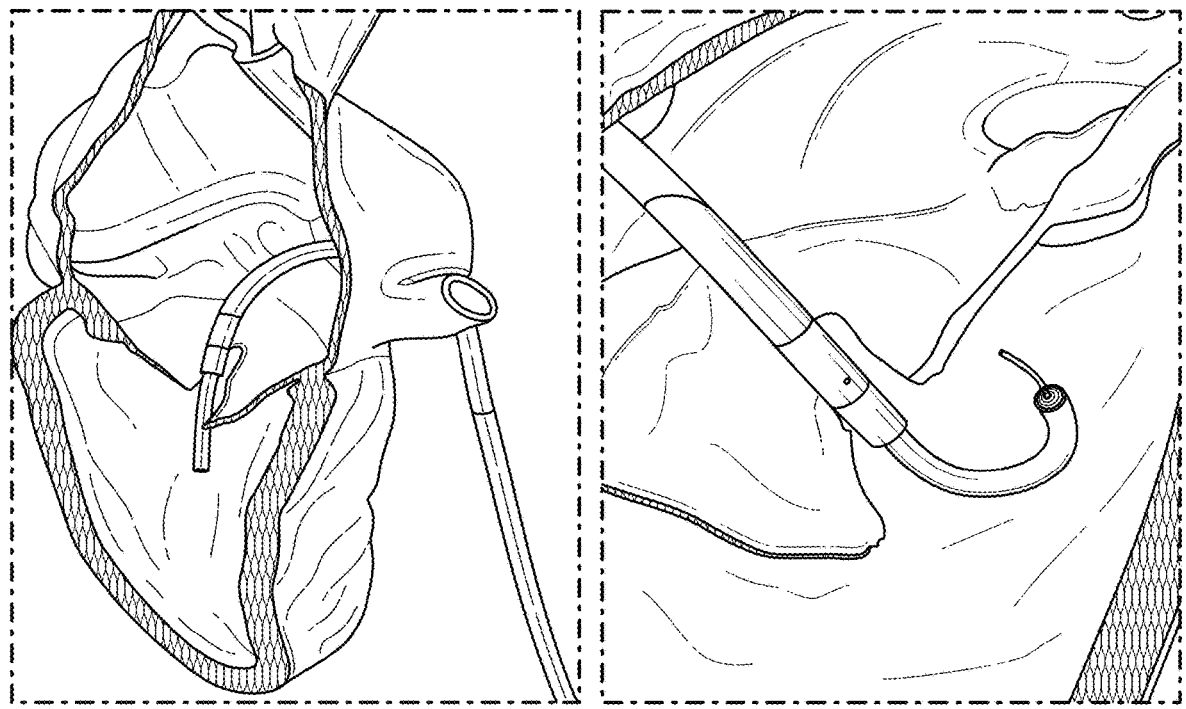
FIG. 83A
FIG. 83B

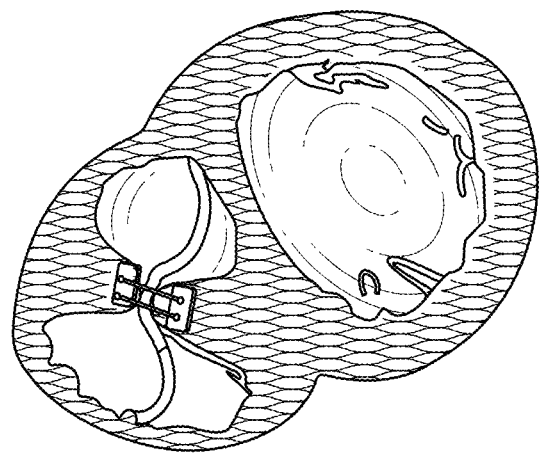
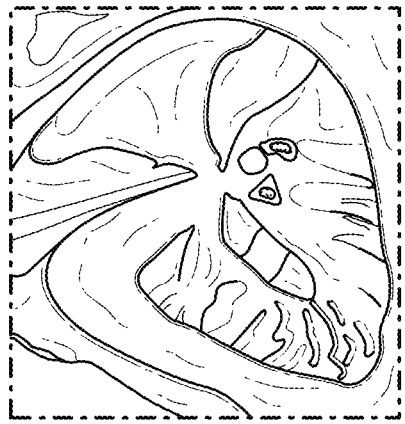
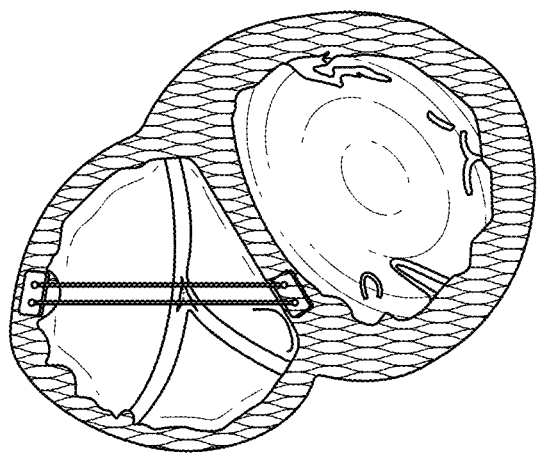
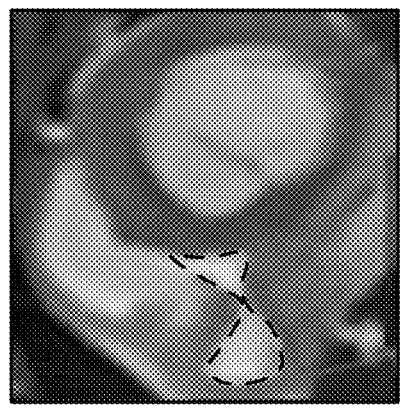
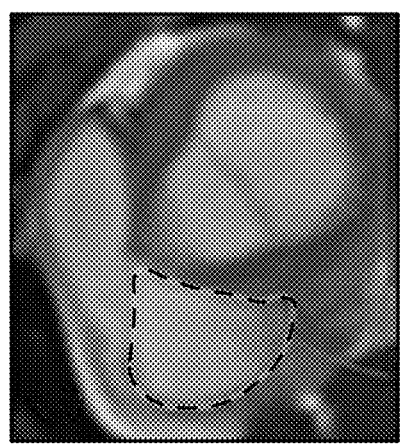
FIG. 89

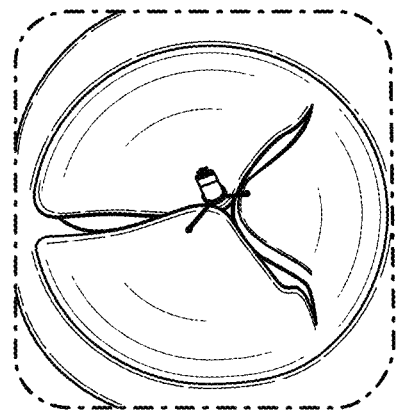
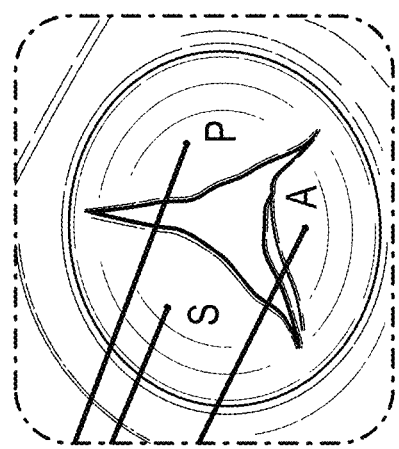
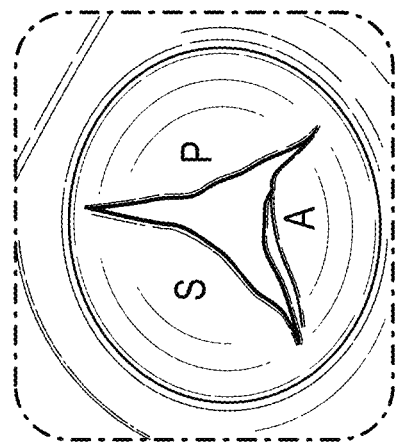
FIG. 94

TISSUE EXCISION, CUTTING, AND REMOVAL SYSTEMS AND METHODS

CROSS-REFERENCE TO RELATED APPLICATION

The present patent application is a continuation of and claims the benefit of priority to International Application No. PCT/US2020/55160, filed Oct. 9, 2020, which in turn claims the benefit of priority to, U.S. Patent Application No. 62/913,150, filed Oct. 9, 2019, U.S. Patent Application No. 62/913,158, filed Oct. 9, 2019, U.S. Patent Application No. 62/924,358, filed Oct. 22, 2019, U.S. Patent Application No. 62/939,907, filed Nov. 25, 2019, U.S. Patent Application No. 62/939,877, filed Nov. 25, 2019, U.S. Patent Application No. 63/047,995, filed Jul. 3, 2020, U.S. Patent Application No. 63/052,450, filed Jul. 15, 2020, U.S. Patent Application No. 63/077,579, filed Sep. 12, 2020. This patent application is also related to U.S. patent application Ser. No. 16/563,925, filed Sep. 8, 2019, which in turn claims the benefit of U.S. Patent Application Ser. No. 62/728,413, filed Sep. 7, 2018, and International Patent Application No. PCT/US2018/48177, filed Aug. 27, 2018, which in turn claims the benefit of priority to U.S. Provisional Application Ser. No. 62/550,347, filed Aug. 25, 2017, U.S. Provisional Application Ser. No. 62/567,203, filed Oct. 2, 2017, U.S. Provisional Patent Application Ser. No. 62/663,518, filed Apr. 27, 2018, U.S. Provisional Application Ser. No. 62/688,378, filed Jun. 21, 2018, and U.S. Provisional Patent Application Ser. No. 62/712,194, filed Jul. 30, 2018. Each of the foregoing patent applications is incorporated by reference herein in its entirety for any purpose whatsoever.

BACKGROUND

The disclosure relates generally to medical treatment devices and techniques, and, in some aspects, to methods and devices for diagnosis and treatment of cardiac valves. The present disclosure provides improvements over the state of the art.

SUMMARY OF THE DISCLOSURE

The present disclosure provides various systems and methods for removing clips, cysts and other structures from valve leaflets. The disclosure further provides systems for modifying or removing luminal valve leaflets. The disclosure also provides other innovations, as set forth below.

BRIEF DESCRIPTION OF THE FIGURES

FIGS. 10A-18G illustrate aspects of a first clip or cyst removal system in accordance with the disclosure.

FIGS. 19A-26D illustrate aspects of a leaflet removal system in accordance with the disclosure.

FIGS. 27-57 illustrate aspects of methods and systems to remove aortic valve leaflets in accordance with the disclosure.

FIGS. 58-94 illustrate aspects of methods and systems for coupling valve leaflets in accordance with the disclosure.

DETAILED DESCRIPTION

The present disclosure provides a variety of methods and systems. In some implementations, the disclosure provides systems and methods to remove ether structures that are no longer desired in the anatomy. For example, if an Alfieri stitch, or a clip, is used to attach a portion of two cardiac leaflets to each other, the disclosed embodiments can be used to cut through one or both of the leaflets to free them from each other, and to also prepare the site, if desired, for a replacement valve, such as by forming one or more additional cuts in each native leaflet, and/or removing a portion of, or substantially the entirety of, or the entirety of, one or more of the native leaflets. If desired, all the leaflets can be removed, and any structures attached thereto (e.g., chordae) can also be cut and/or removed. In some implementations, a suture or clip (e.g., a MitralClip) can be removed from a patient's mitral valve, after which further therapeutic steps can be performed including repair of the valve leaflets, reshaping of the valve leaflets, removing all or a portion of one or all leaflets, or cutting the leaflets and any chordae out of the way, as desired, to make room for a replacement valve.

Similar procedures for resecting or cutting tissue anywhere in the body can be used by utilizing devices and methods in accordance with the present disclosure. Such procedures can be used for cutting valve leaflets, for example, in any of the cardiac valves, any valves in veins, such as the IVC, or for cutting any other anatomical structures in the body.

Any suitable power level and duty cycle can be used in accordance with the disclosed embodiments when electrified tissue cutting techniques are used. For example, continuous duty cycle (cutting) radiofrequency ("RF") energy can be used, for example, at a power level between about 50 and 100 Watts, or any increment therebetween of about one watt. The cuts can be made by applying power for between about one half of a second and about five seconds, or any increment therebetween of about one tenth of a second.

Figure 1:
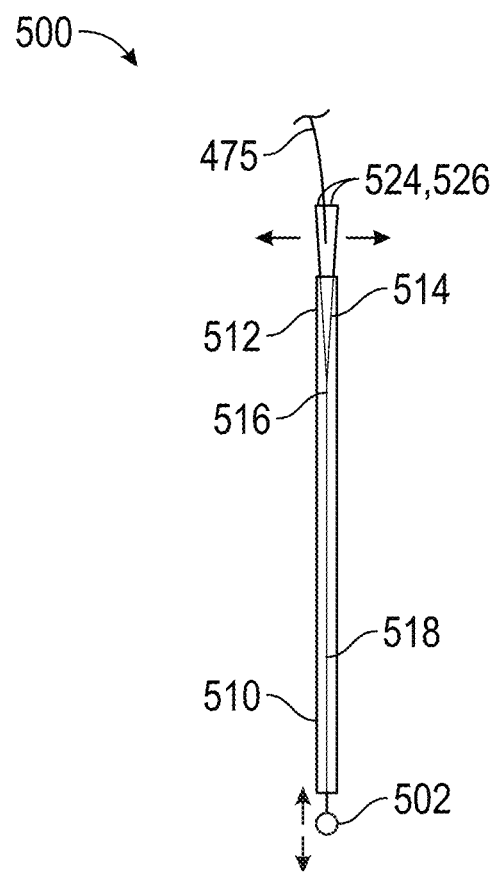
FIG. 1 presents a further embodiment of a grasping catheter in accordance with the present disclosure.

FIG. 1 presents an alternative embodiment of a grasping catheter 500 that can be used in place of a pair of catheters simply for grasping the edge of a leaflet 475. The catheter 500 includes a tubular outer body 510 having a proximal end, a distal end and a longitudinal passage therethrough. An internal slidable gripping mechanism is slidably disposed within the lumen of outer body 510 that includes a proximal actuator or handle 502 that is connected to an elongate inner body 518 that separates at a bifurcation 516 into a first arm 512 and a second arm 514, that in turn terminate in inwardly pointed gripping ends 524, 526. Arms 512, 514 are biased away from each other, and can be urged together by withdrawing the arms and accompanying tips toward the distal end of the tubular member 510. Accordingly, by controlling the relative placement of the inner mechanism and outer tube, the jaws formed by arms 512, 514 and gripping ends 524, 526 can be opened and closed. Catheter 500 can be used as a sub-catheter in any embodiment herein.

The disclosure also provides a robotic manipulator having a proximal end and a distal end that includes an elongate tubular arm having a proximal end, a distal end, and defining at least one elongate passage therethrough, the elongate tubular arm defining a longitudinal axis along its length. The manipulator further includes a first elongate inner body having a proximal end and a distal end that is slidably disposed within the at least one elongate passage of the elongate tubular arm, the distal end of the first inner elongate body being biased (or otherwise configured, such as pre-forming and/or steering wire) to curl away from the longitudinal axis in a proximal direction when the first elongate inner body is advanced distally with respect to the arm. The manipulator can further include a second elongate inner body having a proximal end and a distal end that is slidably disposed within the at least one elongate passage of the elongate tubular arm that can be slidably disposed with respect to the first inner body. The distal end of the second inner elongate body can be biased to curl away from the longitudinal axis toward the deployed proximally oriented distal end of the first elongate inner body when the second elongate inner body is advanced distally with respect to the arm.

At least one of the elongate tubular arm, first elongate inner body or second elongate inner body can be connected to an axial actuator, wherein the actuator is configured to advance the component to which it is connected along a direction parallel to the longitudinal axis. Moreover, at least one of the elongate tubular arm first elongate inner body or second elongate inner body can be connected to a rotational actuator, wherein the rotational actuator is configured to rotate one or more of the elongate tubular arms, first elongate inner body and second elongate inner body.

At least one of the first elongate inner body and second elongate inner body can include an end effector attached thereto configured to perform at least one of a cutting, grasping, irrigating, evacuating, viewing or suctioning function. If desired, the end effector can include one or more of an electrosurgical device, a blade, and an ultrasonic transducer.

The disclosure also provides implementations of a laparoscopic, urinary, gynecological, neurological, or orthopedic surgical procedure utilizing the catheters or robotic manipulators disclosed herein. The disclosed catheters/manipulators can also be used in any suitable minimally invasive procedure, or a percutaneous procedure.

For example, the percutaneous procedure can include utilizing one or more of the disclosed devices to access a patient's sinus passages. The devices can be used, for example, to remove one or more polyps, and can even be used to breach a thin bony layer within the sinuses to access the cranial cavity to perform a procedure inside the cranial cavity.

In other embodiments, the percutaneous procedures disclosed herein can include an ablation procedure, such as within the heart of a patient or elsewhere, as well as a cryoablation procedure.

Figure 2:
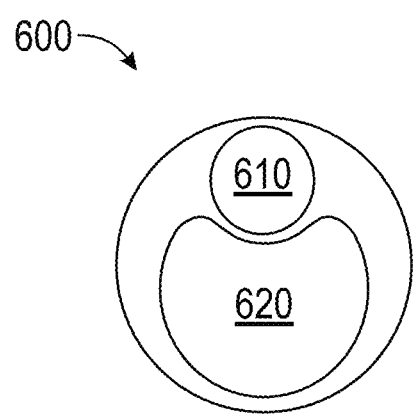
FIG. 2 illustrates a cross sectional view of an extruded main body portion of an illustrative catheter in accordance with the disclosure.

In further accordance with the present disclosure, FIG. 2 illustrates a cross sectional view of an extruded main body portion 600 of a further embodiment of a catheter. The body includes an extrusion defining two offset channels 610, 620. A first channel 610 is illustrated as having a generally circular cross-section, and the second channel 620 that is parallel thereto is illustrated as having a cross-section that is circular with a scalloped portion removed in order to accommodate the channel with the circular cross section. The main body 600 can be made from any suitable polymeric material, such as those set forth herein. The main body can be formed from a multilayer polymeric extrusion with one or more reinforcement (e.g. layers of braiding) formed thereon or therein. The main body can be coated with any suitable coating or material to enhance its lubricity, as desired.

Figure 3A:
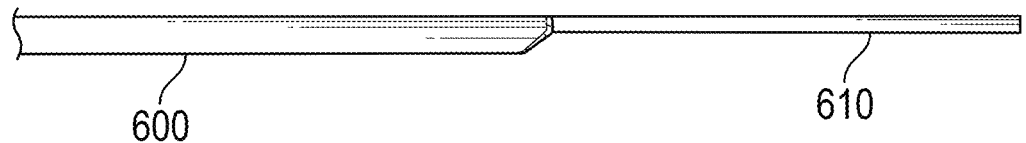
FIGS. 3A-3D present various embodiments of a dual lumen catheter in accordance with the present disclosure.
Figure 3B:
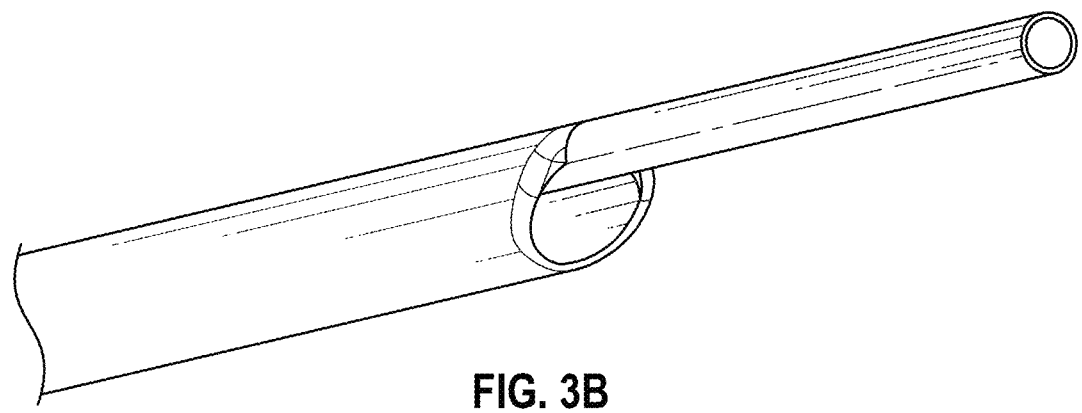

FIG. 3A presents a side view of the illustrative catheter of FIG. 2 including the main shaft 600 described above, provided with at least one braided layer. The catheter further includes a distal tubular segment extending distally from main shaft 600 that defines therein lumen 610 that is radially co-located with the first channel of the main body. For example, the distal tubular segment can be an extruded tube that extends the full length along the inside of the main body to a proximal end of the catheter. The distal tubular segment may similarly be braided if desired, may be pre-curved as described elsewhere herein and/or can be deflectable, for example, by providing a pull wire within the lumen of the distal segment, or within a co-extruded lumen of the distal segment (not specifically illustrated). A distal end of the pull wire (not shown) can be attached to a collar embedded within or on the distal tubular segment, as desired. As illustrated in FIG. 3B, the distal tubular segment and its associated channel that it surrounds can be used to act as a guidewire lumen, permitting the catheter to be used as an over the wire catheter, or for delivering a lower profile catheter therethrough, such as a snare catheter, as set forth in further detail below.

Figure 3C:
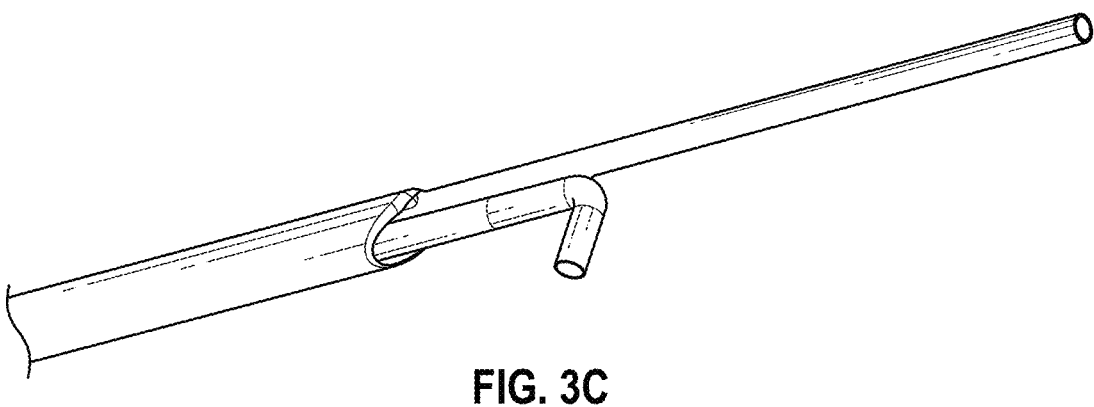
Figure 3D:
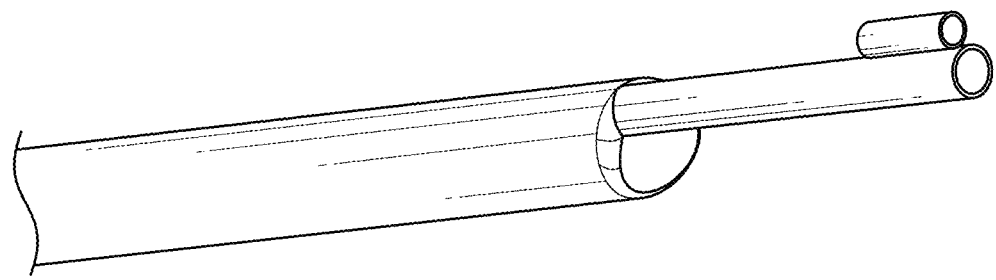

FIG. 3C illustrates an embodiment wherein the larger/major, e.g., non-circular, lumen defined in the main body can act as a delivery lumen for a catheter that can be steerable (e.g., by a steering wire) or that can have a curve preformed into it (e.g., by heating and bending the catheter if polymeric in composition) that the catheter can assume after it is advanced distally out of the distal end of the major lumen of the main body. As presented in FIG. 3D, the distal tubular segment can be provided with a further tubular member disposed thereon, or integrated therewith in a co-extrusion, that can act as a guidewire lumen to facilitate a rapid exchange ("RX") procedure with the guidewire rather than having the guidewire traverse the entire length of the catheter as in an over the wire ("OTW") procedure.

Figure 4:
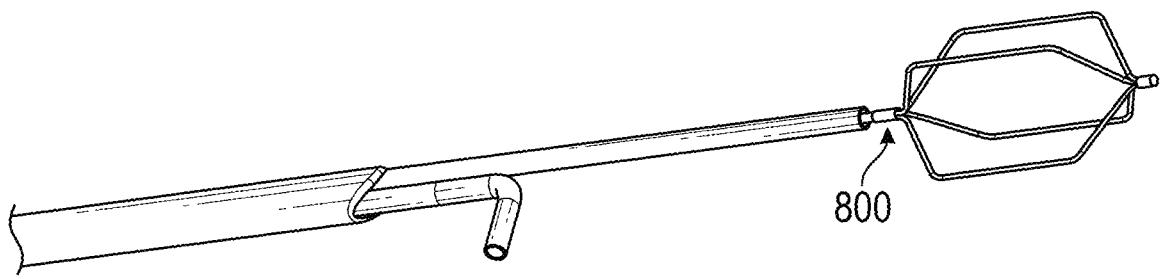
FIG. 4 presents the embodiment of FIG. 3A including a snare catheter disposed through the minor lumen for effectuating capture, for example, of a guidewire in a medical procedure.

FIG. 4 presents the embodiment of FIGS. 3A-3D, but including a snare catheter 800 disposed through the minor lumen for effectuating capture, for example, of a guidewire in a mitral cerclage procedure as set forth in U.S. patent application Ser. No. 15/796,344, filed Oct. 27, 2017. Further aspects of the snare catheter can be seen in that application, as well as in U.S. Provisional Patent Application Ser. No. 62/615,309, filed Jan. 9, 2018. Each of the foregoing applications is hereby incorporated by reference for any purpose whatsoever. The present catheter can be used, for example, for such mitral cerclage procedures. For example, the snare catheter can be used to capture a guidewire while the major passage accommodates an articulating catheter as described hereinabove for grasping a cardiac valve leaflet, or other structure.

Figure 5A:
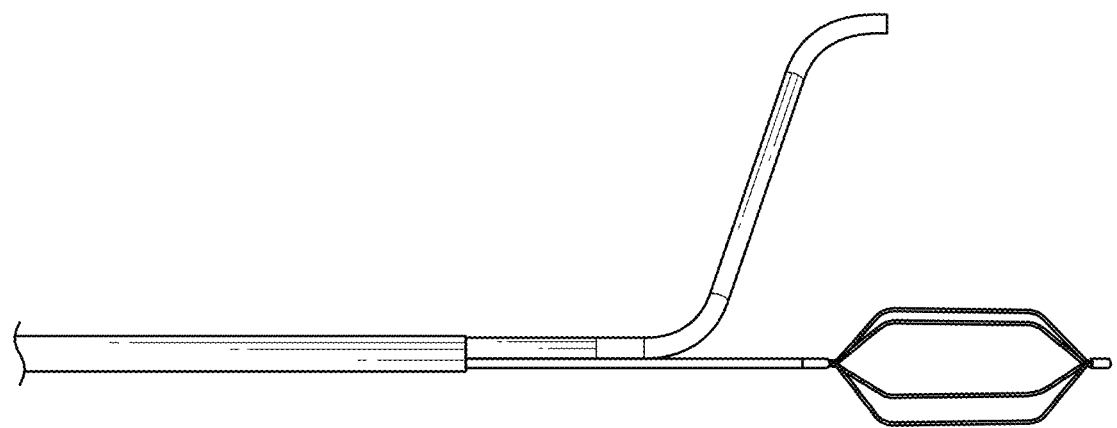
FIGS. 5A-5B illustrate an articulating catheter having two preformed bends that resume their bent shape when advanced distally from the main catheter.
Figure 5B:
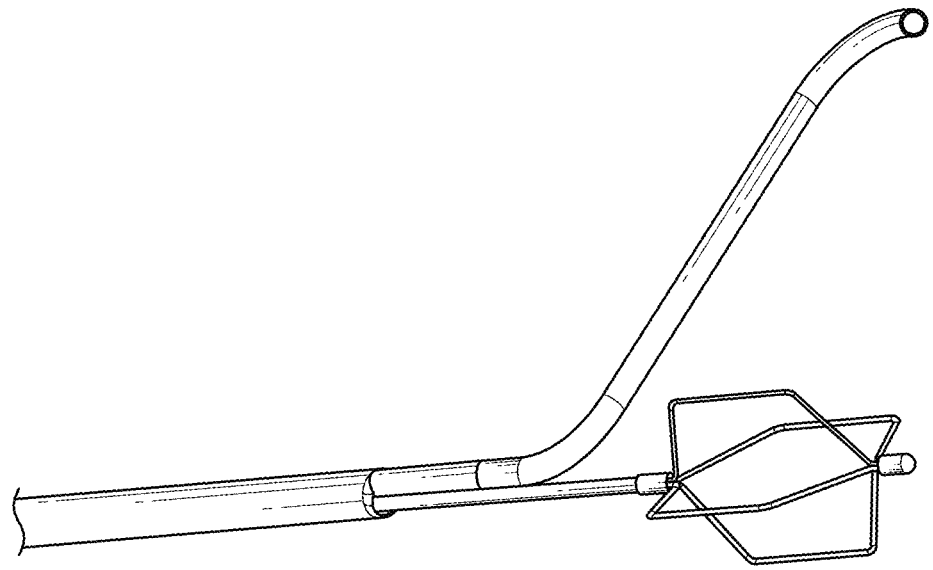
Figure 6:
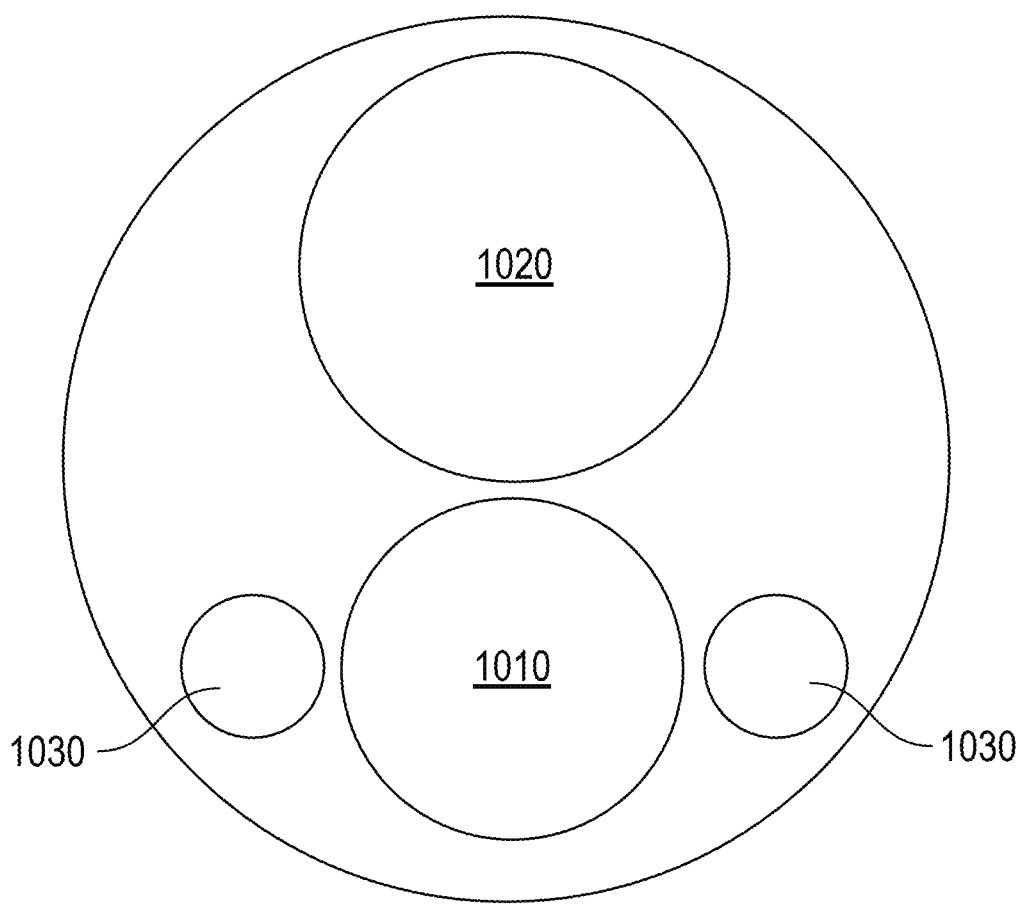
FIG. 6 illustrates an illustrative cross section of a catheter in accordance with the present disclosure.

A further embodiment is presented in FIGS. 5A-5B, which illustrates an articulating catheter having two pre-formed bends that resume their bent shape when advanced distally from the main catheter. FIG. 6 illustrates a further possible cross section for the main catheter, wherein major and minor lumens 1010, 1020 are presented, but two additional steering wire lumens 1030 are presented. If desired, further steering wire lumens are presented that can be used for housing a pull wire that is attached at its distal end to a portion of the catheter (not shown), such as to a ring collar that is formed on or in the body of the catheter.

Figure 7A:
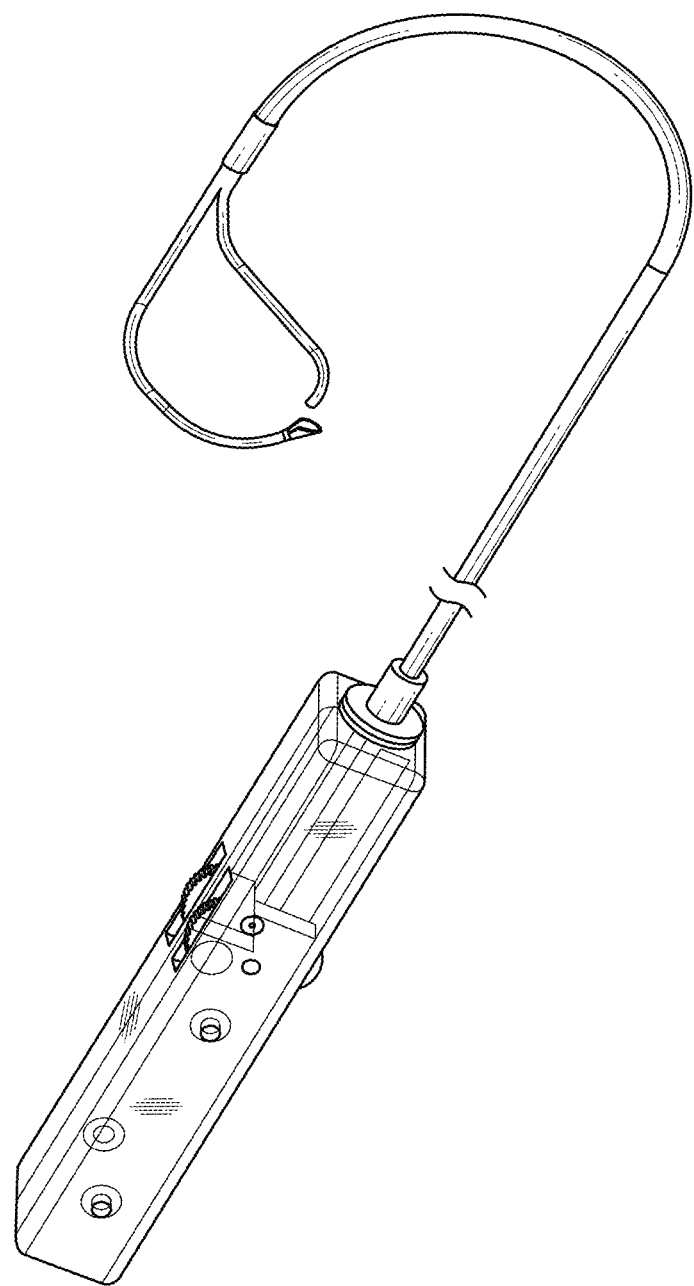
FIGS. 7A-7C present various views of a further embodiment of a catheter in accordance with the present disclosure.
Figure 7B:
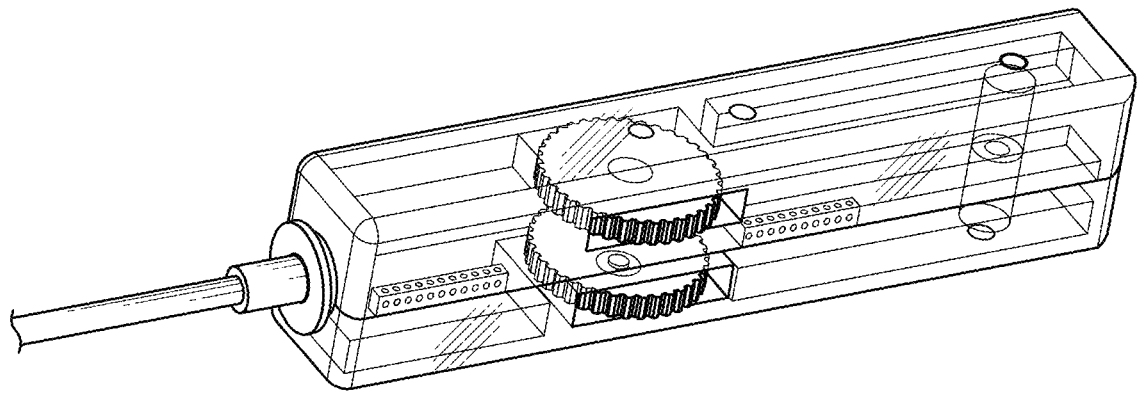
Figure 7C:
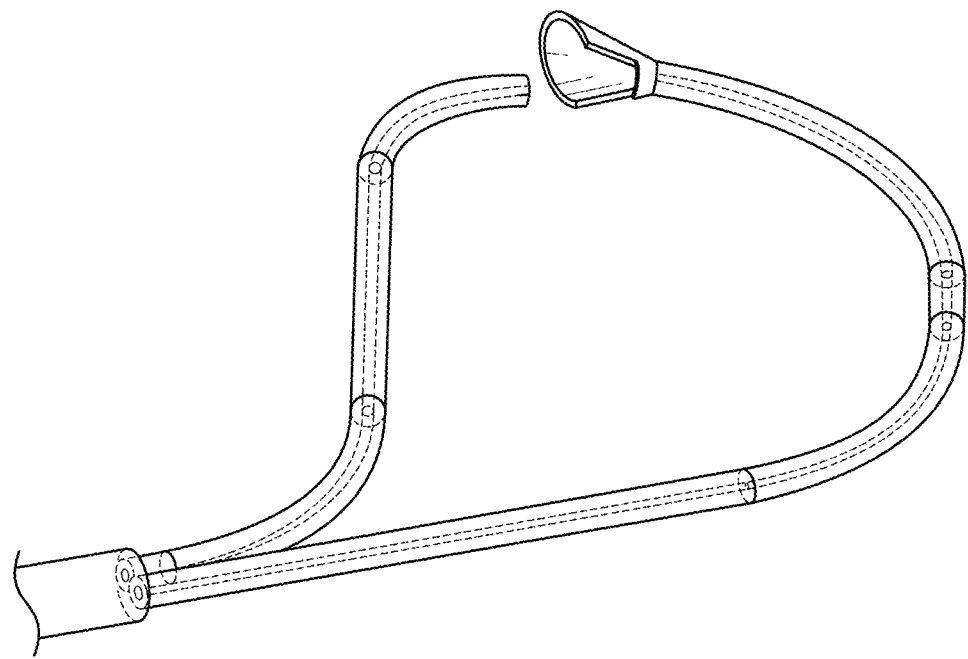
Figure 8A:
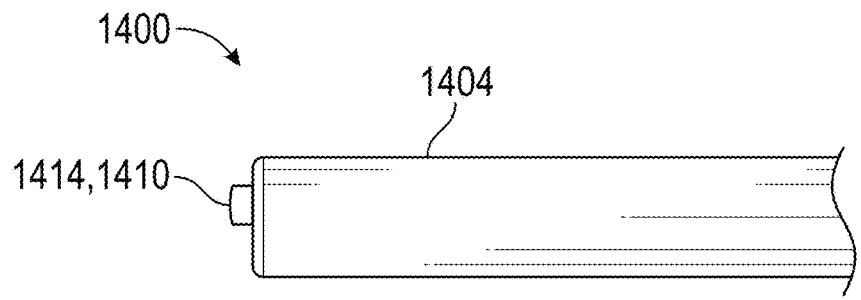
FIGS. 8A-8E present views of still a further catheter in accordance with the present disclosure.
Figure 8B:
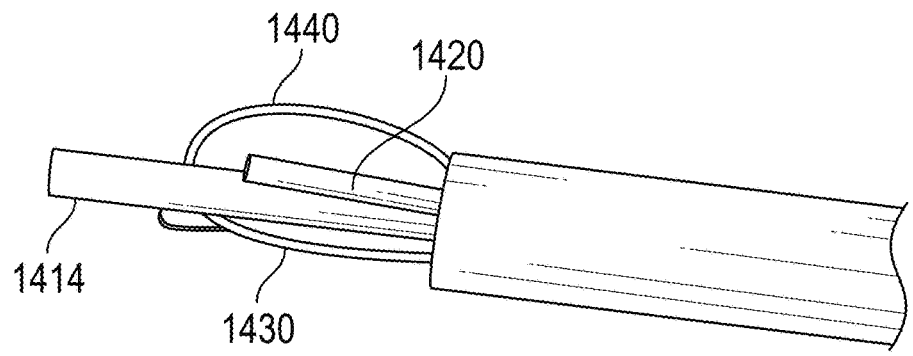
Figure 8C:
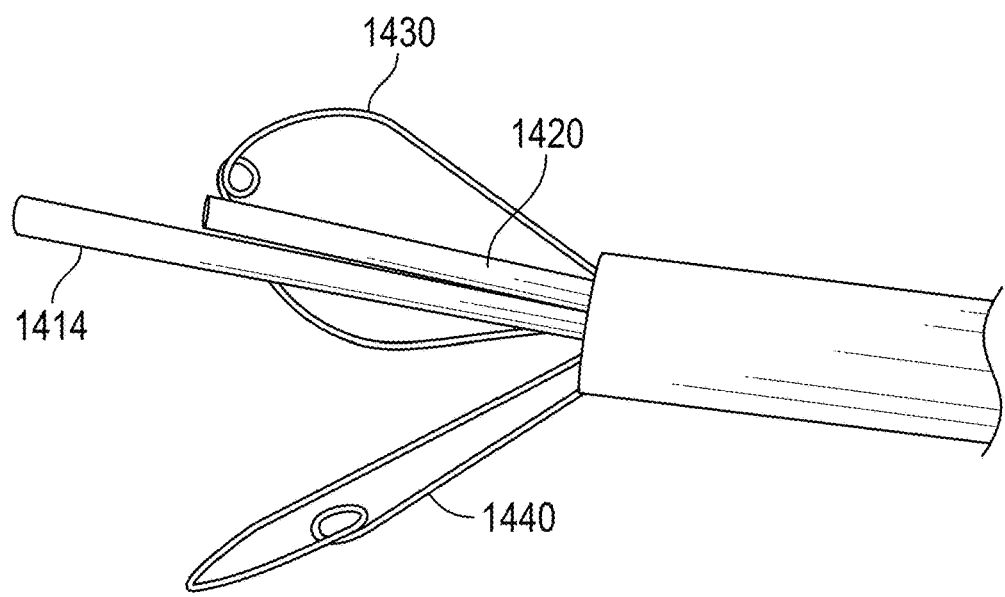
Figure 8D:
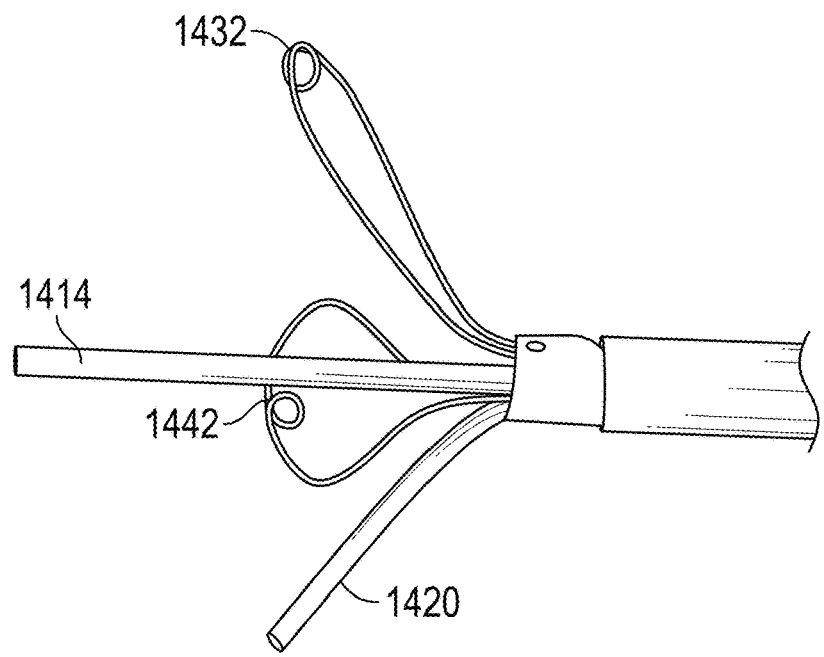
Figure 8E:
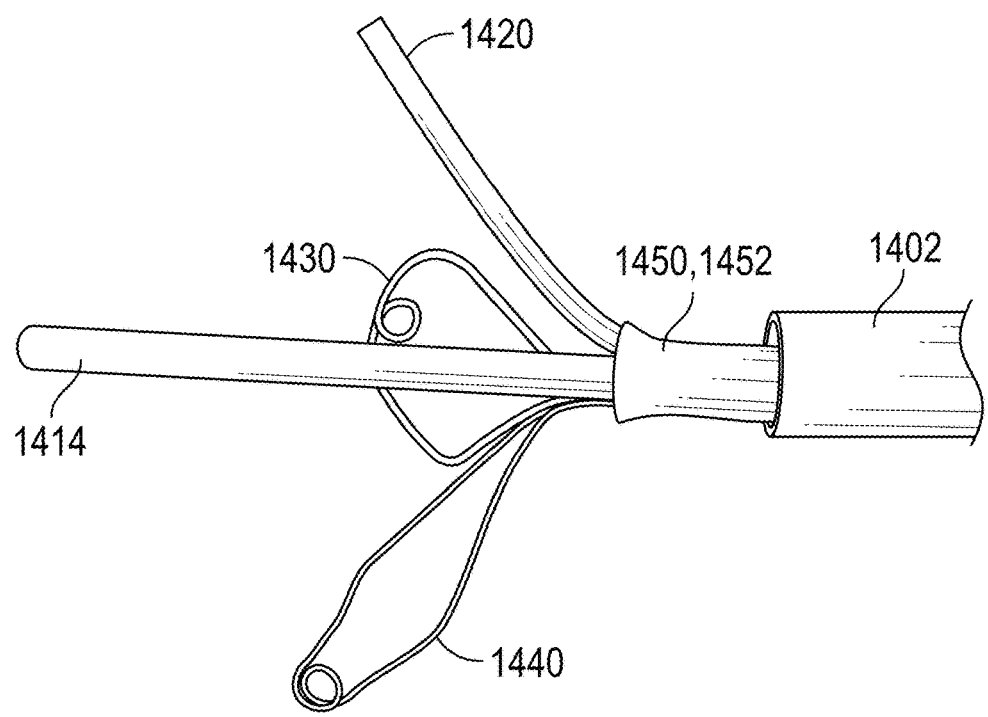

FIGS. 7A-7C display a further embodiment of a catheter in accordance with the disclosure (or aspects thereof) that includes a scoop on one of the articulating arms as presented. The scoop, or funnel, can help guide the other articulating arm into contact with it. If desired, permanent magnets can be added at the end of each articulating arm (not shown), or a winding around each end of the catheter can be made to form a solenoid on the end of each of the arms (not shown). When electrical current is run along the same helical direction through each solenoid, the created magnetic fields add to each other, and attract each other, causing the arms to move more closely together into contact. The force is directly proportional to the current that passes through the windings. Also illustrated is a push-pull actuator for relatively articulating each of the deployable limbs in the catheter. The disclosed catheter uses a toothed wheel, or gear, that rotates around an axle and engages a gear rack in a sliding track that in turn is attached to one of the articulating arms.

For purposes of illustration, and not limitation, FIGS. 8A-9C depict yet another embodiment of a catheter in accordance with the present disclosure.

FIGS. 8A-8E illustrate a further embodiment 1400 of a catheter. The distal end 1404 of catheter 1400 is depicted to highlight its functionality. Catheter 1400 also includes a proximal end and elongate body (not shown) having one or more actuators to manipulate the various sub-components of catheter 1400 described in detail below. Catheter 1400 is defined by an outer tubular member having a proximal end, a distal end 1404, and defines an elongate passage therethrough along its length. Elongate passage slidably accommodates an intermediate tubular member 1450 therein having a proximal end (not shown), a distal end 1452 and in turn also defining a passage along its length for slidably receiving a subassembly therein including at least one further catheter, tool or manipulator. As illustrated in FIGS. 8A-8E, a subassembly is provided slidably received within intermediate tubular member 1450 that includes a central tubular member 1410 having a proximal end, a distal end 1414, and defining a passage along its length, for example, for receiving a guidewire for guiding catheter 1400 to a target location. As illustrated, central tubular member 1410 is a straight member, but can be imparted with a curvature if desired. The subassembly further includes a second tubular member 1420 having a proximal end (not shown), a distal end 1424 and an elongate body defining a central lumen along its length. Second tubular member 1420, as illustrated, has a curvature imparted to it. Also provided are collapsible loops 1430, 1440, which may be made from any suitable material. The particular loops illustrated are formed from nitinol. Each loop is defined by a filament that can include a stress distribution loop (1432, 1442) formed therein that traverses 360 degrees or more. Providing a stress distribution loop facilitates collapse of the loops 1430, 1440 by distributing the bending stress over a longer effective length of wire. The material from which loops 1430, 1440 is formed can extend to the proximal end of the catheter 1400, or may be secured in the distal ends of additional tubular members (not shown) that are slidably disposed in intermediate tubular member 1450. Loops can be made, for example, from shape memory material such as various nickel titanium alloys.

As illustrated, the subassembly within tubular member 1450 can be both slidably and rotatably movable with respect to the outer tubular member of catheter 1400. If desired, each of the subcomponents 1410, 1420, 1430 and 1440 may be slidably and rotatably movable with respect to each other, and the main body of the catheter 1400 as well as the intermediate tubular member 1450.

Figure 9A:
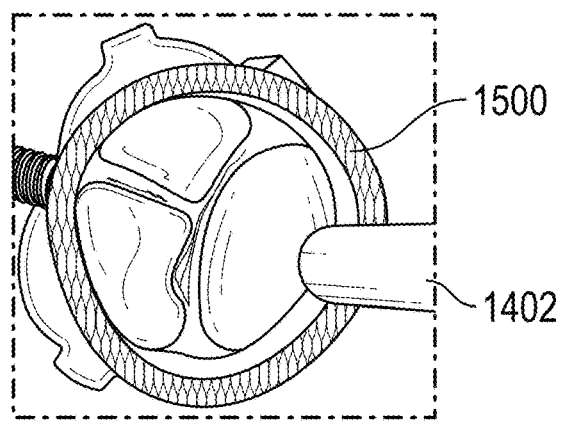
FIGS. 9A-9C present various views of a procedure using the embodiment of FIGS. 8A-8E with respect to the anatomical structure of a tricuspid valve.
Figure 9B:
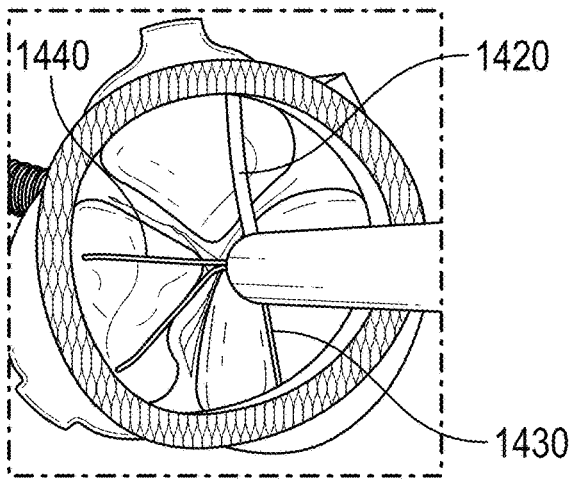
Figure 9C:
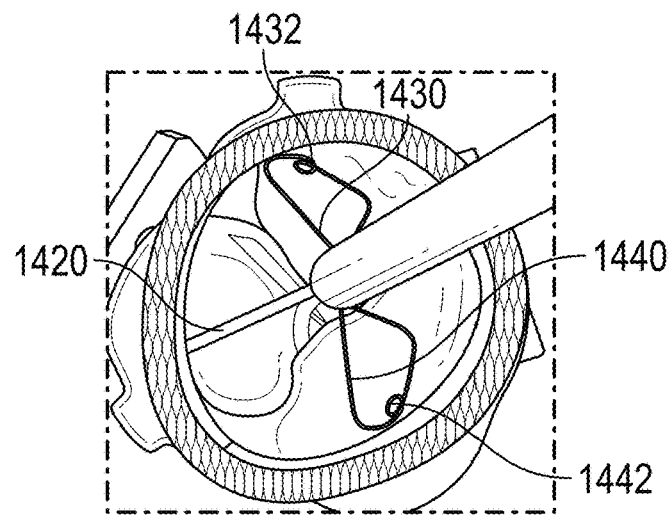

As illustrated in FIGS. 9A-9C, the embodiment 1400 is illustrated in use with respect to the structure of a tricuspid valve. In use, after the distal end 1402 of catheter 1400 is advanced, for example, to a tricuspid valve, the subassembly housed within intermediate tubular member 1450 is advanced distally out of distal end 1402 of catheter 1400, and the distal end 1414 of central tubular member 1410 can be directed through the center of the tricuspid valve between the leaflets. Next, the two loops 1430, 1440 are deployed and advanced under the leaflet against the center of each leaflet by the valve annulus. This permits tubular member 1420 to be positioned at the center of the third leaflet by the annulus. At this time, any desired instrument, such as a cutting wire or piercing instrument can be advanced through the leaflet at its edge by the annulus, such as to advance an electrosurgical cutting wire through the leaflet, permitting the cutting wire to be dragged radially inwardly through the leaflet to cut the leaflet in half. In accordance with a further example, a suture can be anchored by subassembly component 1420. The suture can then be used as a guide rail for delivering a prosthesis to be implanted over the leaflet, without cutting it in half first. It will be appreciated that catheter 1400 can be used in many different types of procedures and that these illustrations are only examples.

U.S. Patent Application No. 62/913,150, filed Oct. 9, 2019 and U.S. Patent Application No. 62/913,158, filed Oct. 9, 2019 set forth further implementations of a leaflet tissue excision system in accordance with the present disclosure. For purposes of illustration, and not limitation, these illustrative implementations of systems that can be used to remove valve clips, Alfieri stitches, cysts, tumors, or other structures, as desired, are set forth in FIGS. 10A-18G.

With specific reference to FIGS. 10A-10F, a removal system for a valve clip, cyst and the like is illustrated. The system includes a catheter that includes a deployable cutting snare and associated capture system. In particular, the catheter includes an inner tubular member having a proximal end and a distal end that includes a deployable cutting snare 1520 slidably disposed therein. The cutting snare can be deployed by advancing it distally, wherein the cutting snare is configured to form a loop that can surround a structure. After a structure has been surrounded, such as a mitral clip or the like, the snare can be withdrawn to permit it to cut through tissue or other structure, and the removed structure can be captured and withdrawn by the capture or holding snare 1510. The cutting snare 1520 can be electrified and be electrically exposed or denuded about its inner periphery to help it burn through tissue, and if desired can be electrically insulated about its outer periphery. As illustrated in FIG. 10C, the cutting snare forms a loop that is characterized by two parallel sections that bow outwardly to form a ring shape, wherein a distal end portion includes a further bend to form a distal tip. The distal tip is depicted at the top of the loop in FIG. 10C, and it is characterized by a sharp bend that transitions on each side to a sweeping arc to define a loop. The segments of the snare then bend orthogonally so as to travel inside the lumen of the inner tubular member, where they emerge on a proximal end of the catheter where they are attached to an actuator or handle that can pull the snare proximally with respect to the inner tubular member. The proximal ends of the snare catheter can be denuded and connected to a power supply capable of monopolar or bipolar operation, as desired. The distal portion of the snare catheter can be formed from heat treated shape memory material (e.g., a nickel titanium alloy) to expand into a hoop configuration as illustrated, or can be formed from a regular conductor that is configured to bow outwardly when unconstrained, as desired. The snare can include radiopaque material and the distal end of the inner tubular member can include a radiopaque marker, as desired to facilitate visualization of the catheter under visualization.

As further illustrated in FIGS. 10A-10F, the capture or holding snare 1510 can be mounted to the outside of and move with the inner tubular member, or may be mounted to an intermediate tubular member (having a respective proximal end, distal end and elongate tubular body) that slides over the inner tubular member to facilitate relative axial placement of the cutting snare and the capture snare. The capture or holding snare includes a collapsible basket formed, for example, from a laser cut hypotube formed into a stent-like pattern defined by zig-zag rows of struts or the like. A cinching tether is woven about an open distal end of the basket having at least one end (in the present embodiment two ends) that are threaded down an annular lumen defined between an outer surface of the intermediate tubular member (if provided, otherwise the outer surface of the inner tubular member) and an outer tubular member of the catheter (the outer tubular member having a respective proximal end, distal end and elongate tubular body). A distal end portion of the outer tubular member can be slightly enlarged, if needed, to accommodate the capture basket as illustrated. The basket can be made from a heat treated shape memory material (e.g., NiTi alloy, braided or non-braided composite metal, polymer, or formed polymer) so as to self-expand into a basket shape when unconstrained, wherein the distal mouth or opening of the basket includes the interwoven tether that is routed in and out of the fenestrations of the basket about the distal open end of the basket. By applying tension to a proximal end of the tether that is routed to the proximal end of the catheter, the looped tether at the end of the basket closes down and closes the basket, applying a hoop stress and grabbing force to any object that has been introduced into the basket, such as a mitral clip to be removed, tissue containing an Alfieri stitch, a cyst, polyp, or other undesired anatomical formation, as desired. As illustrated, the basket can be affixed to the intermediate tubular member using a radiopaque marker that surrounds the proximal end of the basket and the intermediate tubular member and a distal radiopaque marker band that surrounds a radially inner portion of the basket adjacent the intermediate tubular member and the intermediate tubular member itself. As illustrated, the intermediate tubular member includes a distal radiopaque marker so as to enhance visibility of the instrument under fluoroscopic visualization.

If desired, the outer tubular member of the catheter can include an enlarged distal segment as illustrated in FIG. 10F. FIGS. 10D and 10E illustrate deployment of the outer tubular member out of a distal end of a guiding catheter. FIGS. 10D and 10E respectively illustrate the laser cut portion pre and post—expansion, and FIG. 10F illustrates a relatively larger diameter distal portion on the delivery sheath or outer tubular member. Marker bands can be provided at the at the distal end of each tubular member of the catheter, and the snares and baskets of the catheter can include radiopaque material. If desired, the basket can be provided with an outer tubular layer of polymer coating or film so as to help house an excised clip or tissue segment, as desired. The outer tubular member can have a deflectable distal tip. In a further embodiment, the laser cut hypotube basket can be replaced with a polymeric tubular section that can expand about a mitral clip or other structure without buckling.

Figure 11A:
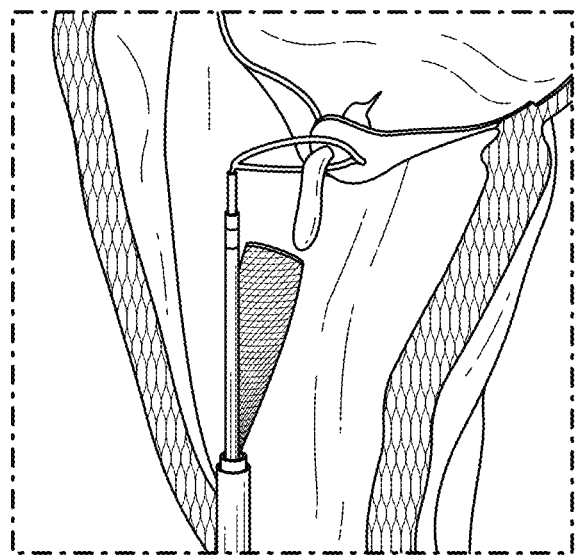
Figure 11B:
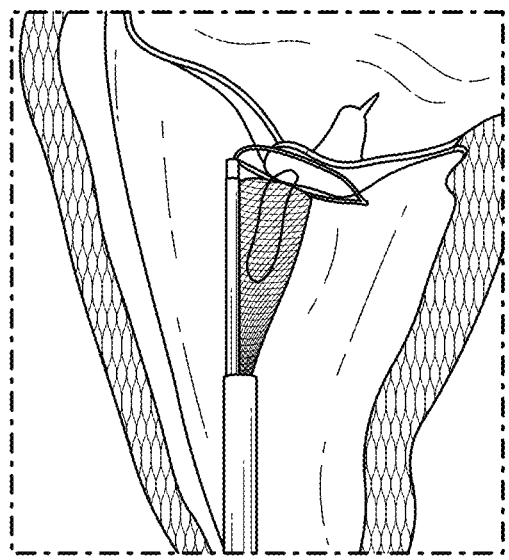
Figure 11C:
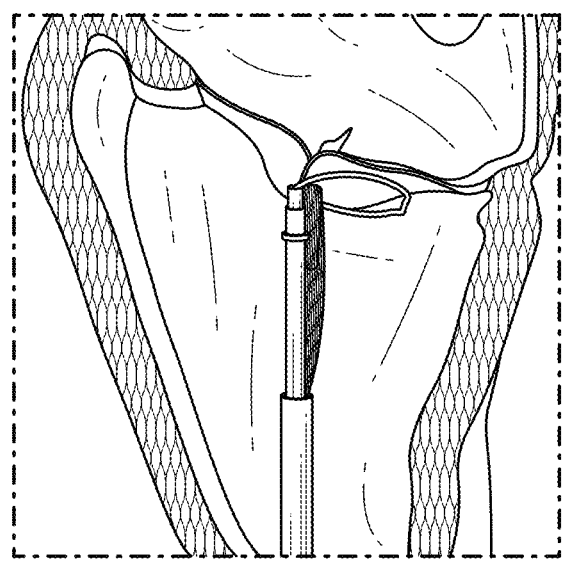
Figure 11D:
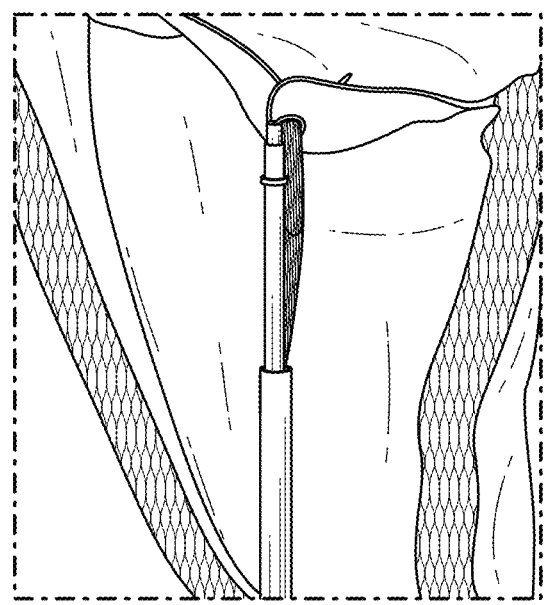

For purposes of further illustration, FIGS. 11A-11D present illustrative method steps that can be executed to remove a previously installed valve clip, in this illustration, a mitral clip, that is affixed to two coapting valves. This procedure is very advantageous as it is performed percutaneously or apically, as desired, while the patient's heart is beating, avoiding the need for open heart surgery and/or stopping the patient's heart. First a distal end of the catheter is introduced apically through a bottom wall of the ventricle underneath the mitral valve. The inner tubular member is advanced distally with respect to the outer tubular member or delivery sheath and the snare is deployed distally with respect to the inner tubular member so that it takes on a preformed hoop shape that orients itself orthogonally or approximately orthogonally with regard to a longitudinal axis of the catheter. The cutting snare is then positioned so as to surround tissue or be adjacent tissue near the leaflets, with the mitral clip (or other material to be removed, as desired) being surrounded by the cutting snare. Next, the intermediate tubular member bearing the capture basket is deployed distally from the distal end of the outer tubular member, and the open end of the capture basket is maneuvered over the mitral clip (or other material to be removed) so that the capture basket surrounds a majority of the mitral clip, as illustrated in FIG. 11B. Next, the top of the capture basket is cinched around an upper end of the mitral clip to mechanically capture it, as illustrated in FIG. 11C. Next, the cutting snare is withdrawn into the inner tubular member, cutting through valve leaflet tissue that is attached to the mitral clip. As mentioned above, the cutting snare can be electrified. The basket and inner tubular members can then be withdrawn proximally into the outer tubular member or delivery sheath, and be withdrawn. It will be appreciated that the intermediate tubular member could be omitted and the basket could instead be attached to the inner tubular member, but provision of the intermediate tubular member can provide an additional degree of mechanical freedom when performing the procedure.

Figure 12A:
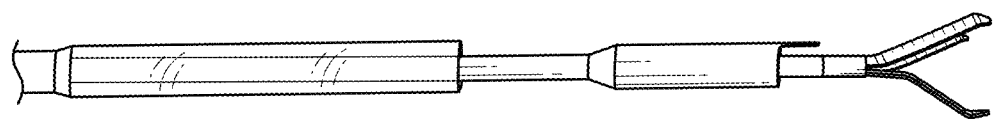

In a further implementation, FIGS. 12A-12E present a further remover device that can be used to remove a clip, cyst, stitch or the like in accordance with the present disclosure. FIG. 12A illustrates that the device includes an outer tubular member or outer delivery catheter housing having a proximal end and a distal end that surrounds and slidably receives an intermediate tubular member (having a proximal end and a distal end) having clip or cyst housing with a cutter tip at a distal end region thereof. Within the intermediate tubular member, an inner catheter is slidably received that includes a deployable gripper to grab a clip or other structure to be removed from a patient's anatomy. As illustrated, the gripper includes three gripping arms that are configured to bias radially outwardly when unconstrained. Each gripping arm can be formed from a planar strip of material that terminates in a converging distal tip. As illustrated, each gripping arm has a proximal end affixed to a distal end of an inner tubular member or solid member of the inner catheter. Each arm, as illustrated, then has a preformed bend that bends the arm radially outwardly, and then bends radially inwardly as the arm approaches a tapered distal tip. Two, four or more gripping arms can be used, as desired.

Figure 12B:
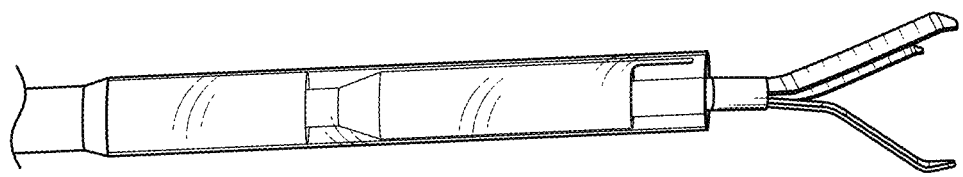
Figure 12C:
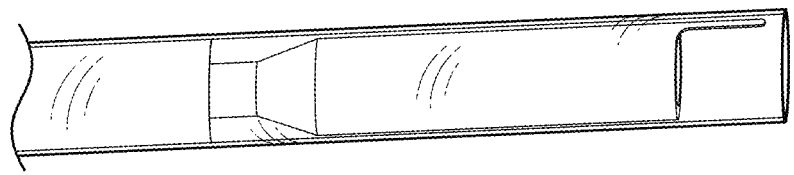
Figure 12D:
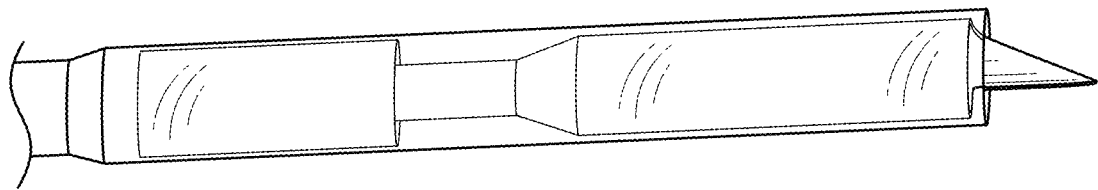
Figure 12E:
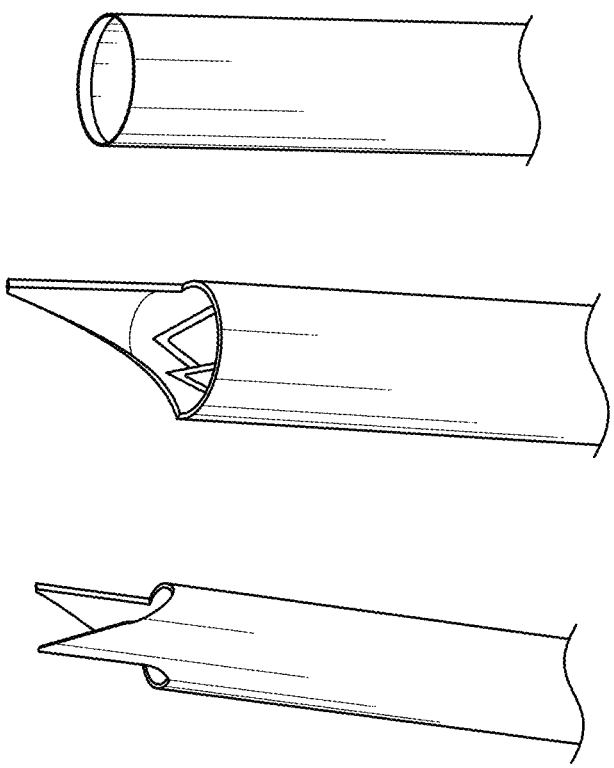

The gripping arms can be formed from polymeric or metallic material, as desired, and may be formed from shape memory material or material that is formed to otherwise spring outwardly when radially unconstrained. The griping arms can be configured so as to collapse radially inward when pulled proximally into a tubular member, such as the cutter tip of the illustrated catheter. The gripper can be withdrawn proximally into the clip or cyst housing of the intermediate tubular member, and the intermediate tubular member can be withdrawn proximally into a distal end region of the outer delivery catheter housing. FIG. 12B shows an enlarged view of the distally extended gripper. FIG. 12E illustrates different implementations of cutting tips that can be used for the cutter tip of the intermediate tubular member. For example, the cutting tip can include a round coring edge characterized by a sharpened annular surface, or may include a distal end that terminates in one or two cutting edges that are tapered extensions of the tubular wall that are sharpened along one or both edges to cut tissue when the intermediate tubular member is rotated with respect to an anatomical structure that the cutting tip or tips have been pushed against. As illustrated in FIG. 12C, the cutter housing of the intermediate tubular member is retracted into the outer delivery catheter until it is delivered, and it is then advanced distally into a position where it cuts leaflet tissue, for example, when rotated, as illustrated in FIG. 12D.

Figure 13A:
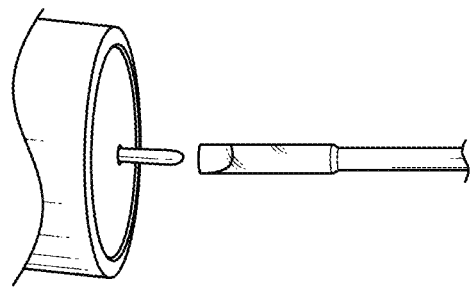
Figure 13B:
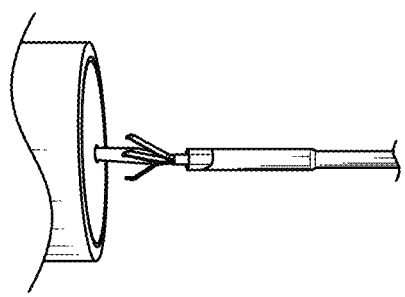
Figure 13C:
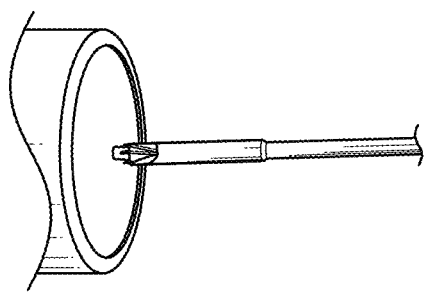
Figure 13D:
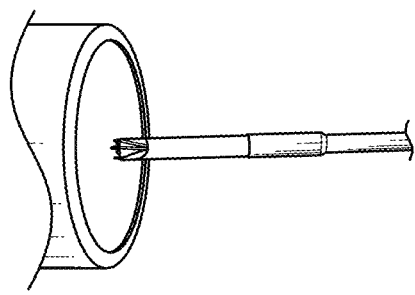
Figure 13E:
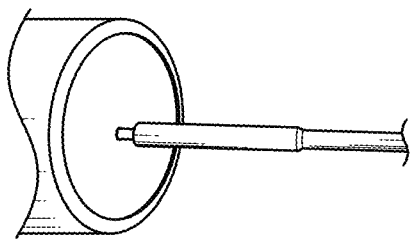
Figure 13F:
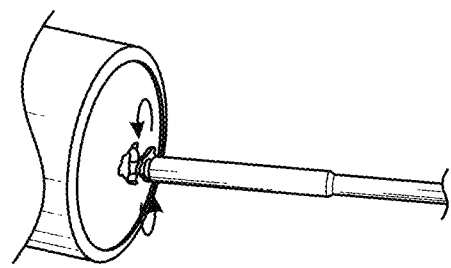
Figure 13G:
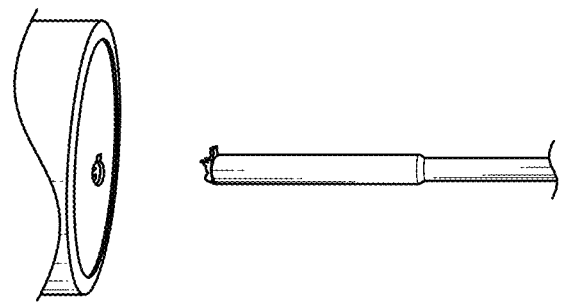
Figure 13H:
Figure 13I:
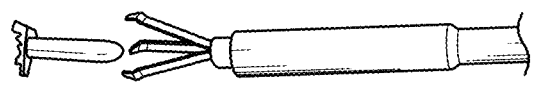

As illustrated in FIG. 13A-13I, the device of FIG. 12 can be used to grip and excise an object, such as a mitral clip. FIG. 13A illustrates simulated relative placement of the catheter below an existing mitral clip. FIG. 13B illustrates distal extension of the gripper out of the distal end of the outer tubular member or delivery catheter, up and over the clip or cyst such that the gripper surrounds the cyst. The cutter housing is then advanced distally with respect to the gripper so as to cause the radially outwardly biased arms of the gripper to be pushed inwardly under the force of the distally extending cutter housing, thereby grasping the clip or other structure. As illustrated in FIG. 13D, the outer sheath can then be advanced distally toward the leaflets. The cutter housing can then be distally advanced to contact and pierce the tissue as illustrated in FIG. 13E. FIG. 13F illustrates relative rotation of the cutter housing with respect to the tissue to cause the cutter to form a circular cut to remove an object from the anatomy, such as a mitral clip. Once the tissue or other material has been cut, the clip, cyst or other material can be retracted into the outer sheath and removed from the patient. As illustrated in FIGS. 13H and 13I, the clip or other removed material can then be expelled from the catheter after it has been removed from the patient.

FIGS. 14A-18G illustrate an implementation of a twisting catheter that can be used to twist a planar tissue structure or other structure, such as a native or replacement leaflet, withdraw it into a catheter to capture the tissue, which can then be cut off from surrounding anatomy.

Figure 14A:
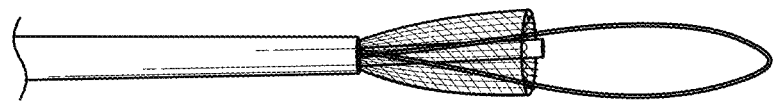
Figure 14B:
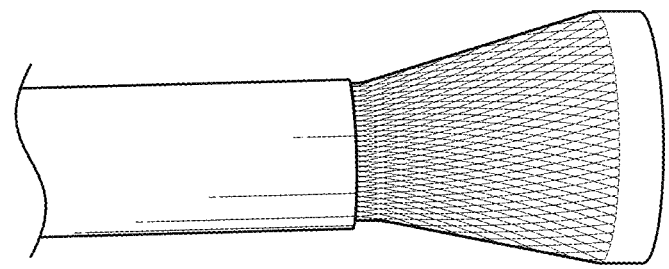
Figure 14C:
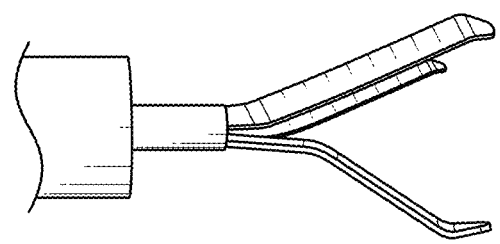
Figure 14D:
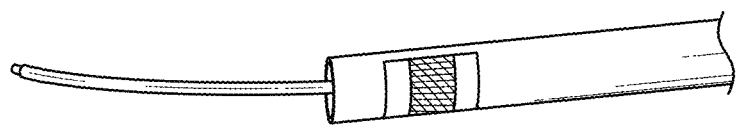
Figure 14E:
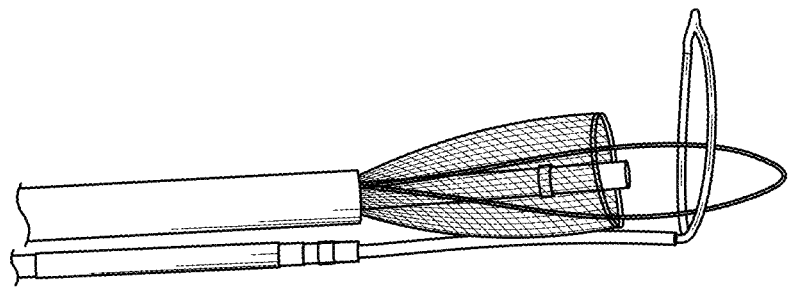

Specifically, FIG. 14A illustrates a distal end region of a twisting catheter that includes an expandable basket similar to the embodiment of FIG. 12 above or a tubular end that includes a twisting catheter inside of it that may have two lumens to accommodate an electrified guidewire therein. Alternatively, as illustrated in FIGS. 14B and 14C an inner elongate member can be provided with including a gripper as with the embodiment of FIG. 13 that is slidably disposed within an intermediate tubular member. FIG. 14D illustrates the guidewire of FIG. 14A having an electrified distal tip prior to being formed into a loop. FIG. 14C illustrates relative placement of an electrified snare catheter with respect to the twisting catheter and capture catheter, discussed in further detail below. The basket of the twisting catheter can be made of braided or non-braided composite metal, NITI, polymer, formed polymer, and the like. The electrified snare of FIG. 14E is fully insulated except at the distal loop and the proximal 0.5 inches which is connected to the RF generator. The electrified snare can be its own separate catheter, or it can be delivered through a long sheath that houses both the twisting catheter and the electrified snare.

Figure 15D:
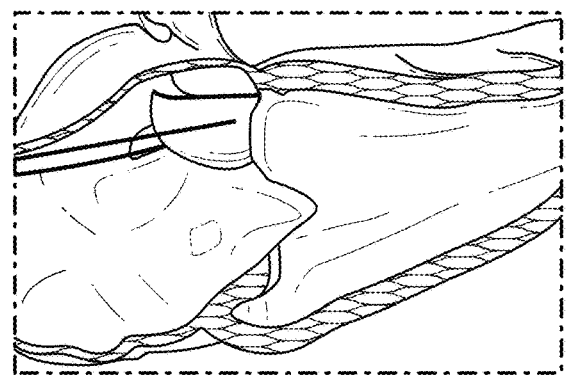
Figure 15C:
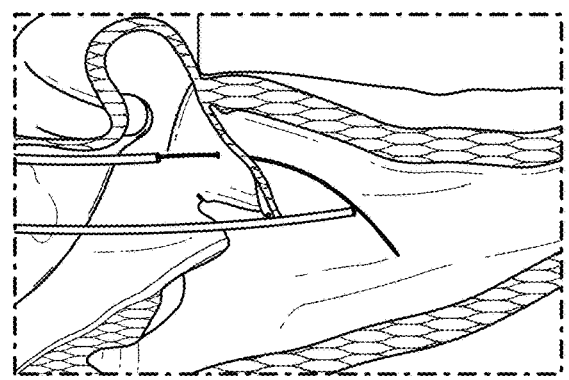
Figure 15B:
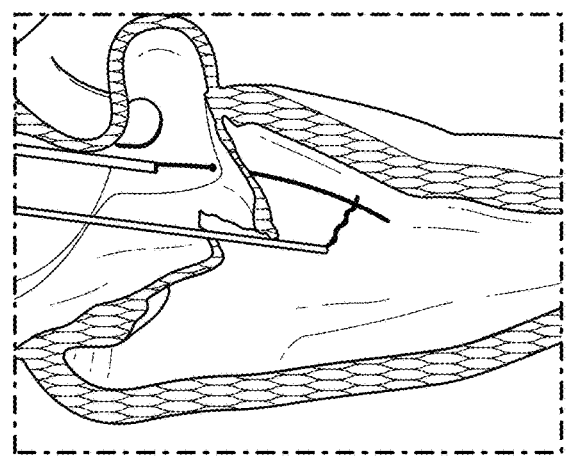
Figure 15A:
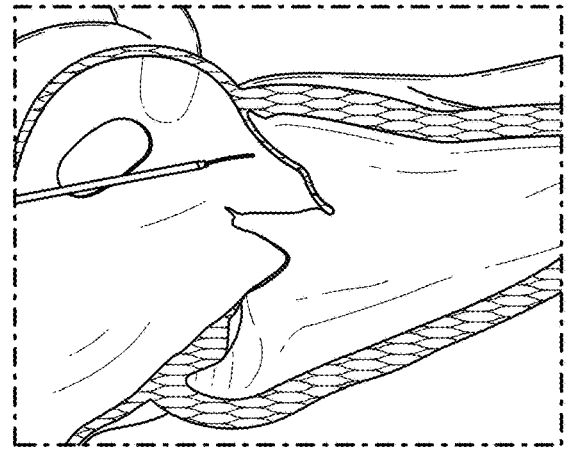

FIGS. 15A-15D illustrate use of the system of FIG. 14 for excision of valve tissue. The leaflet excision device can be used to remove valve tissue from the aortic, mitral, tricuspid and pulmonic valves, for example. It can be used for valve-in-valve tissue removal or for native tissue. The electrified wire can be PTFE or Paralyene coated and then jacketed with PTFE or PET, for example. The electrified wire can be single layer or have a dual layer PTFE jacket or PET or a combination of both. The guidewire can have a pre-kinked or bent section in the middle. This can be accomplished with a slight grind to reduce the diameter, or actually by pre-kinking the wire. The kinked or ground section can be marked with a visible marker band on both sides of the section to facilitate visibility under fluoroscopy. FIG. 15A illustrates positioning of the guide catheter and the electrified guidewire onto the leaflet. FIG. 15B illustrates advancement of the snare catheter, and also illustrates electrification of the exposed distal tip of the guidewire so as to advance the guidewire through the tissue of the valve leaflet.

Figure 16E:
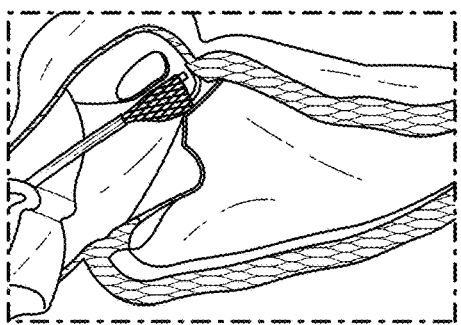
Figure 16D:
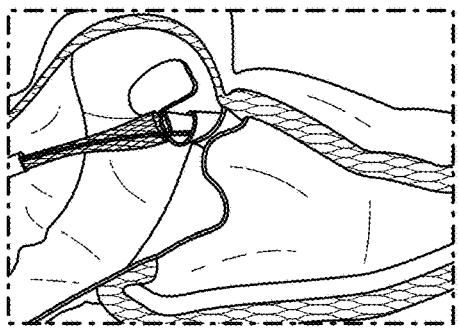
Figure 16C:
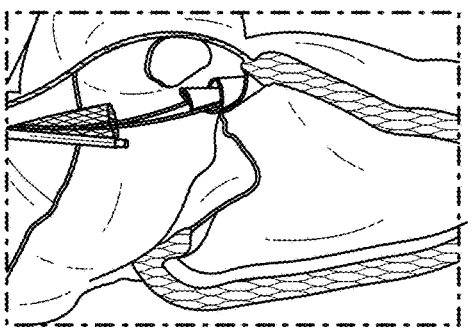
Figure 16F:
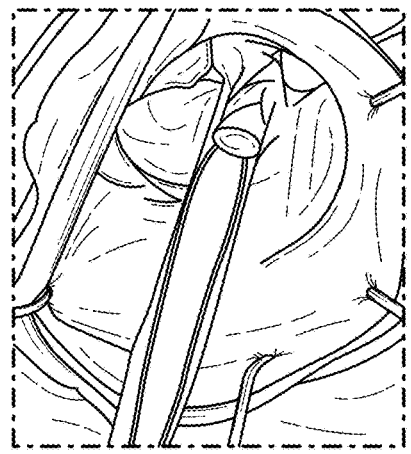
Figure 16B:
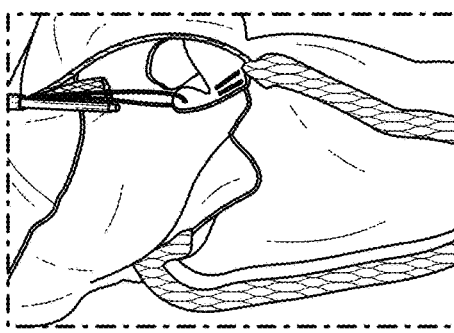
Figure 16A:
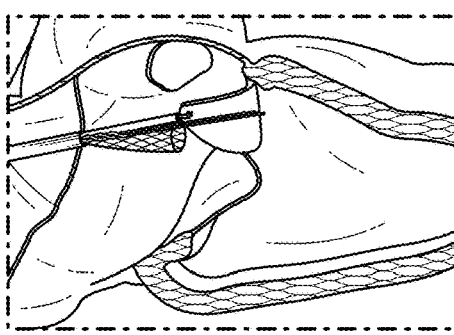
Figure 17C:
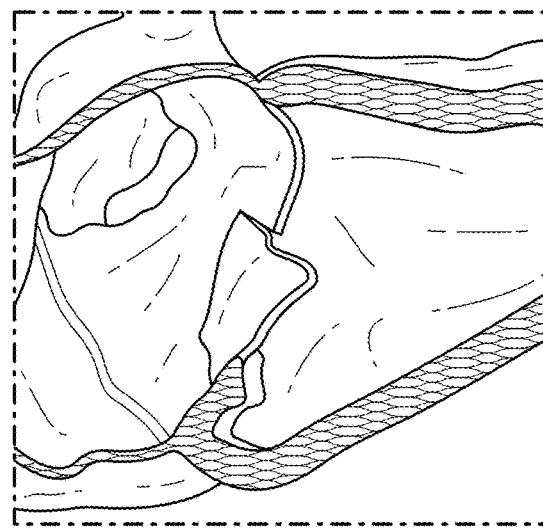
Figure 17B:
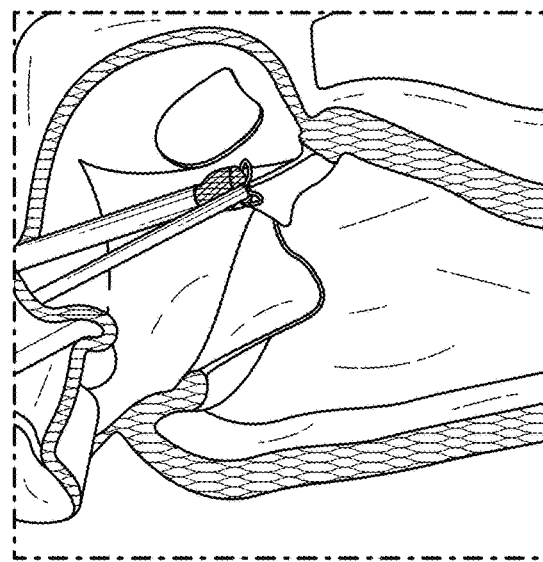
Figure 17A:
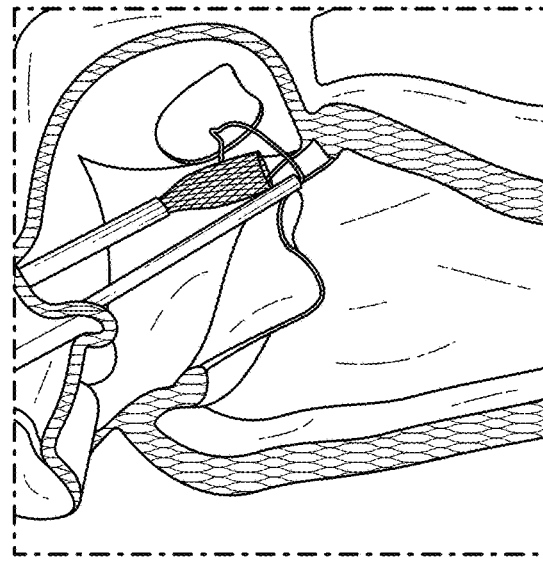

FIG. 15C illustrates grasping of the electrified guidewire with the snare catheter. FIG. 15D illustrates retraction of the guidewire proximally out of the patient using the snare until two ends of wire are externalized from the introducer sheath. FIG. 16A illustrates advancement of the twisting catheter, which can include a dual lumen elongate core member, with one leg of the guidewire passing proximally along each lumen, over both ends of the electrified guidewire. FIG. 16B illustrates twist the tissue by applying torque to the elongate body of the twisting catheter, which has the effect of applying rotational torque to the loop formed by the guidewire about a longitudinal axis of the catheter. FIG. 16C illustrates continuing to twist the tissue by torqueing the twisting catheter until the leaflet is fully gathered. FIG. 16D illustrates distal advancement of the outer tubular member over the inner twisting catheter over the twisted tissue of the leaflet. The tissue is contained by simply sliding the outer tube of the catheter over the elongate inner body and loop. If a basket is provided at the end of the outer catheter, a snare can be tensioned to cause the distal end of the basket to collapse around the tissue of the leaflet. FIGS. 16E-16F illustrate containment and securing of the tissue within the distal tip of the catheter, wherein 16E illustrates use of a basket, and 16F illustrates use of a uses a polymeric outer tube. The electrified snare is then introduced over the combined twisting and outer catheter until it surrounds the base of the twisted tissue. The snare of the twisting catheter can be partially covered by PET or PTFE to reduce exposed surface area and concentrate energy on the tissue. FIG. 17A shows advancement of the electrified snare over the proximal end of the twisting catheter combination, FIG. 17B illustrates cinching the snare over the tissue to be excised and then electrified to cut the tissue. The snare is then retracted while electrified to complete cutting the tissue (FIG. 17C).

Figure 17E:
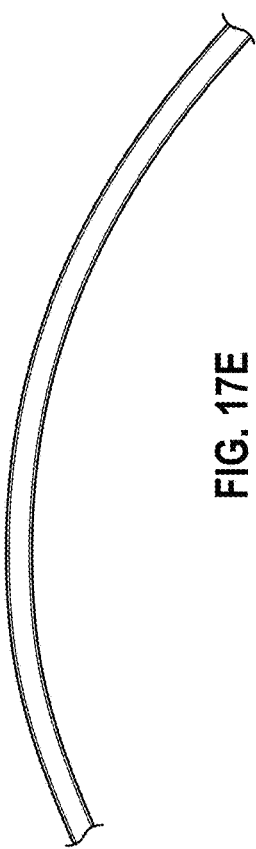
Figure 17D:
Figure 18B:
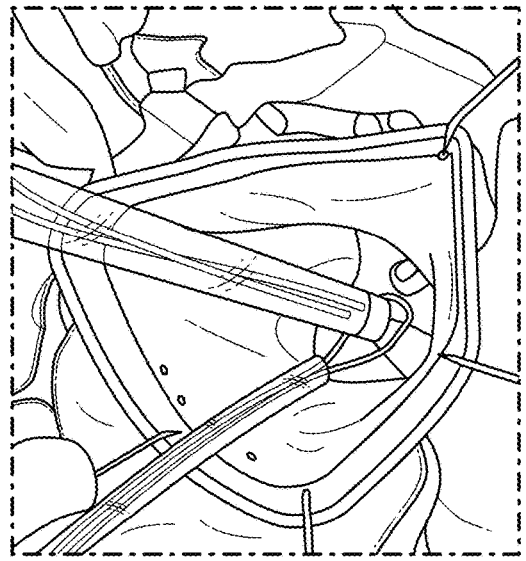
Figure 18D:
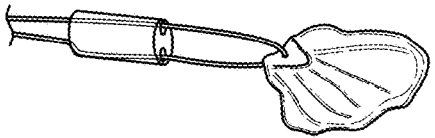
Figure 18A:
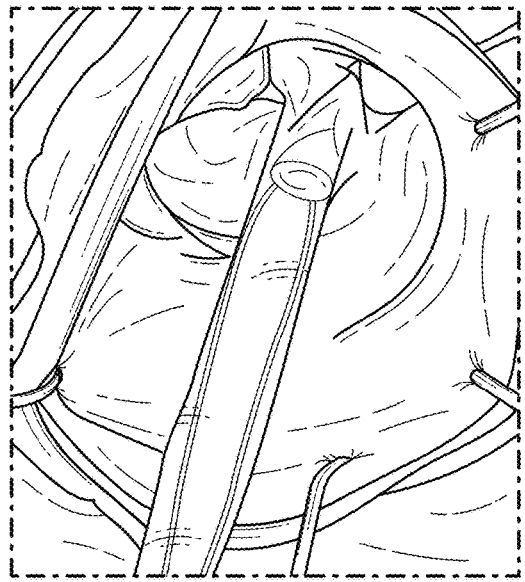
Figure 18C:
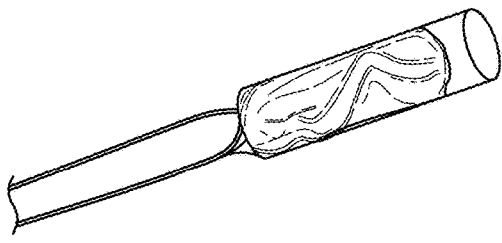
Figure 18G:
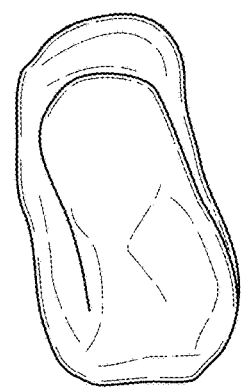
Figure 18F:
Figure 18E:
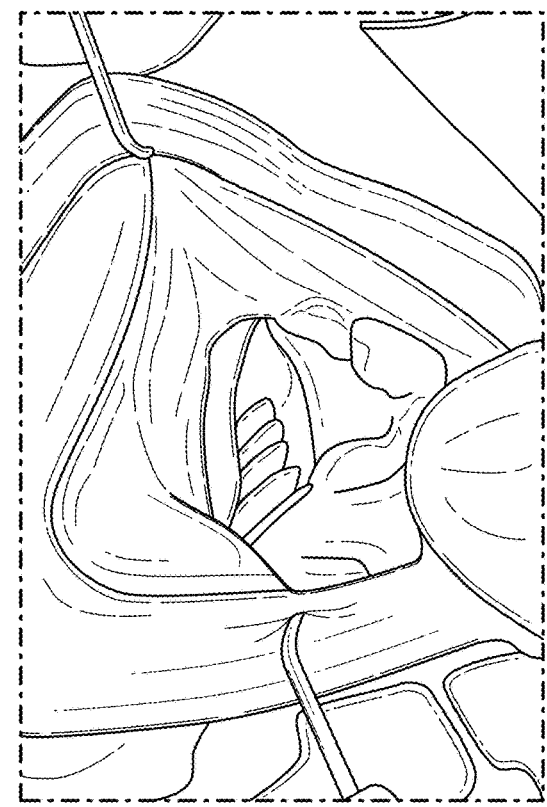

FIG. 17D illustrates aspects of a partially jacketed electrified snare. FIG. 17E illustrates how a small section of inner surface of snare is exposed to permit the outflow of applied power. This exposed section contacts the tissue and focuses the RF energy to that part of the tissue only and prevents inadvertent energy delivery to surrounding tissue. FIGS. 18A-18G illustrate an ex-vivo study with a porcine aorta demonstrating complete excision of an aortic cusp, wherein FIG. 18A illustrates tissue twisted into a catheter, FIG. 18B illustrates an electrified snare positioned over tissue to excise the tissue, FIG. 18C illustrates cutting tissue contained in the catheter, FIG. 18D illustrates the cutting of tissue. FIG. 18E shows the surrounding tissue with the leaflet removed. FIG. 18F illustrates the remaining tissue, and FIG. 18G shows the tissue that was removed.

FIGS. 19A-22C illustrate further implementations of a tissue excision, cutting and removal system. The leaflet crossing wire described above functions as a rail or guide to position the cutting device on the leaflet to be cut. An inner guidewire lumen can be used to distally advance cutting head loops of wire to the edge of the leaflet over the guidewire rail. The cutting head loop of wire can be shaped to take a specific portion of the desired leaflet off to allow for open area for flow near either coronary artery. One cutting head (wire) can be electrified with RF energy or both cutting heads (wires) can be electrified for cutting. If desired, one cutting head loop wire can be electrically exposed and electrified and the other can be insulated. Angled points can be set into the cutting wire to make the cutting wires make positive contact and/or coaptation to ensure a positive burn when the outer delivery catheter is advanced over them during positioning. Placement of the guidewire through the leaflet can allow for removal of the cut portion after cutting. A covering over the opening of the cutting wires may be used to ensure the cut portion of the leaflet is captured in the event of a wire loss and inability to hold the cut portion.

Figure 19A:
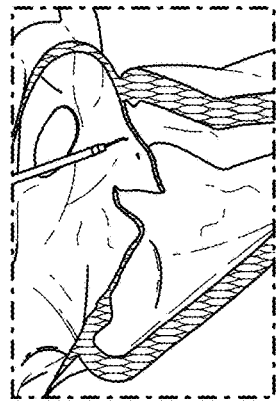
Figure 19B:
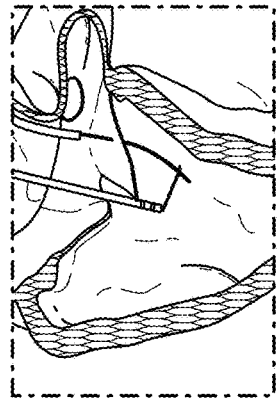
Figure 19C:
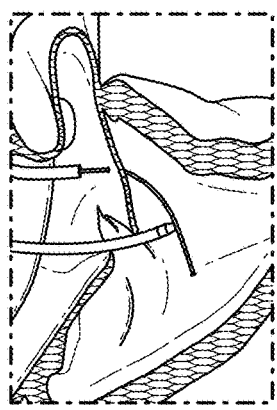
Figure 19D:
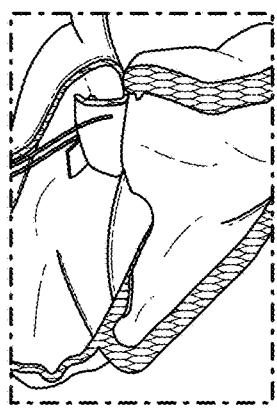

FIGS. 19A-19D illustrate aspects of preparing to use such a system. FIG. 19A issues positioning a guide catheter and electrified guidewire onto the leaflet. FIG. 19B illustrates advancement of a snare to the location where the guidewire exits the leaflet after passing through it. FIG. 19C illustrates grasping of the guidewire with the share, and FIG. 19D illustrates externalization and twisting of the guidewire.

FIGS. 20A-D illustrate a further embodiment of a rail-based leaflet excision and cutting system with modular RF head cutting loops without and with electrical insulation. The delivery catheter for delivering the components can be provided with an expandable tip such as a protection basket for better capturing the leaflet cutting loop. As illustrated, the system includes an outer delivery catheter in the form of a tubular member having a proximal end and a distal end. An inner tubular member can be used to thread the guidewire through after the guidewire has been introduced through the leaflet as illustrated in FIG. 19. This permits the guidewire that passes through the leaflet to be used as a "rail" to drive the delivery catheter over, by sliding the inner tubular member over the ends of the guidewire. The lumen of the inner tubular member can be provided with a sufficient diameter to permit as many as six guidewires to pass through in the event that three leaflets are captured, such as in the case of the tricuspid valve. It will be appreciated that the procedure of FIG. 19A can be reproduced for each of one, two or three leaflets on the same valve. Both ends of the guidewires can be externalized. If desired, a loop can be formed on the proximal end of one or more of the guidewires, and the distal end of the guidewire can be threaded through the loop, and the resulting knot can be pushed down to the leaflet to permit for the inner tubular member of the catheter of FIG. 20 to only need to accommodate three guidewires therethrough instead of six. An intermediate tubular member can be slidably received over the inner tubular member inside of the outer tubular member that includes one, two or three loops mounted at the distal end of the intermediate tubular member. One or more of these loops can be coupled to an electrical power source (RF) at a proximal end of the intermediate tubular member by way of one or more electrical conductors that traverse the length of the intermediate tubular member.

Figure 20A:
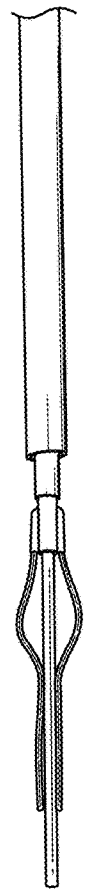
Figure 20B:
Figure 20C:
Figure 20D:
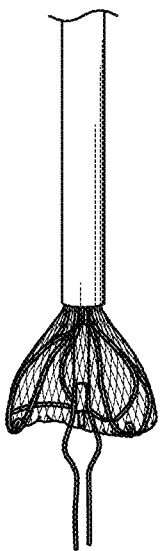

As shown, each loop is coupled at a proximal end to the distal end of the intermediate tubular member by any one of a number of suitable techniques. The wire of each respective loop then travels in a distal direction and completes its path in a loop shape. For example, a loop can be formed from a strand of insulated or uninsulated wire with two proximal ends that can complete an electrical circuit by running electricity along its length. The proximal portions of the loops that extend distally can also be provided with a radially outwardly extending bend such that the wires of the loops first extend radially outwardly, and bend to then extend radially inwardly, to permit the outer tubular member of the delivery system to ramp up on the wires as they bend outwardly so as to impart a radially inward force on the loop or loops to cause the loops to bend inward radially, and grasp and urge against a valve leaflet. FIG. 20D illustrates a side view with the inner tubular member retracted proximally.

FIGS. 21A-21E illustrate the aforementioned system for cutting tissue utilizing a guidewire as described herein as a rail. In one embodiment, a single leaflet system can be advanced over both ends of an electrified guidewire that has been directed through the leaflet as described above in FIG. 19 approximately one third of the way from the edge of the leaflet. FIG. 21B illustrates how the guidewire lumen, or inner tubular member, can be advanced down to the edge of the leaflet and temporarily secured. FIG. 21C illustrates how, while the guidewire lumen is secured against the leaflet, the cutting head can be advanced with the leaflet between cutting elements. With reference to FIG. 21D, once the loop shaped cutting elements are in place, the outer tubular member is then advanced distally over the radially outwardly directed angled points of the loops to press the loops toward each other on other side of the leaflet to create firm pressure against the leaflet. At this point, the cutting elements can be electrified to cut the leaflet and retract the cut portion into the delivery catheter for removal.

FIGS. 22A, 22B, and 22C illustrate examples of differently shaped cutting wires that can be mounted on the distal end of the intermediate tubular member of FIG. 20, wherein one of each pairs of loops is covered in electrical insulation. FIG. 22A illustrates a round loop having a larger removal area. FIG. 22B shows diamond shaped loops, which may facilitate withdrawal of the loops into the delivery catheter, and FIG. 22C depicts oval shaped loops that are smaller in transverse extent than the loops of FIGS. 22A and 22B.

Figure 23A:
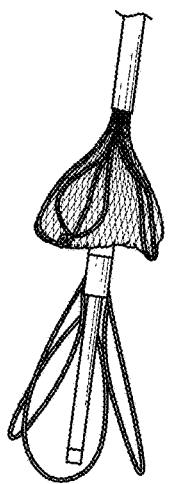
Figure 23B:
Figure 23C:
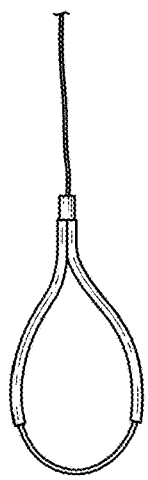
Figure 24A:
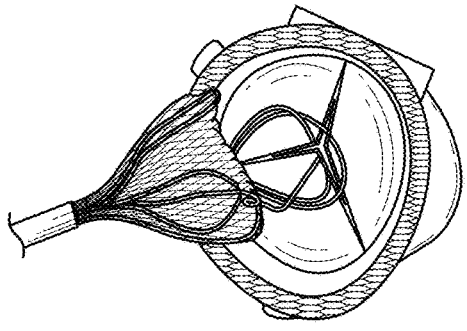
Figure 24B:
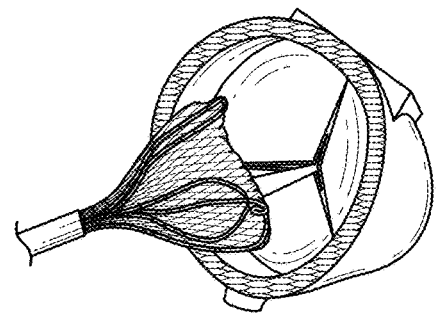
Figure 24C:
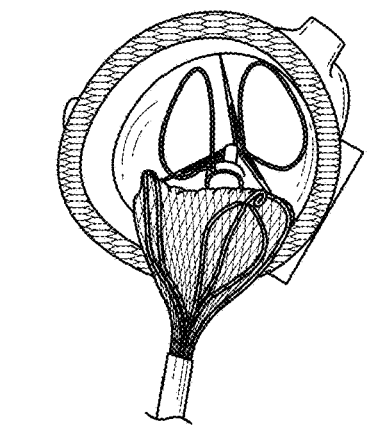
Figure 24D:
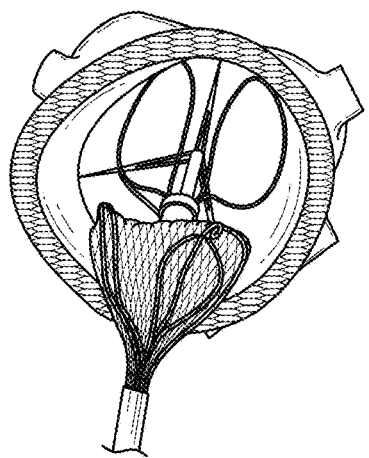

FIGS. 23A-23C depict a similar catheter to that of FIG. 20, but with two electrically exposed cutting loops, used in combination with two crossing guidewires, each being delivered to a separate leaflet using the technique of FIG. 19, and FIGS. 22A-24C depict an embodiment with three cutting loops to cut three leaflets, each of which is similarly captured by a guidewire. However, the loops are configured to splay radially outwardly so their distal end regions can extend out radially to reach the valve annulus. As with the previous embodiments, an inner tubular member of the catheter is threaded along the guidewire(s) passing through the leaflet(s). The cutting loops are advanced distally toward the leaflets and they are configured to splay radially outwardly, so that they contact the valve leaflet near the wall of the vessel. The distal regions of the loops are denuded, such that when they are electrified with RF energy they cut through the leaflets near the valve annulus, preferably in a non-calcified region, and the catheter and electrified loops are rotated about a central axis of the catheter to effectuate the cutting. The routing of the guidewire through each respective leaflet will thus allow for removal of the cut portion of the leaflet after cutting. Insulated portions of the cutting loops will protect and prevent any non-desired portion of the leaflets from being cut.

Figure 26D:
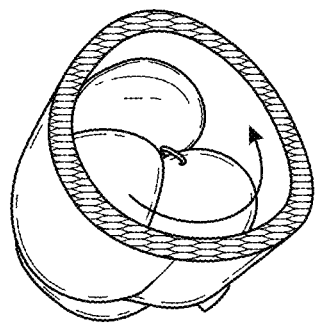
Figure 26C:
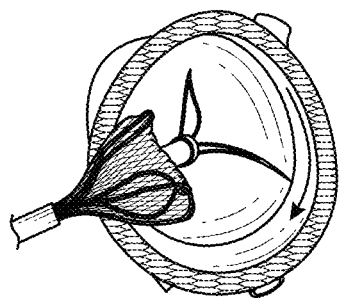
Figure 26B:
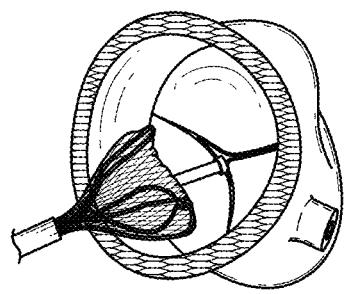
Figure 26A:
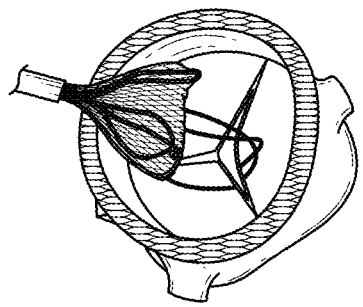

FIGS. 25A-26D illustrate an implementation with a rotary blade to cut one or more leaflets with a protection basket to capture cut portions of leaflets and prevent emboli. These embodiments are preferably used by capturing each respective leaflet using a guidewire as described above. In this embodiment, the inner tubular member and outer tubular members are essentially the same as the previous embodiment, except that the intermediate tubular member includes a laterally offset blade attached at its distal end that can trace out an annular cutting path when the intermediate tubular member is rotated about the inner member in the valve annulus area. The inner tubular member is once again used to advance the cutting device to the edge of the leaflet over the guidewire rail. A guidewire lumen stopper can be provided at a distal end of the inner tubular member that will restrict the cutting blade from advancing too far through the valve. The rotary cutting blade attached to the intermediate tubular member can be sharpened on one or both sides making it bi-direction. The rotary cutting blade can be electrified with RF energy. The placement of the guidewire can then ensure that the removed section of the leaflet is removed by removing the guidewire that is routed through that portion of the leaflet. Thus, FIG. 26D includes leaflet crossing guidewires to be used as a rail for the leaflet removal device. FIG. 26B illustrates the guidewire lumen placed at the leaflet edges bringing them together. FIG. 26C illustrates advancement of the cutting blade over the inner tubular member that defines the guidewire lumen up to the end stopper, between or through the leaflet. The blade can be rotated to cut through two leaflets. FIG. 26D depicts a view from underneath the advanced cutting blade which can rotate to cut through the two leaflets.

FIGS. 27-72 illustrate examples of further embodiments to carry out procedures also described elsewhere in the present application.

Figure 27:
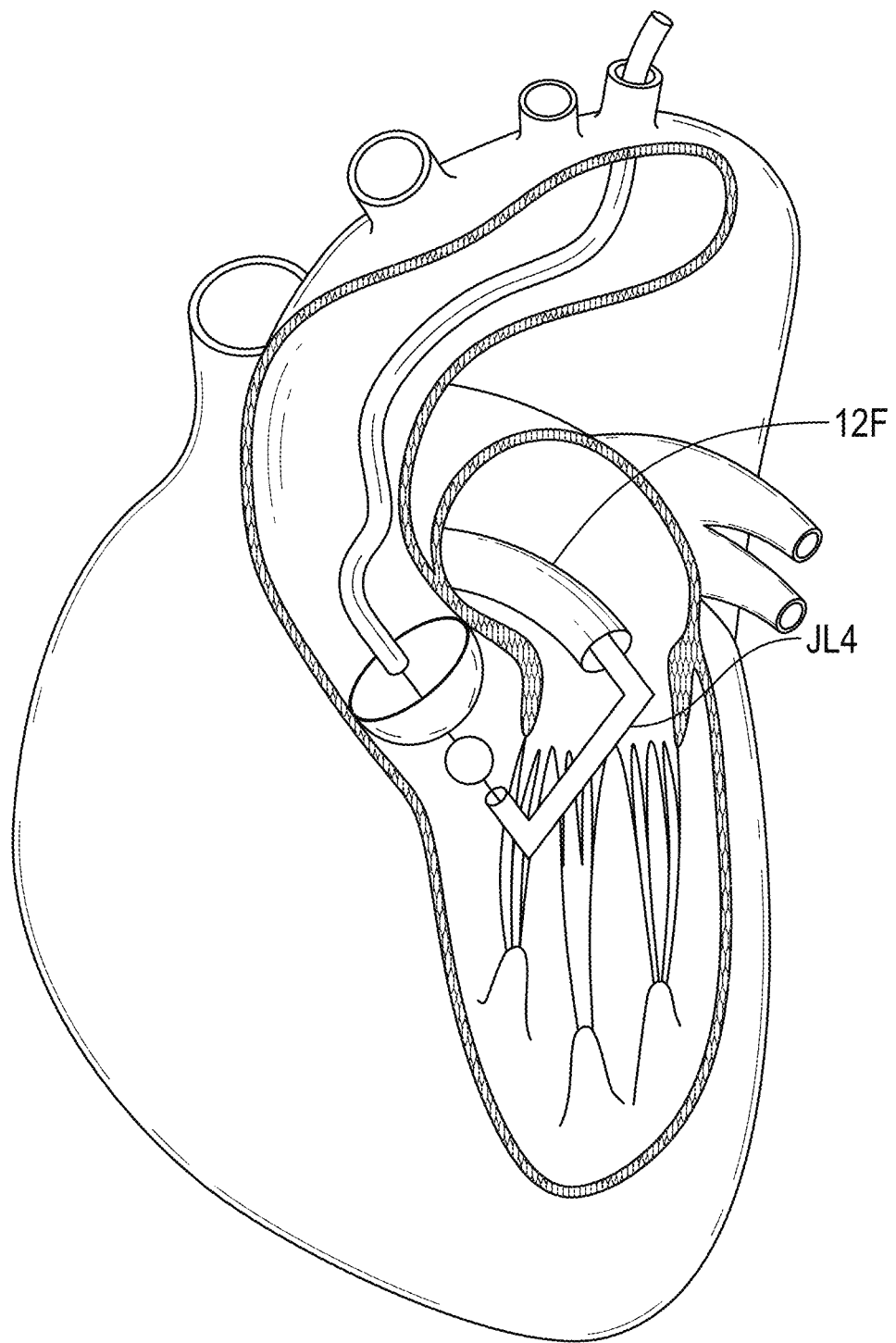
Figure 28:
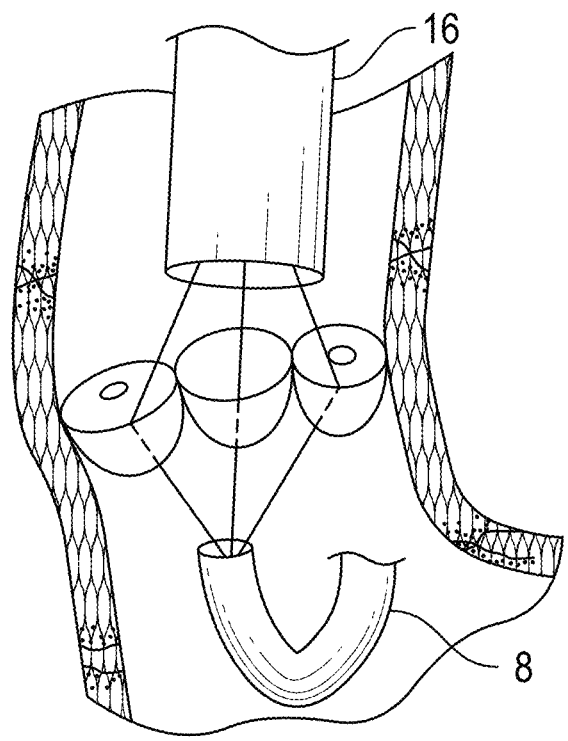
Figure 29:
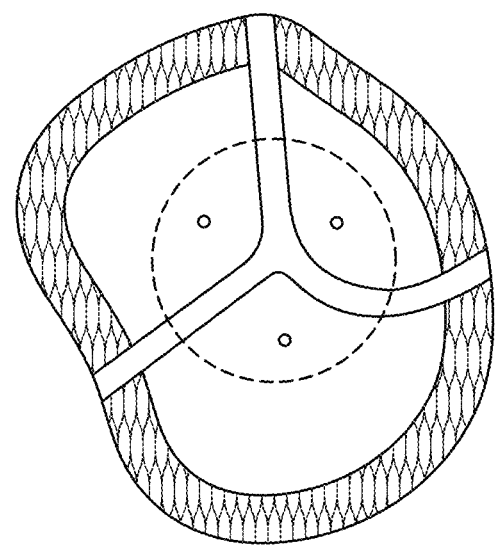
Figure 30:
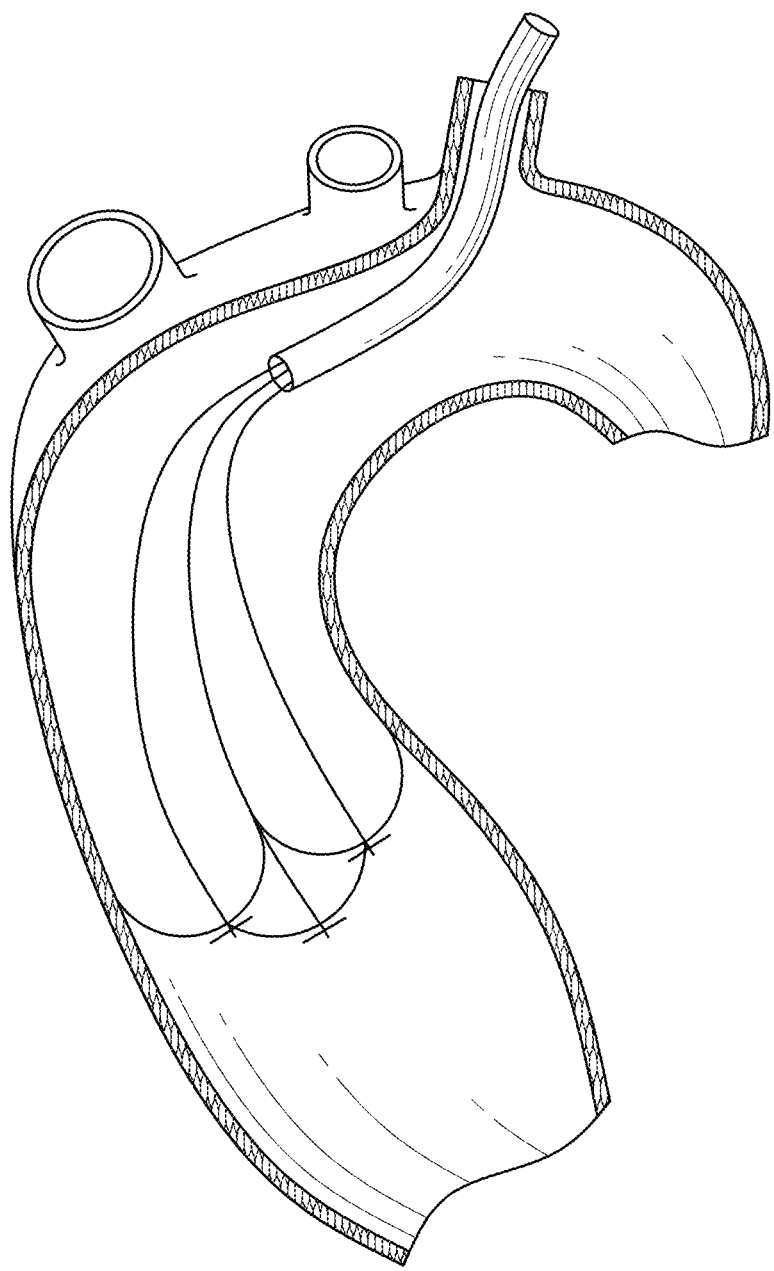
Figure 31:
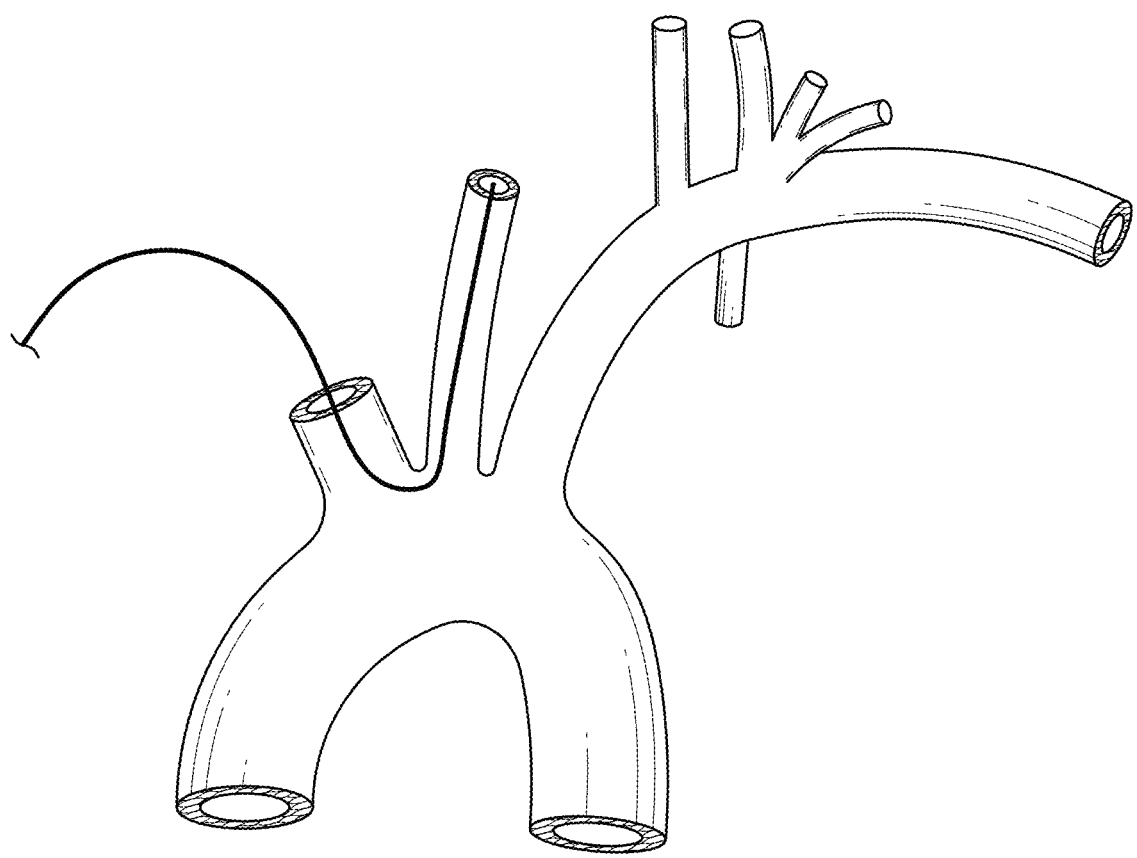

FIG. 27 depicts a first step of a procedure wherein a pachyderm guide catheter is introduced to a target location proximate a tricuspid valve along with a flexible catheter and a JL4 catheter, which is a standard left coronary ostium access catheter, with JL being an abbreviation for Judkins left. Its curve allows for easy placement into the left coronary ostium. A 16Fr ablation catheter (FIG. 28) can then be used to traverse each of three leaflets in the valve. Tethers from the traversal can be anchored to each leaflet using knots and pledgets as desired (FIGS. 29-30). With reference to FIG. 31, a previously installed Sentinel embolic protection catheter is removed.

Figure 32:
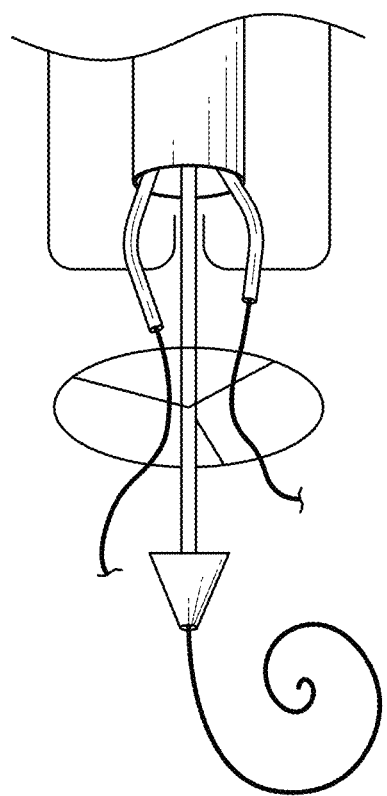
Figure 33:
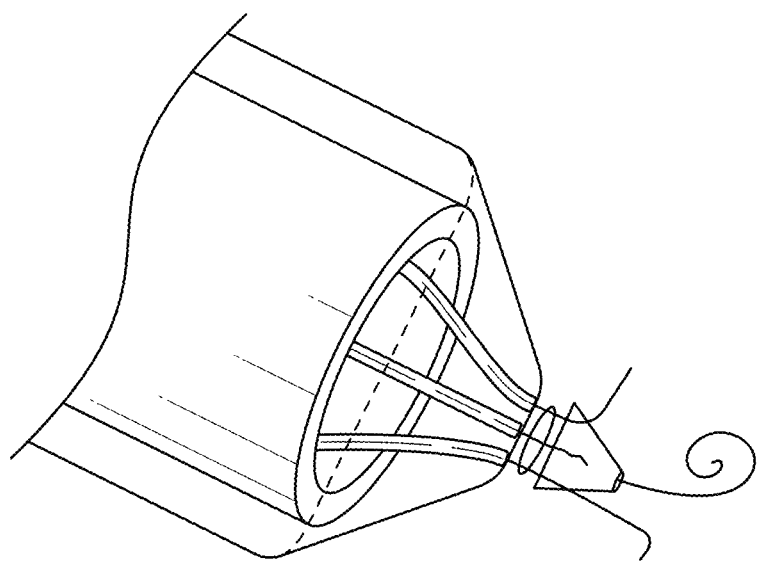
Figure 34:
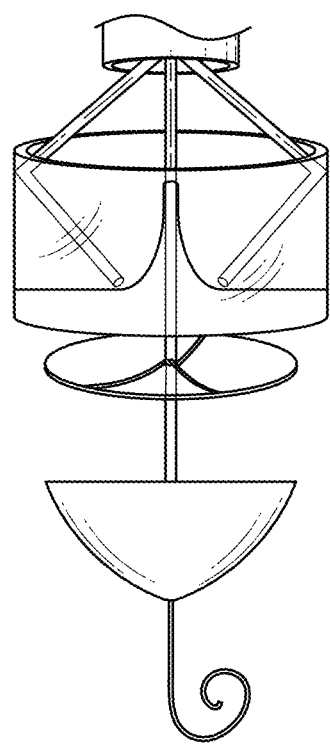

FIGS. 32-33 depicts a system including a guiding catheter including a plurality of tubular members, each of which includes a 0.014-inch guidewire having an exposed distal tip that can be electrified to traverse a respective valve leaflet. The catheter system can further include a central stylet with a nose cone configured to receive a 0.035-inch wire therethrough. Each of the tubular members can be angled inside a stent frame (FIG. 34) of an associated TAVR valve that is installed after the leaflets are cut out of the way.

Figure 35:
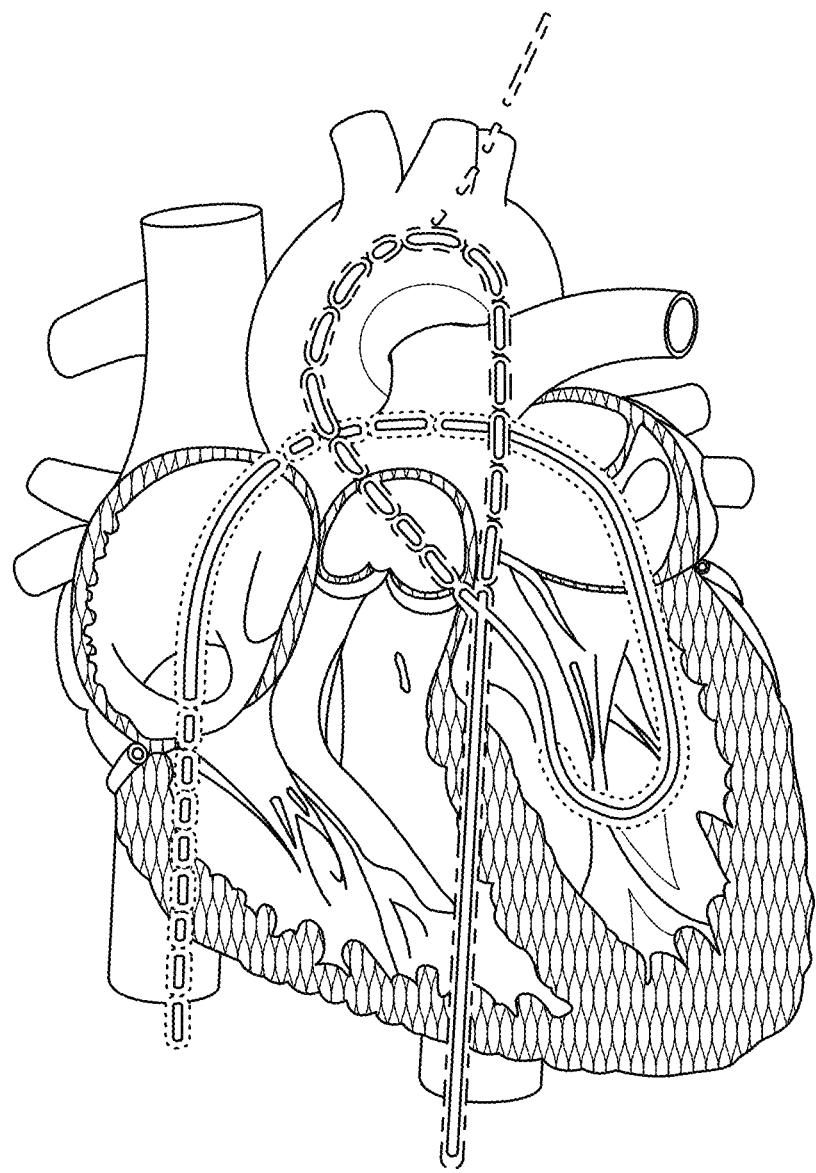

FIG. 35 depicts an introduction path of a guiding catheter that is introduced by way of the IVC into the heart, and a second catheter that is introduced to the aorta by way of femoral access. These access paths can be used to deploy catheter systems for leaflet and tissue excision for an aortic valve illustrated in FIGS. 36-57 by introducing a guidewire along the path of both catheters, completing the path. An elongate distal portion of an inner tubular member of the system is then introduced along the entire path over the guidewire.

Figure 37:
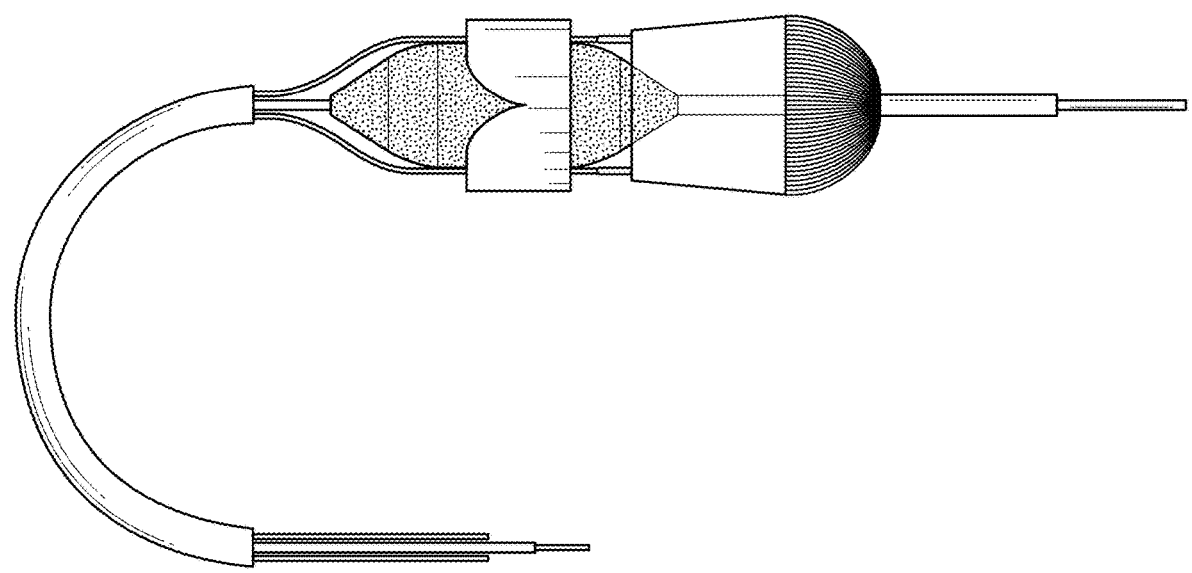

After the distal portion of the inner tubular member is introduced, the remainder of the system is deployed by advancing an outer catheter of the system past the aortic valve, and retracting the outer tubular member proximally. First, a distalmost capture basket is deployed that occupies space on a downstream side of the aortic valve. This inner basket is attached to the remainder of the system by three conductors coupled to an open rim of the basket, wherein the basket self-expands and is made, for example, of a shape memory material so as to occupy the width of the aorta downstream of the aortic valve. As the outer catheter is retracted proximally, a self-expanding inner basket expands that is attached to the inner tubular member. This inner basket may be used as one pole of a bipolar electrosurgical system, or as an expansion mechanism. The inner basket expands to occupy the aortic valve. The electrosurgical cutting edge is defined on a proximally facing circumferential ridge of the capture basket. The capture basket is energized by energizing the three leads that are coupled to the annular rim of the capture basket, and the capture basket is pulled into the cusps of the aortic valve by pulling on the leads in a proximal direction. If bipolar current is used, the circuit is completed by crossing a gap through the aortic valve leaflets to the inner basket. The basket eventually is pulled proximally enough to surround the inner basket, wherein the inner basket and outer basket cooperate with the inner tubular member of the system to define an annular cavity to collect the severed aortic valve anatomy and debris, trapping the severed materials. As depicted in FIG. 37, the distal end of the inner basket terminates in a Coanda tip shape that extends into the capture basket that enhances flow into the center of the basket and through the system generally so as to permit perfusion. The capture basket can be configured to be detached from the venous access device after the valve leaflets have been captured, or it may be withdrawn into the introduction catheter.

Figure 36:
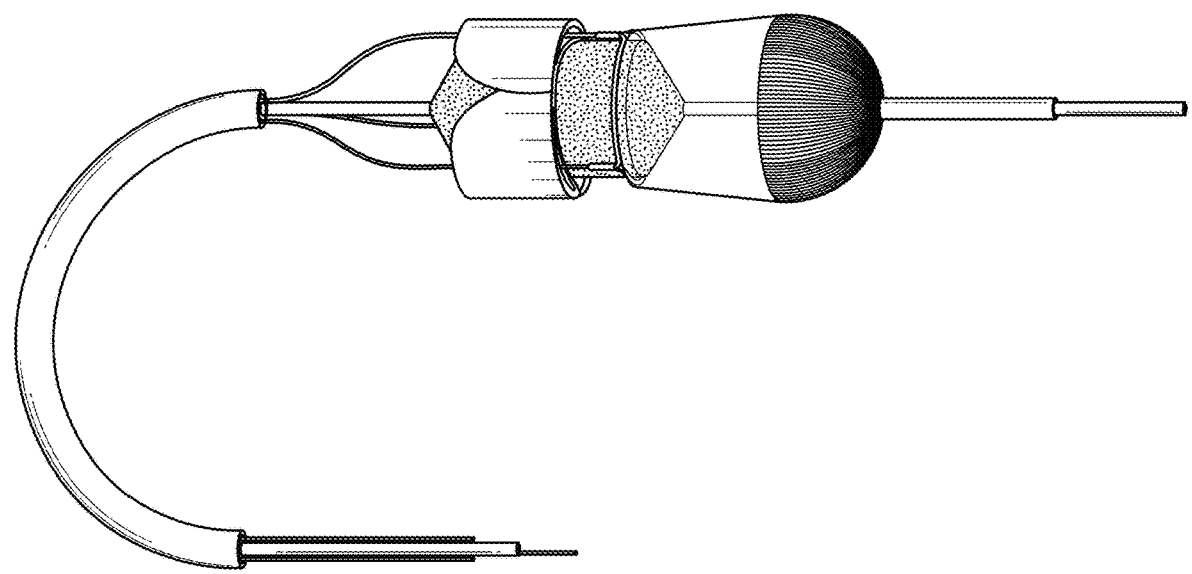
Figure 38:
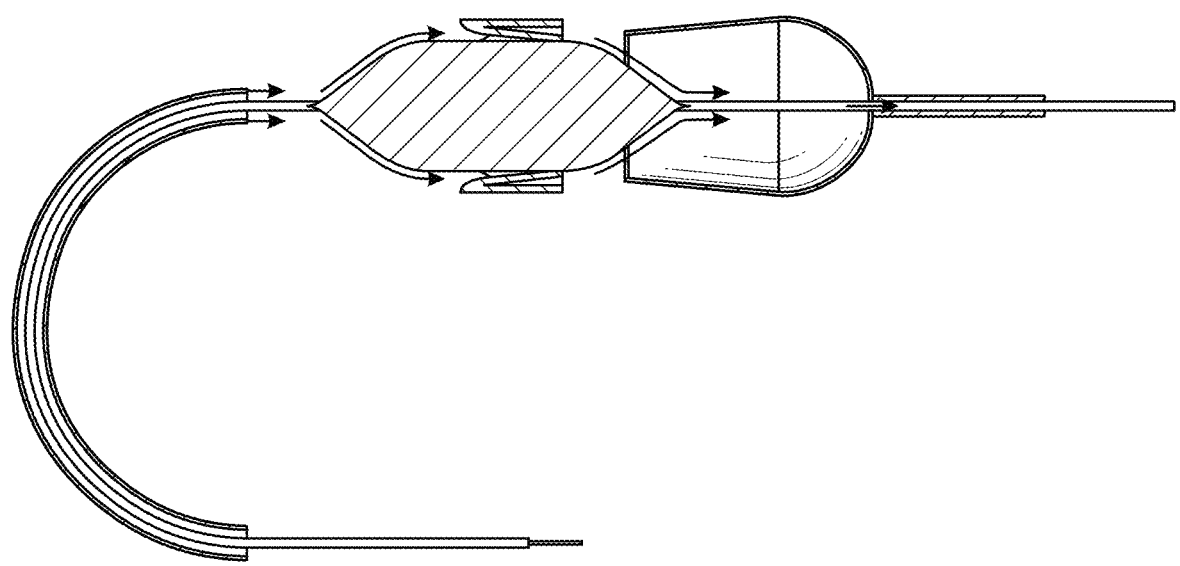
Figure 43:
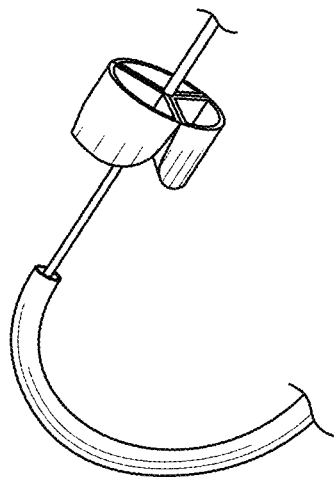
Figure 44:
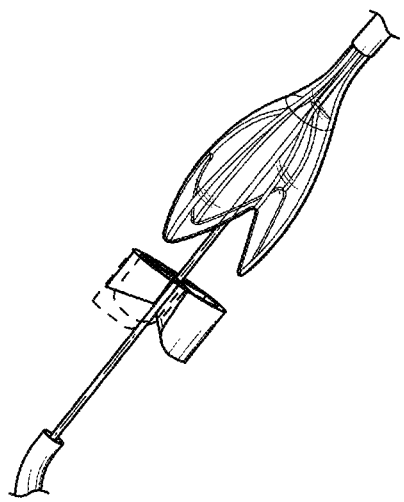
Figure 45:
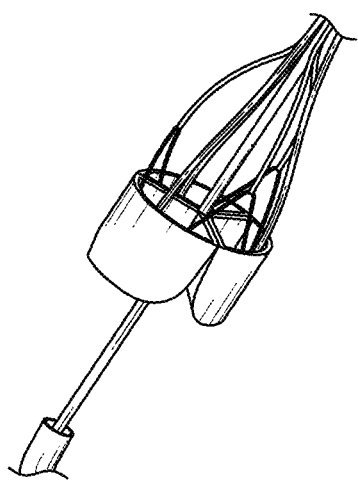
Figure 46:
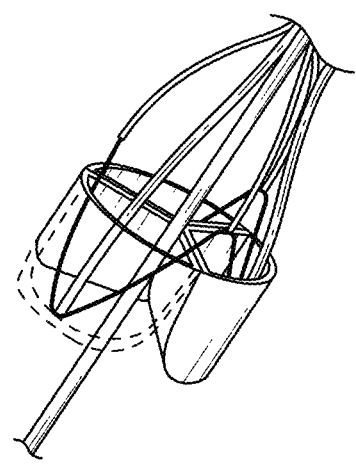
Figure 47:
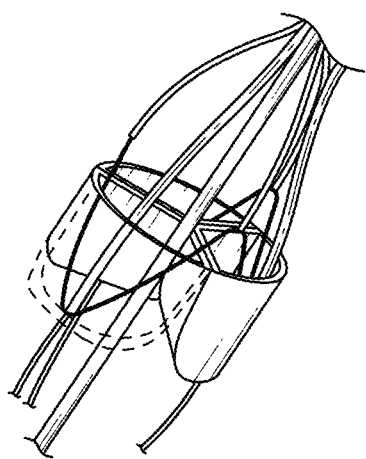
Figure 48:
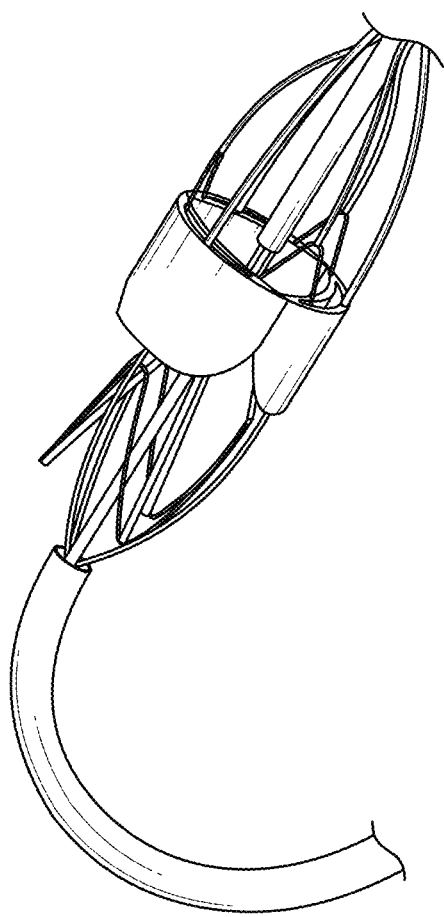
Figure 49:
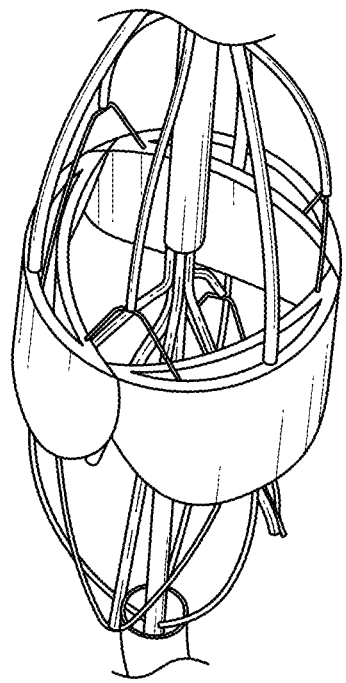
Figure 50:
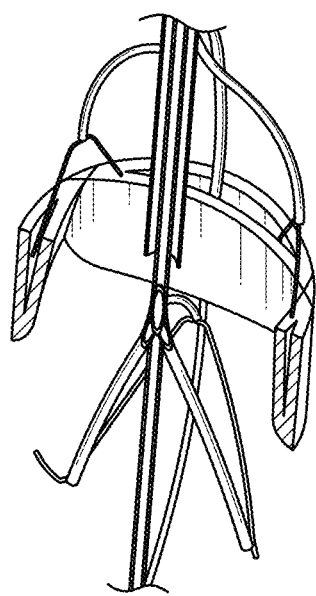
Figure 51:
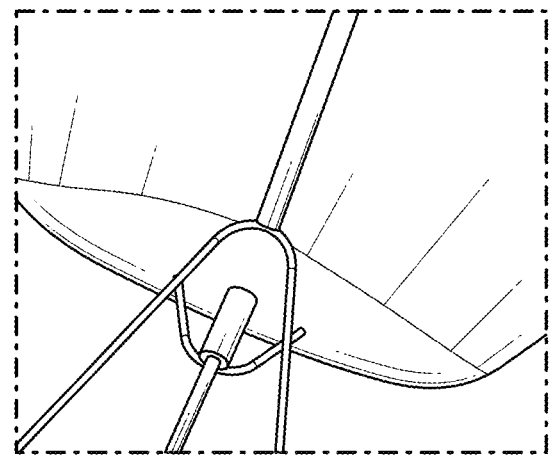
Figure 52:
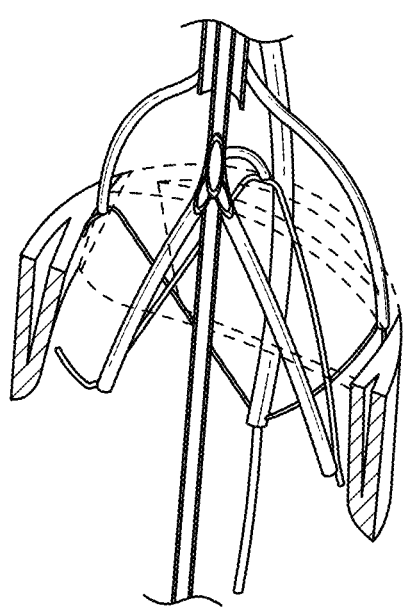
Figure 53:
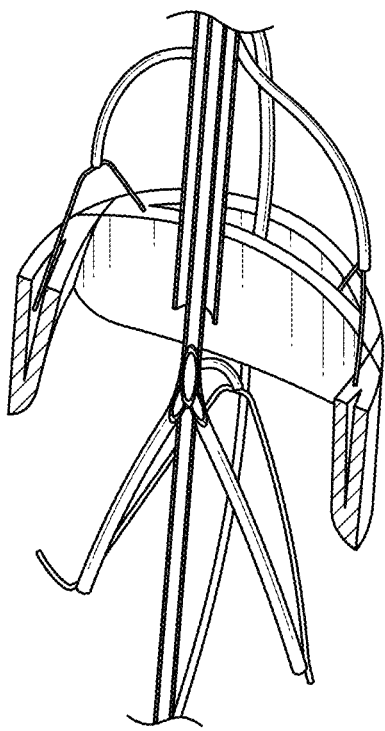
Figure 54:
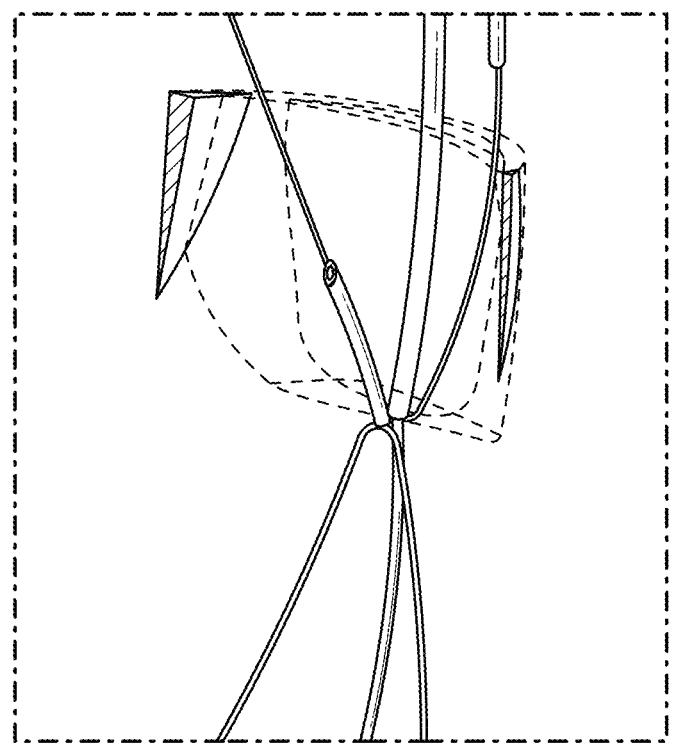
Figure 55:
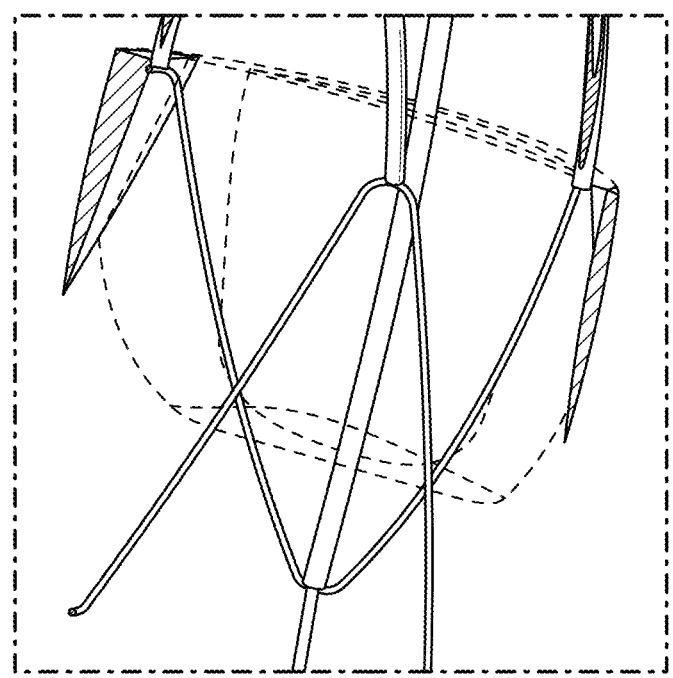
Figure 56:
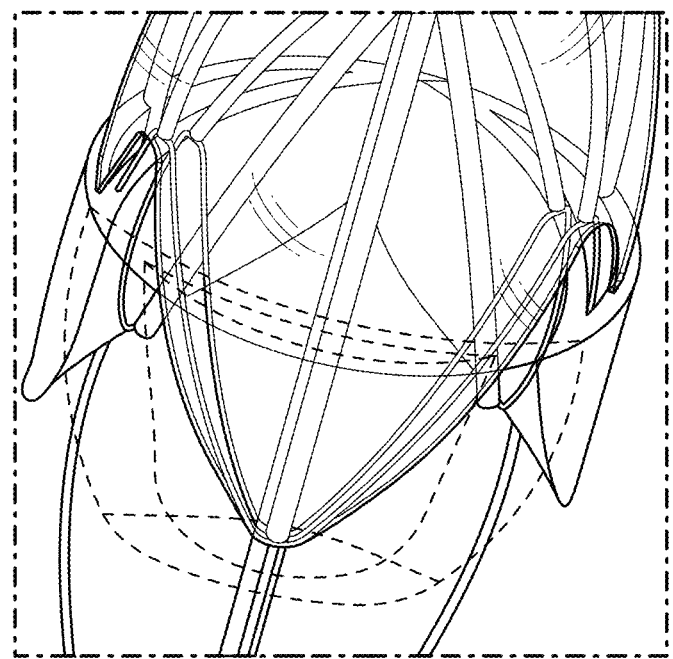
Figure 57:
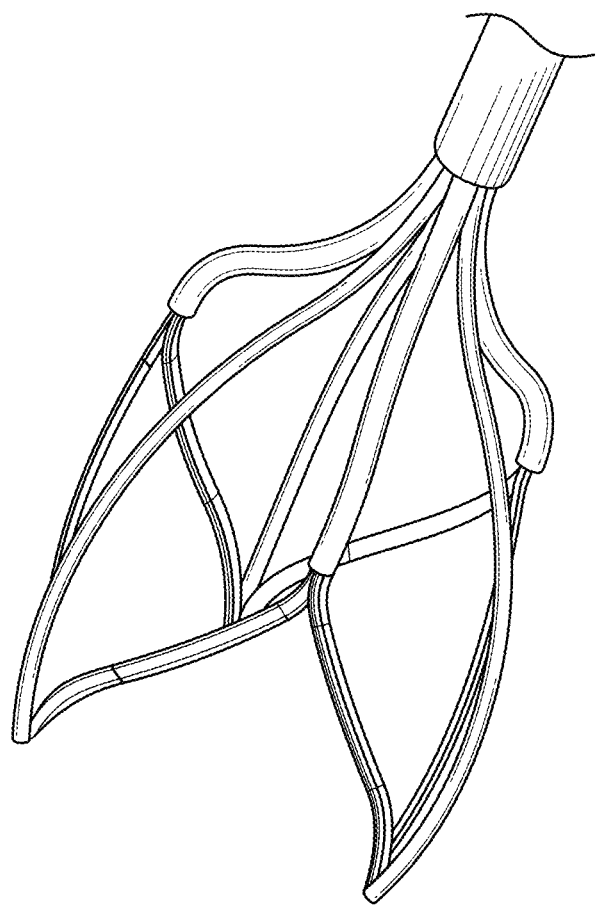
Figure 58:
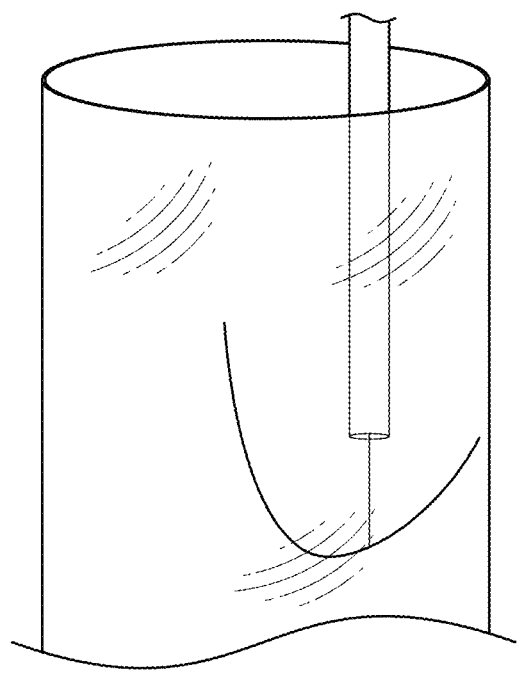

FIGS. 39-42 depict a variation of the system of FIGS. 36-38 that replaces the distal capture basket with one having a dual concentric electrode assembly, wherein an outer electrode (FIG. 40) includes three proximally facing tips to be received within the cusps of the aortic valve located radially outwardly from the leaflets of the aortic valve. An inner electrode (FIG. 42) can be disposed either concentrically within the outer electrode and be attached to the distal assembly, or be disposed on the distal end of the inner basket of FIGS. 36-38 that is introduced into the aortic valve inside the valve leaflets. A circuit is completed between the inner and outer electrodes through the tissue of the valve leaflets. The inner and outer electrodes are advanced proximally as they burn through the tissue. The outer electrode can have a zig zag leading edge that can be rotationally aligned or displaced from the sig zag electrodes of the inner electrode. The arc is completed by the shortest path of travel between the inner and outer electrodes in a bipolar arrangement (FIG. 55). A monopolar arrangement can be effectuated (FIG. 56) by aligning the inner and outer electrodes and completing the circuit through the patient to cut the leaflet material. The outer electrode can be powered by three electrical leads as depicted extending from the proximal end of the device through the IVC path. If desired and as depicted in FIG. 57, the outer electrode can include mechanical cutting edges to help cut through the tissue as the outer electrode is advanced along a proximal direction.

Figure 59:
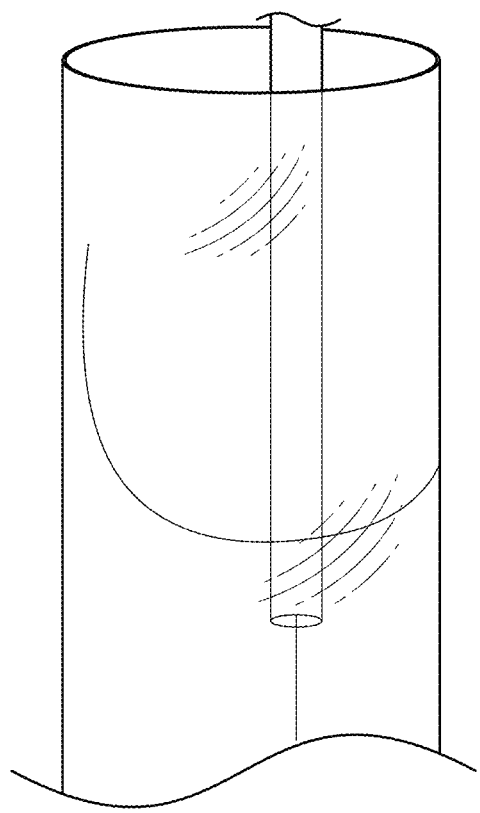
Figure 60:
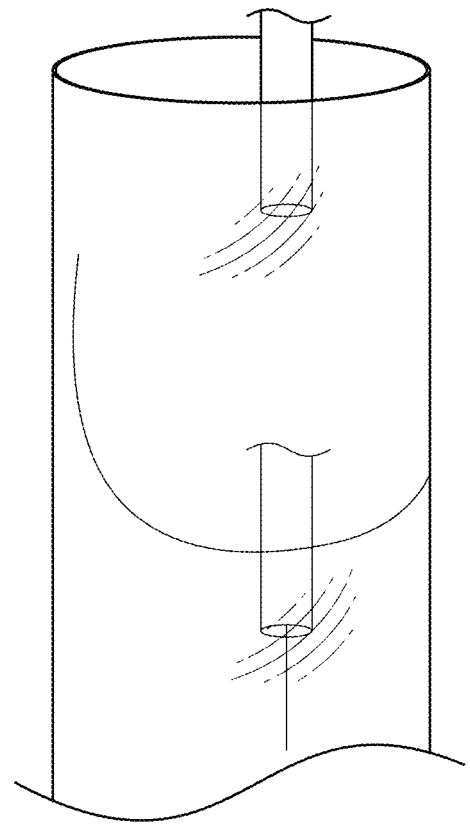
Figure 61:
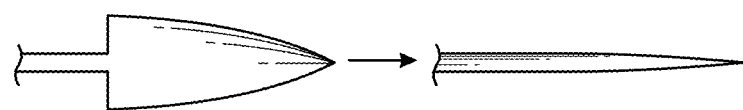
Figure 62:
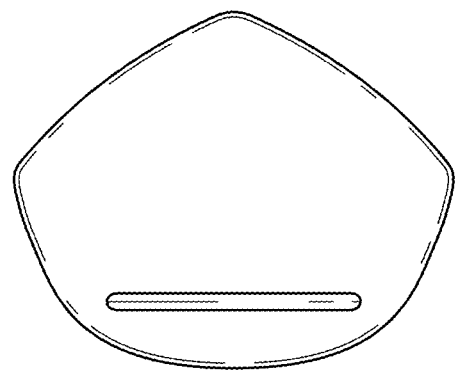
Figure 63:
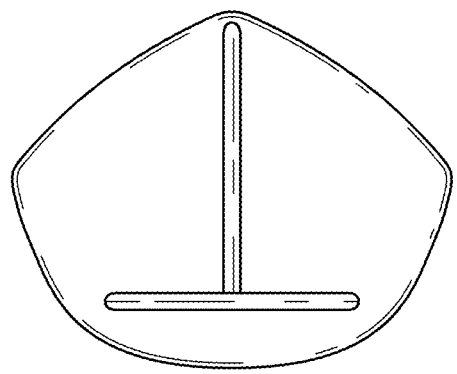

FIGS. 58-72 depict a further leaflet cutting catheter that can be deployed in a "T" shape so as to facilitate making a lateral cut through a valve leaflet. To illustrate this procedure, with reference to FIG. 58, in a first step, a catheter is positioned with a guidewire tip at a desired location of the leaflet. The guidewire is electrified and burned through the leaflet. With reference to FIG. 59, the opening is further traversed by a microcatheter to enlarge the hole in the leaflet. Or, it is also possible to have a dilatation tip on the catheter. With reference to FIG. 60, the "T" is advanced out of the distal tubular end of the catheter attached to an inner catheter having an inner and an outer member with the lacerator in a collapsed elongated position past the leaflet. Next, the lacerator is deployed by withdrawing an inner portion of the lacerator connected to the tip with respect to an outer tubular member of the lacerator. The lacerator is then positioned at the bottom of the leaflet in the desired orientation. The lacerator is then electrified and pulled back to cut through the leaflet. With reference to FIG. 61, the wires of the T-lacerator can be doubled with joints to allow it to collapse easier. The wires of the T-lacerator are insulated except for the exposed or denuded area of wires that are electrified and used to cut through tissue. With reference to FIG. 62, once the first cut is made at the base of the leaflet, the T-lacerator can be re collapsed, re-advanced over the guidewire and re positioned below the leaflet again. The T-lacerator can then be re-opened and positioned orthogonal to the first cut. With reference to FIG. 63, the T lacerator is electrified and at a second longitudinal cut is made in the leaflet. T-shaped lacerations can be accomplished in the aortic leaflet and allows the coronary ostium to be free of obstruction for subsequent TAVR.

Figure 64:
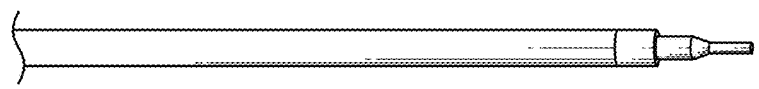
Figure 65:
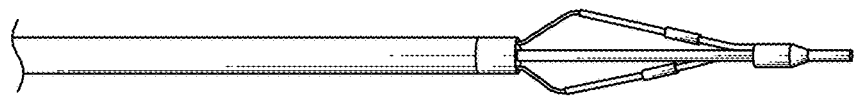
Figure 66:
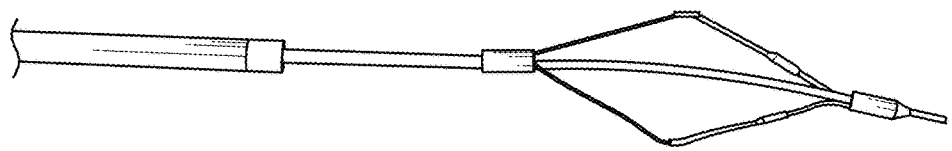
Figure 67:
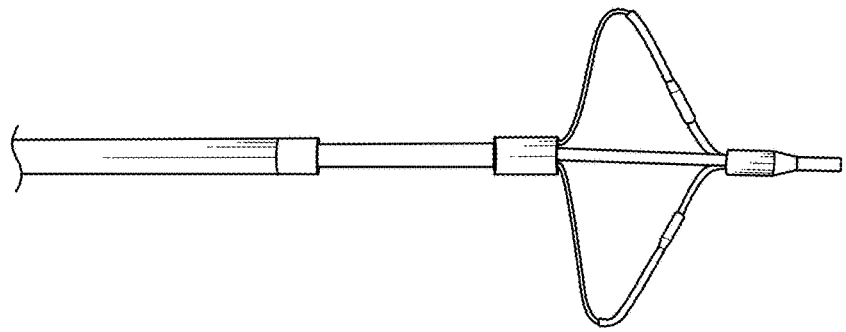
Figure 68:
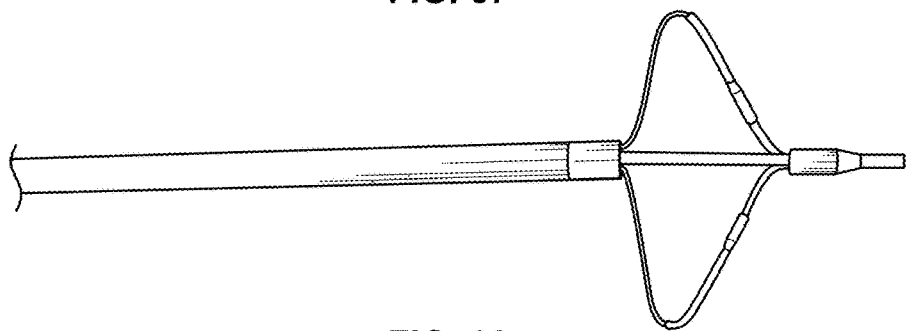
Figure 69:
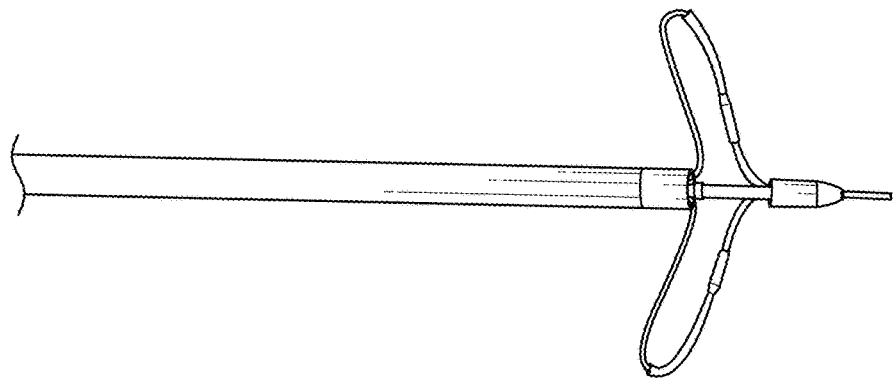
Figure 70:
Figure 71:
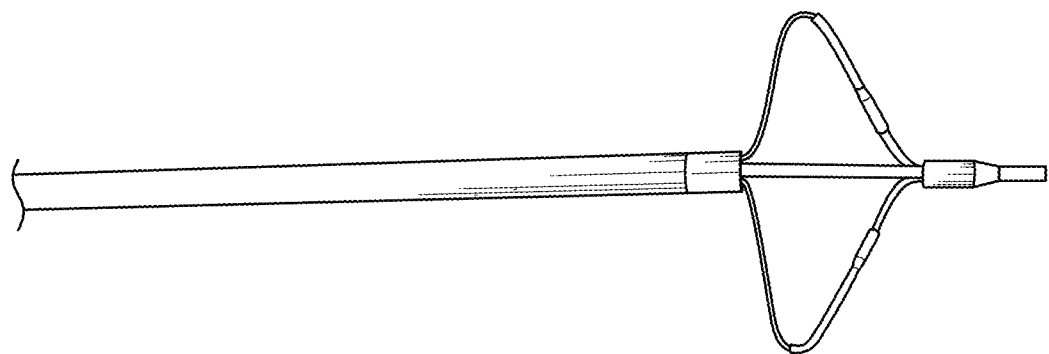
Figure 72:
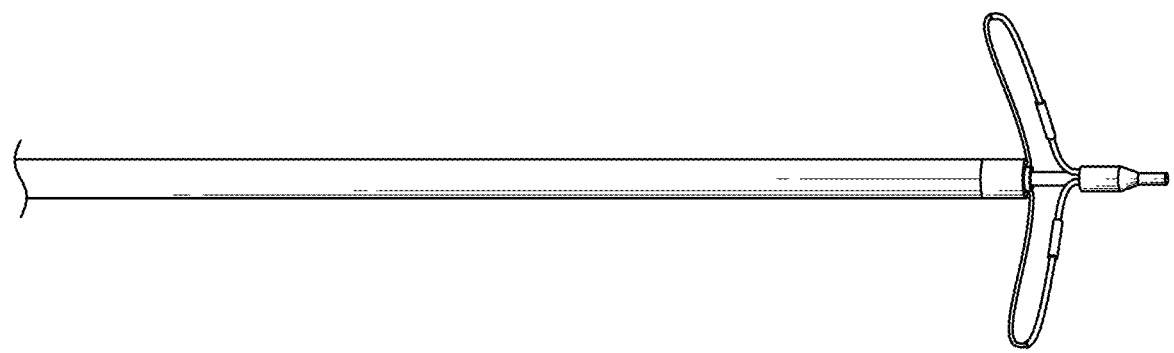

FIG. 64 depicts the T-lacerator in a collapsed position, showing the outer shaft. FIG. 65 depicts a dilator tip with a guidewire lumen that has a good transition in stiffness between the guidewire and the T lacerator. FIG. 66 depicts an inner shaft and guidewire lumen that is connected to the distal tip of the T lacerator, and an intermediate tubular member coupled at a distal end to the proximal end of the cutting portion, such that pulling the tip proximally with respect to the intermediate member causes the T-lacerator to deploy. FIG. 67 depicts the T-lacerator in an open or deployed position. FIG. 68 illustrates exposed denuded wires on the proximally facing deployed surfaces of the T-lacerator. FIG. 69 depicts an inner shaft pulled back against the outer shaft to further collapse the cutting wires to make them stiffer. FIG. 70 depicts the collapsed position of the catheter showing the dilator tip with guidewire lumen; the wires of the inner shaft; and the outer shaft. FIG. 71 depicts the device in a partially deployed position illustrating exposed wires and the central guidewire lumen, whereas FIG. 72 depicts the device in a fully deployed configuration. It will be appreciated that while a single circuit is depicted that passes through the entire T-lacerator, it is possible to have a plurality of wires that form the lacerator that are electrically isolated from each other.

FIGS. 73A-93 Illustrate various techniques for repairing or adjusting the performance of luminal valves, such as (but not limited to) procedures for transcatheter tri-leaflet tricuspid repair. It will be appreciated that the disclosed devices and techniques can be used on any valve structure having leaflets. The below illustrative description is not intended to be limiting. Rather, this description is intended to present particular non-limiting implementations. Thus, disclosed in this embodiment are methods of repairing or adjusting the performance of a valve structure as described and devices for repairing or adjusting the performance of a valve structure as described.

Disclosed are low profile transvenous access systems (e.g. compatible with an 18F or greater introducer sheath) in the form of a transfemoral venous system. The system can use multi-axial deflectable guiding sheaths that has two or more coaxial shafts that are deflectable, an outer shaft to navigate through the inferior vena cava to the right atrium and then through the tricuspid valve having, for example, a 10F outer diameter and a 100 cm effective length. The system can further include an inner shaft to navigate to the apical surface of the leaflets having, for example, an 8F outer diameter and about a 110 cm effective length. The system further includes a leaflet traversal tool to cross through the leaflets from the apical side to the atrial side. The traversal tool can, for example, include an 0.014" outer diameter guidewire, utilize the transmission of radiofrequency (RF) energy to electrify the length of the traversal tool, have an electrically insulative polymer coating along the effective length, except for at the distal tip to delivery energy to the leaflet tissue to aid in traversing the tissue. At the proximal end the guidewire connects to a RF generator. The guidewire preferably has, for example, a 300 cm effective length, an electrosurgical connector to facilitate the connection between the leaflet traversal tool and the RF generator. The connector can be electrically shielded to deliver 5-60 Watts of RF energy through the effective length of the traversal tool, for example, have a spring-loaded mechanism to securely hold the electrified traversal tool in place, and be compatible with conventional electrosurgical generators, such as the Medtronic Valleylab FX.

The system further preferably includes a retrieval tool to deliver a device to snare the traversal tool, once it has crossed through the leaflet, in order to externalize it. The retrieval tool can have, for example, a 6F outer diameter, a snare to capture the traversal tool, such as a self-expanding, three-dimensional basket to allow for easy capture or a gooseneck-type snare for easy positioning on the atrial side of the leaflet. The system preferably includes a guidewire to suture "connector" to deliver a means of connecting the traversal tool with the radiopaque tension elements for their exchange. This connector should be easy and quick for physicians to engage, withstand high tensile forces (such as ~20 N per ISO 10555). Radiopaque tension elements can be delivered, such as radiopaque material loaded sutures, to exchange with the traversal wire to tension the regurged leaflets together. The radiopaque tension elements can be provided in a quantity of three independent elements, be non-absorbable, have mechanical and biological properties (tensile strength, strength retention, tissue reaction/thrombogenicity) similar to commercially available sutures, have different colors to help to identify individual leaflets during tension adjustment, and have a minimal length of 300 cm. The system should also include a radiopaque force-distribution element such as a pledget loaded with radiopaque material to prevent the tension elements from pulling-through the leaflets. The tension elements should have a foldable design feature to allow for easy delivery through the guide sheath, and be about 4×3 mm in size. Radiopaque and echogenic landmarks can also be provided for real-time image guidance to deliver the system, such as radiopaque marker bands and echogenic coils. These can be located, for example, at distal tips of the devices, and at specific increments along the length of the tension elements to aid in estimating distance.

The system is also preferably biocompatible per ISO 10993 and that has at least three points of apposition with tri-leaflets, delivering a system that deploys at least one tension element per leaflet. The system also preferably provides adjustable transcatheter suture fixation, and includes a mechanism that secures and maintains the tension delivered to all three leaflets by the tension elements. The transcatheter suture fixation can allow for secure and permanent fixation of the pledgeted suture tension elements. allow for adjustment of tension, reversal of tension, and full retrieval after application, be corrosion resistant, and be relatively easy to engage.

The system should also include a transcatheter suture cutter such as that provided in U.S. Pat. No. 10,433,962, which is incorporated by reference herein in its entirety for all purposes. Preferably, this device easily cuts through three sutures, and is corrosion resistant.

In accordance with the disclosure, the method can include placing a radiopaque suture through each leaflet, at least 0.5 cm to 1 cm away from the edge of the leaflet, with a radiopaque pledget on the apical side. The sutures can be tensioned together towards the center of the valve to reduce tricuspid regurgitation by effectively attaching the valve leaflets to each other. Then tension will then be maintained with a fastener, such as a lock as set forth in U.S. Pat. No. 10,433,962 that uses an associated lock delivery catheter.

Figure 73B:
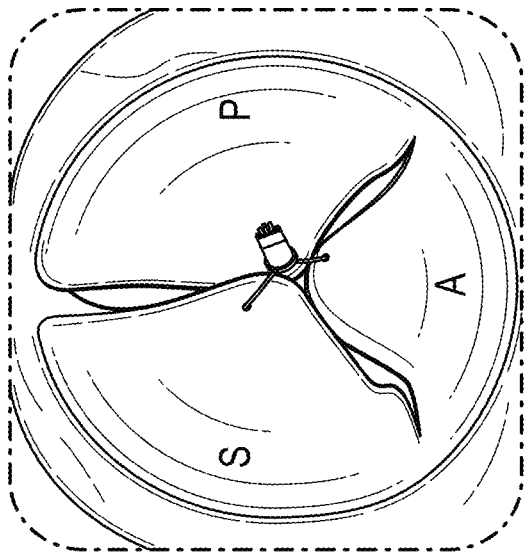
Figure 73C:
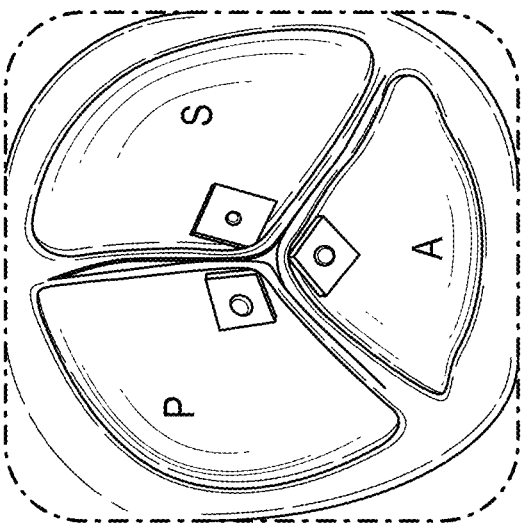
Figure 73A:
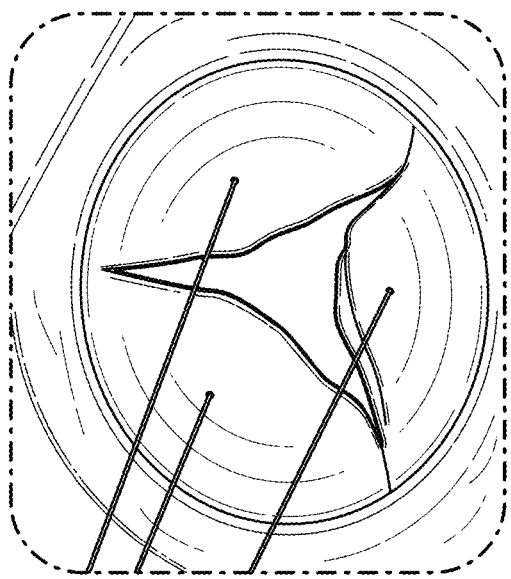

FIGS. 73A-73C depict the steps undertaken to effect transcatheter tri-leaflet tricuspid suture repair demonstrated in a benchtop, anatomical model of the tricuspid valve. FIG. 73A shows the tricuspid regurgitation model. FIGS. 73B and 73C respectively show the reduction of TR using three pledgeted sutures that are tensioned and locked together. FIG. 73C illustrates the apical side of the leaflets to display the pledgets that distribute the applied tension forces.

In further accordance with the disclosure, the profile of the disclosed devices within this system, and the interaction of multiple devices, can be compatible with a transfemoral introducer sheath through the right femoral vein. Multi-axial deflectable guiding sheaths can be provided. For example, a guide sheath can be used for ensuring that physicians can navigate to the necessary target sites. This guide sheath can have a minimum of two coaxial shafts that are each deflectable to provide 360° access in the tricuspid valve and around its leaflets at various radii. The outer shaft can have, for example, a 10F profile and a 100 cm effective length. The disclosed inner shaft can have, for example, an 8F profile and a 110 cm effective length.

FIGS. 74A-74B display an example of a distal end device. Specifically, a leaflet traversal tool can be used for navigating to the necessary target sites for this tri-leaflet repair procedure. Having a traversal tool, such as an electrified guidewire, allows for the puncture or crossing of the leaflets which facilitates the points of apposition necessary to reduce TR. Using radiofrequency energy transmission, one can use an 0.014" guidewire with a polymer coating (that has a high dielectric constant for insulating properties and a low friction coefficient for lubricity, for example PTFE) along the effective length of e.g., 300 cm, except at the distal tip (1-2 mm) and the proximal end (for connection into an RF generator). This electrified wire can be used to allow for transfemoral navigation up the IVC to the tricuspid valve, then can be electrified to puncture across the leaflets. The wire can be snared (using the retrieval tool, discussed below) and externalized back down the IVC to exit the transfemoral access sheath. For ease of navigation, this traversal wire can have mechanical properties similar to the Asahi Astato XS 20 or XS 40 guidewires.

Figure 75:
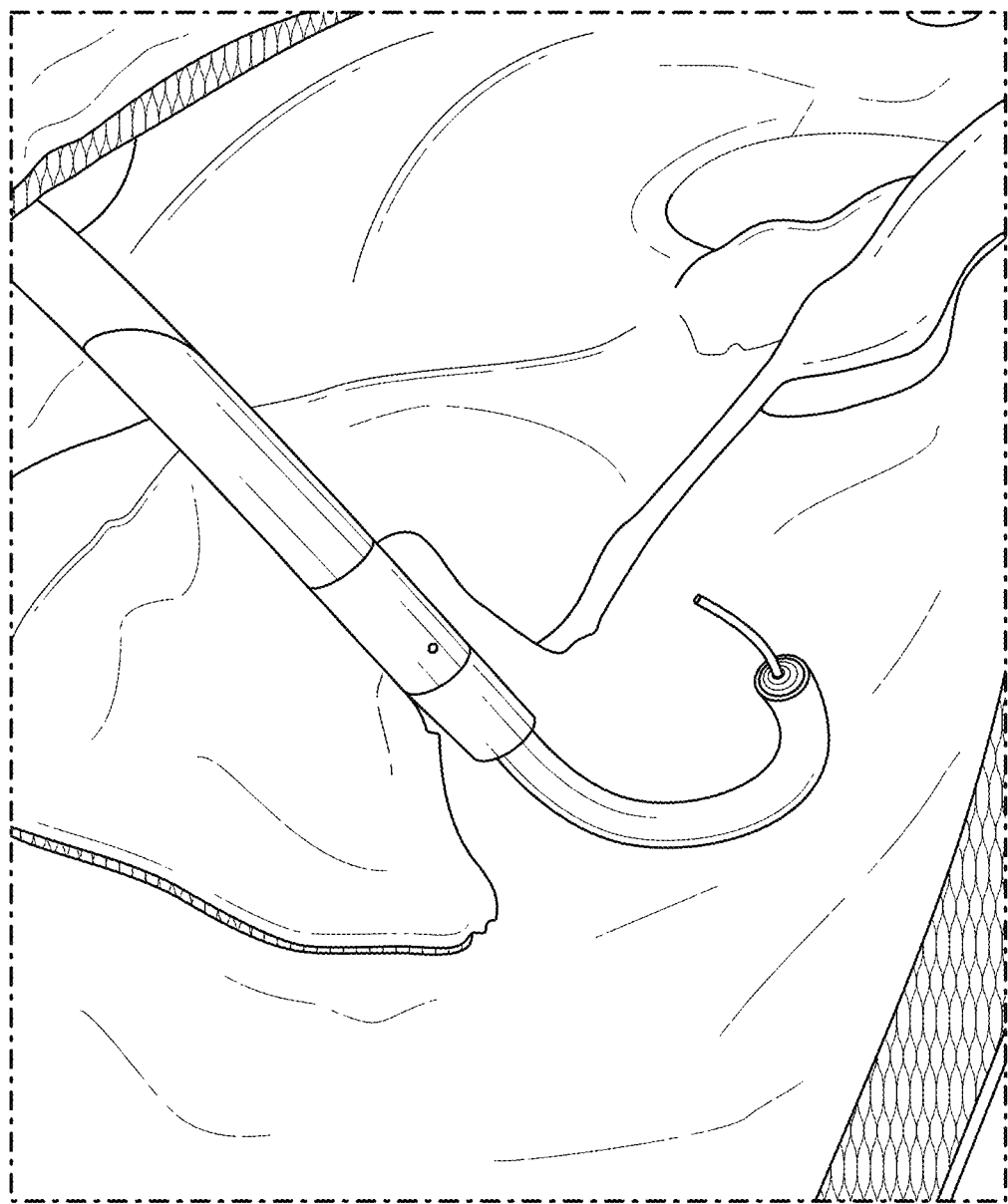

FIG. 75. Illustrates an electrified leaflet traversal tool traveling through the guide sheaths. In order to transmit RF energy from an RF generator to the traversal wire, an electrosurgical connector can be used. This connector can plug into the generator, such as a Medtronic Valleylab FX, with a RF compatible plug and then have a spring loaded, female connection for the exposed, proximal end of the traversal wire to ensure a secure connection between the two. The connector can be electrically shielded to deliver 5-60 Watts of RF energy through the length of the traversal wire to the exposed distal tip.

Figure 76A:
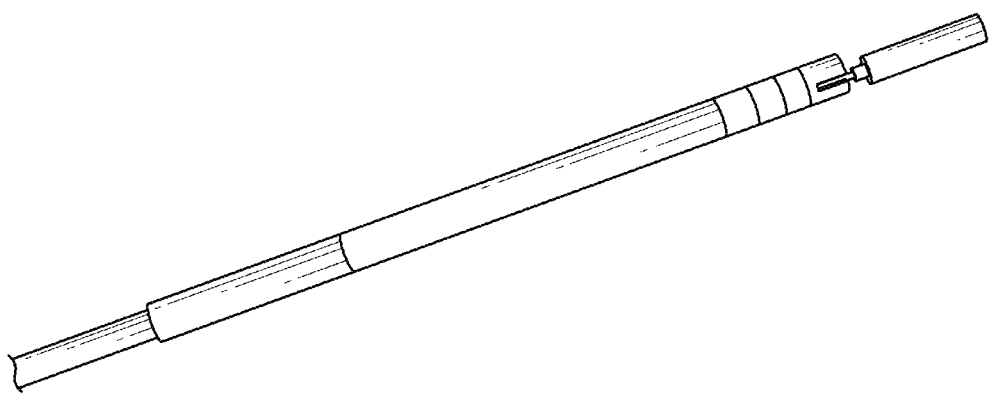
Figure 76B:
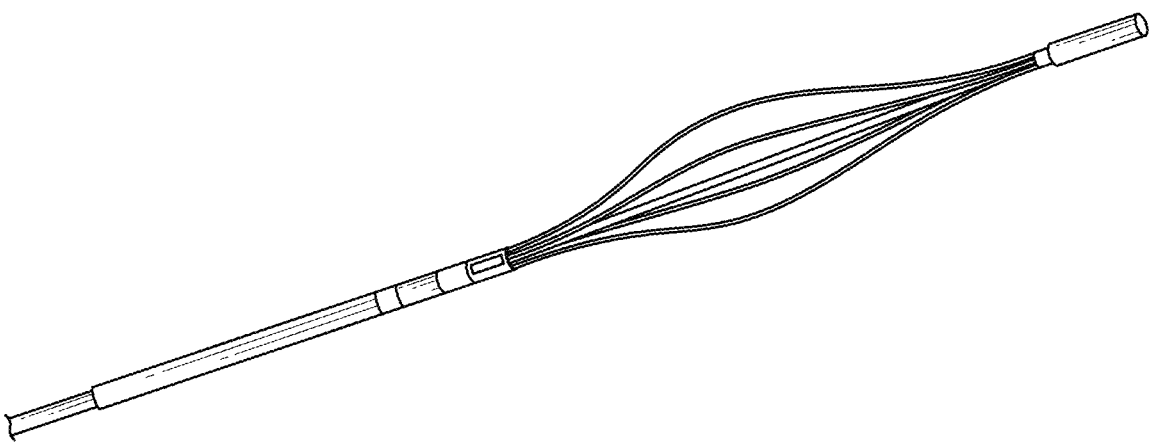
Figure 76C:
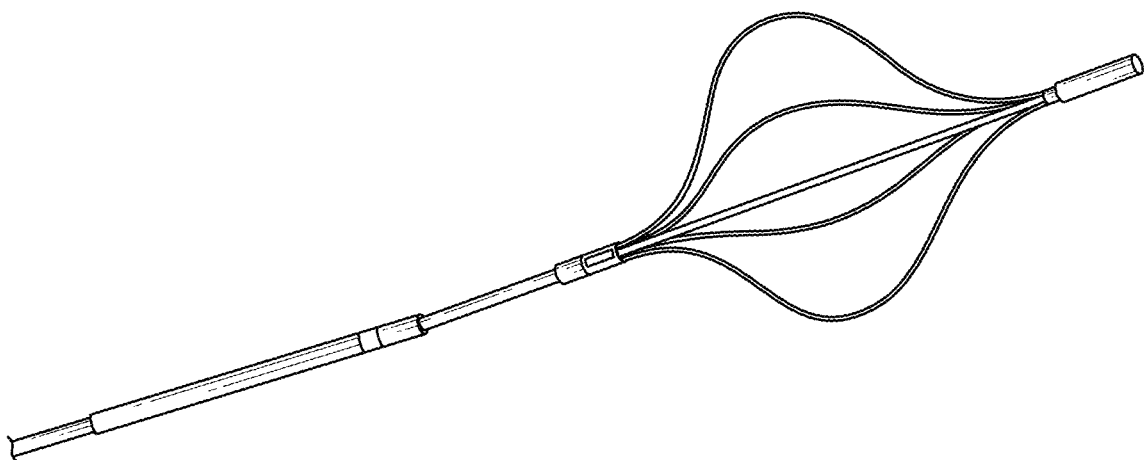

With reference to FIGS. 76A-76C, a retrieval tool in the form of a capture basket is provided. The retrieval tool completes the traversal pathway and externalizes the traversal wire to facilitate its exchange with tension elements. A snare catheter can be, for example, 6F. As illustrated in FIGS. 76A-76C. a retrieval tool is provided displaying the distal end region thereof, having a three-dimensional capture basket. The basket can have multiple configurations, such as those depicted in U.S. Pat. No. 10,433,962.

Figure 77:
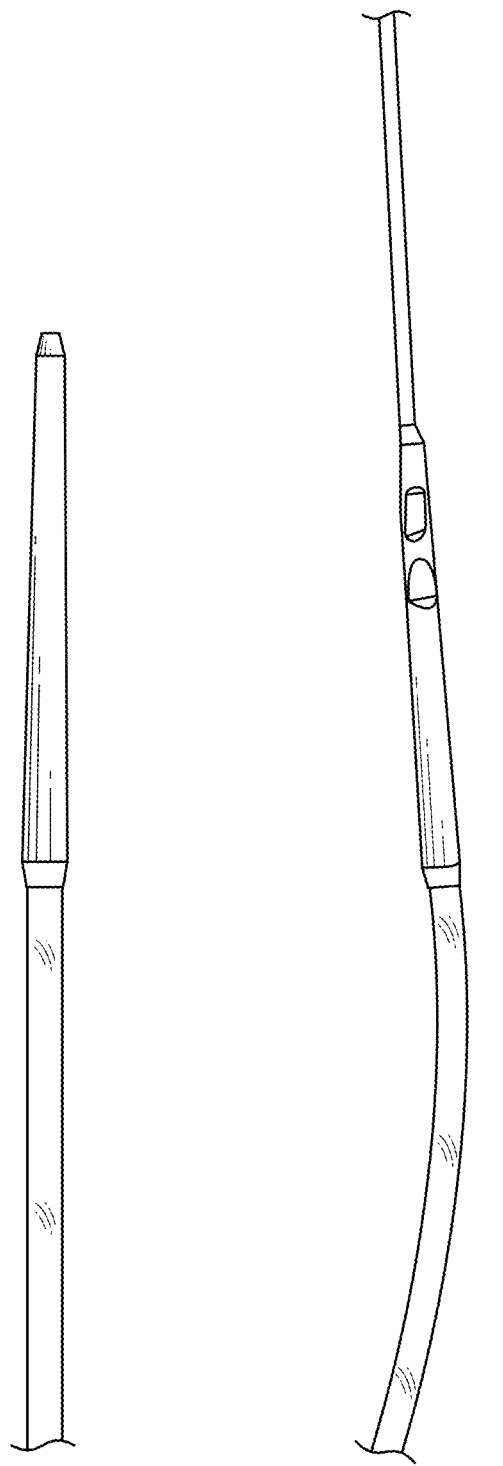

In order to facilitate the exchange of the traversal wire with the radiopaque tension elements, a secure connection should be formed between the two. FIG. 77 depicts an example of a crimp prototype for attaching a guidewire to a radiopaque suture, such as those depicted in U.S. Pat. No. 10,433,962.

Incorporating radiopaque tension elements can help maintain points of apposition of the device with the leaflets, as well as maintain the tension applied to the leaflets in order to reduce TR. It is possible to use a non-absorbable suture design with mechanical properties similar to commercially available sutures such as the Goretex CV-4. The tension elements can have a radiopaque core, such as including one or more of platinum, tungsten, tantalum, BaSO4 loaded Pebax, and the like for enhancing visibility under fluoroscopy and echocardiography layered under various outer layers, such as PET suture, to ensure that the tension element can withstand high tensile forces. Depending on the performance needs (often determined during acute animal studies), the tension element could take on one of a few different layered constructions. Additional radiopaque suture materials are disclosed in U.S. Pat. No. 10,433,962. Each suture (anterior, posterior, septal) can have a different color or other indicia such as radiopaque patterns to help physicians quickly determine which suture to select when adjusting the tension on each leaflet. The sutures can have a minimum length of 300 cm so they can easily be exchanged through the leaflet and externalized. FIG. 78. depicts a) 80% Tungsten Loaded 53D Tecoflex (0.014"). b) 99.99% Pure Platinum Wire (0.004"). c) 99.95% Pure Platinum Wire (0.006"). d) 99.95% Pure Platinum Wire (0.008"). e) 99.95% Pure Platinum Wire (0.010"). f) 90%/10% Platinum Iridium Wire (0.013").

Figure 79:
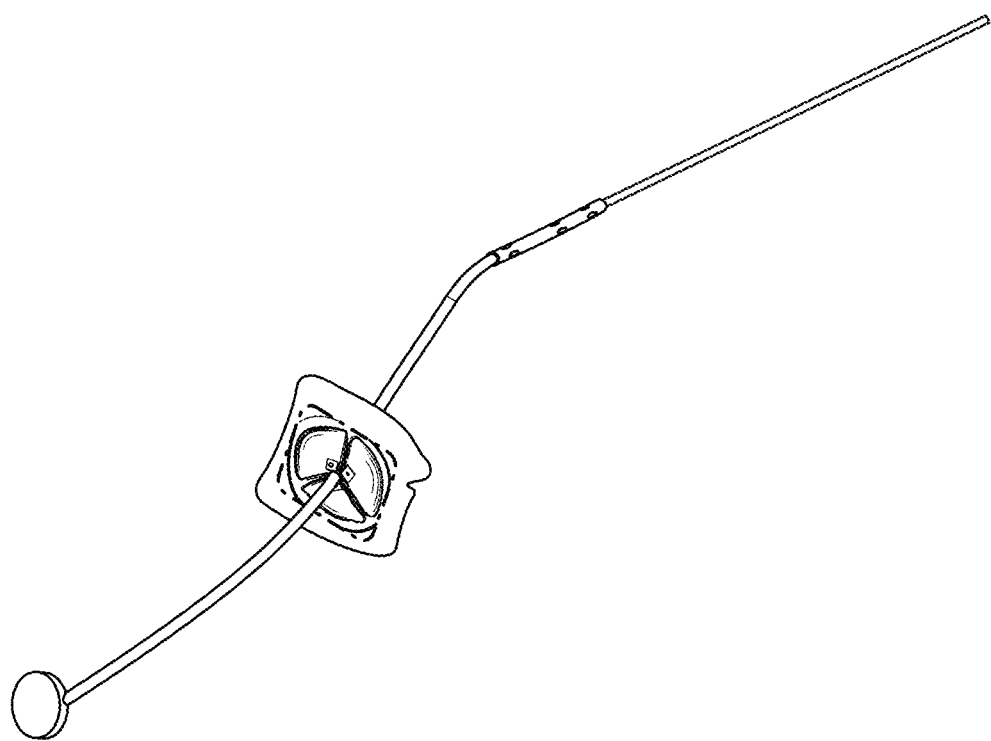

Force-distribution elements can be provided distribute the tension applied to the leaflets to avoid and resist tension element pull-through, such as a radiopaque pledge. The pledgets can be constructed by encapsulating a radiopaque material as described above between two pieces of medical fabric, such as PET. The pledgets can be around a size of about 4 mm L×3 mm W and have a folding design feature to ensure that they can be delivered through the multi-axial deflectable guide catheters. FIG. 79 depicts an illustrative radiopaque, pull-through resistant pledget.

Figure 80:
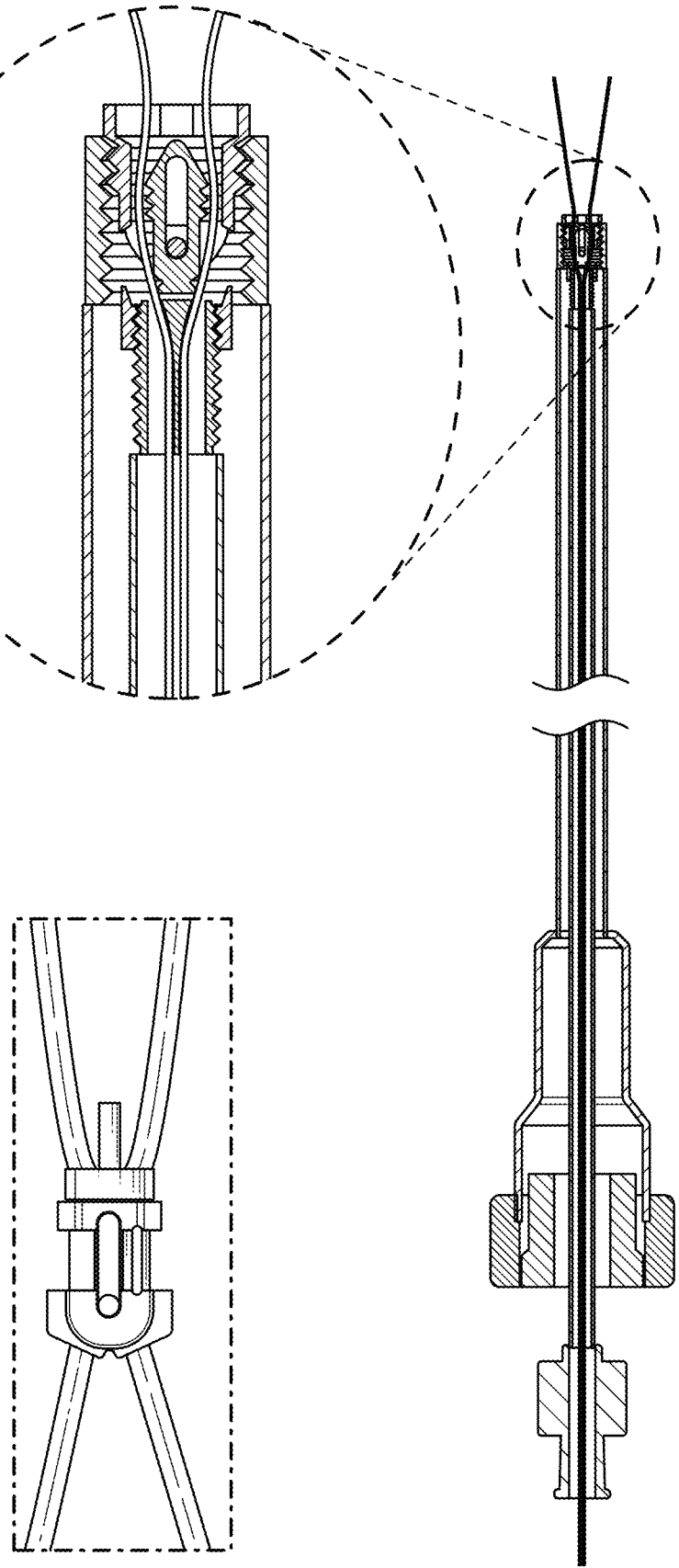
Figure 81:
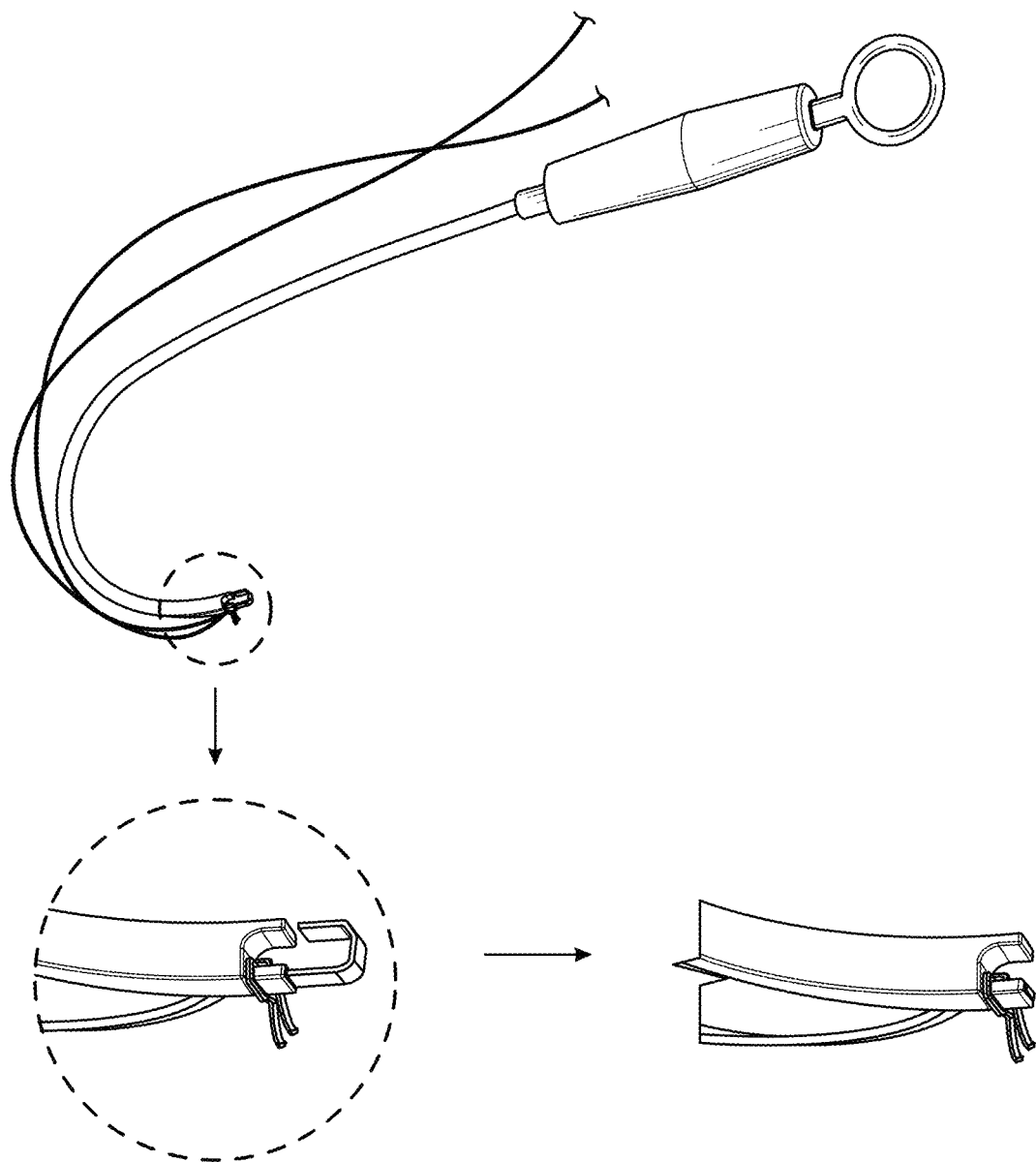

Adjustable transcatheter suture fixations can be provided such as those depicted in U.S. Pat. No. 10,433,962. Tension element fixation facilitates delivering secure and permanent fixation of the pledgeted sutures that are under tension. A transcatheter suture fixation system that allows for adjustability (e.g. fix and release multiple times without damaging sutures, withstand a range of tensile forces) can be used for this disclosed procedure so the physician can titrate the amount of tension being applied to the leaflets. This can allow for reversal or full retrieval after application, if necessary, which is an important safety feature. The fixation system can include, for example, a locking mechanism or a knot, among others. A lock can be made from a biocompatible, MRI-safe material, such as titanium, which can also provide visibility under fluoroscopy and echocardiography. The lock preferably easily fits through a low-profile introducer sheath. FIG. 80 depicts an illustrative suture lock to fixate two sutures. The lock can similarly be configured to accommodate three sutures. FIG. 81 depicts an illustrative "knot pusher" that can advance different half-hitch knots for straight distances up to a range of 30 cm.

Once the pledgeted sutures (tension and force-distribution elements) are deployed through the leaflets, under the appropriate tension, and are locked in place, the excess length of suture that are externalize out of the introducer sheath need to be cut and removed using, for example, suture cutters such as those depicted in U.S. Pat. No. 10,433,962. Preferably, the cutter is visible under fluoroscopy and echocardiography. The blade of the suture cutter can be corrosion resistant and have a level of hardness that allows all three sutures to be easily cut at the same time. The effective length cab be in a range of 120 cm to 140 cm, for example, in order to fit through the longest length guide catheters available on the market. FIG. 82 depicts an illustrative example of such a suture cutter that can be modified to be flexible and longer for transfemoral use and can be updated to cut three sutures.

Radiopaque and echogenic landmarks can be provided for real-time image guidance. Incorporating radiopaque and echogenic landmarks ensure that the physician can visualize the repair system during this procedure. For fluoroscopy, there can be landmarks, such as platinum iridium marker bands, in areas like the distal tips of delivery systems, at specific increments along the tension elements to allow the physician to estimate distance, and at the distal tips of the traversal tool and retrieval tool. Biocompatibility is important for these landmarks as the host or patient tends to be exposed to these materials both short-term and permanently. The inner shaft of the guide sheath can have a distinct echogenic feature at the tip for visibility under echocardiography. This can provide visualization during the leaflet traversal and puncture process. An echogenic feature, such as a segmented coil, can allow the physician to make contact between the inner shaft and the apical surface of the leaflet to facilitate leaflet traversal.

By providing at least three points of apposition for the tri-leaflets, it is ensured that the design for a transcatheter trileaflet tricuspid suture repair system can maintain at least one point of apposition with each leaflet, which can facilitate the reduction of TR. The disclosed systems and methods fulfill this by deploying a radiopaque pledgeted suture in each leaflet of the tricuspid valve. This is made possible by the purpose-built guide catheter that provides a 360° reach when navigating the valve. It will be appreciated that less points of apposition (e.g., two) can be used, and that three points is preferred. Likewise, these techniques can be used on other valve structures such as the mitral valve, pulmonary valve, and the like.

To provide insight as to how the designs detailed above can be used to treat TR, the procedure can have the following aspects. The procedure is preferably performed under anesthesia and mechanical ventilation. Fluoroscopy can be the main imaging modality for guiding or navigating during the procedure, while echocardiography will be used to determine the crossing site location on the tricuspid trileaflets and will be used to assess pre- and post-deployment TR.

Transvenous access can be established in the right femoral vein with a low-profile introducer sheath. Access to the right atrium can be achieved with Applicant's guide catheter through the inferior vena cava. The outer shaft of the guide catheter can be articulated and traversed through the tricuspid valve; the inner shaft can be articulated further back upwards toward the leaflets. FIGS. 83A-B depict a guide catheter traveling up an IVC to a right atrium and through the tricuspid valve. The inner shaft can be articulated towards the apical surface of the leaflets. The wire capture snare can be introduced through the sheath and navigated through the IVC to the right atrium. The wire capture basket can be deployed directly above the atrial surface of the trileaflet.

An electrified traversal wire can then be introduced and advanced through both shafts of the guide catheter until it apposes the apical side of one of the trileaflets. The traversal can be performed from the apical side to the atrial side of the leaflet to take advantage of the leaflets' natural, concave down shape; it is easier to traverse the leaflet in this fashion rather than from the atrial side down, which could cause slipping of the traversal wire.

Figure 84C:
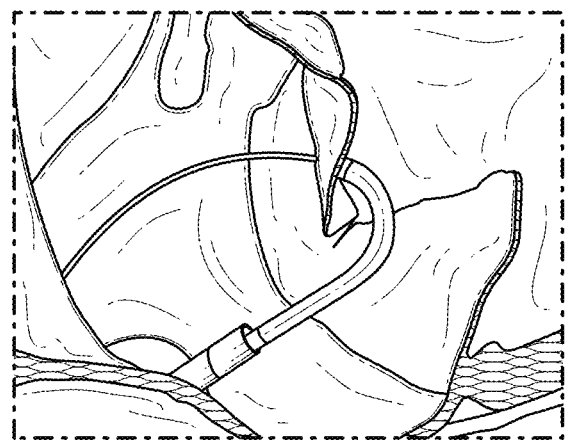
Figure 84B:
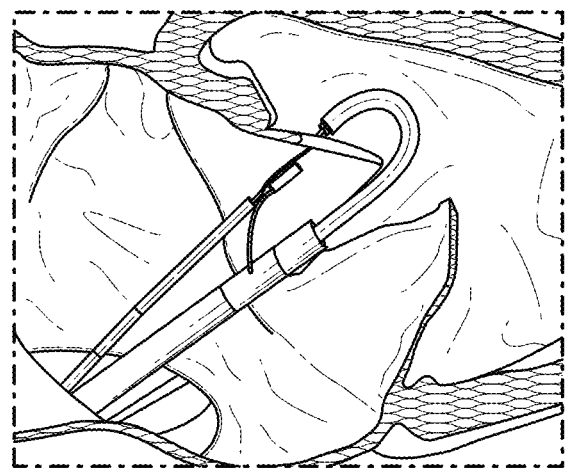
Figure 84A:
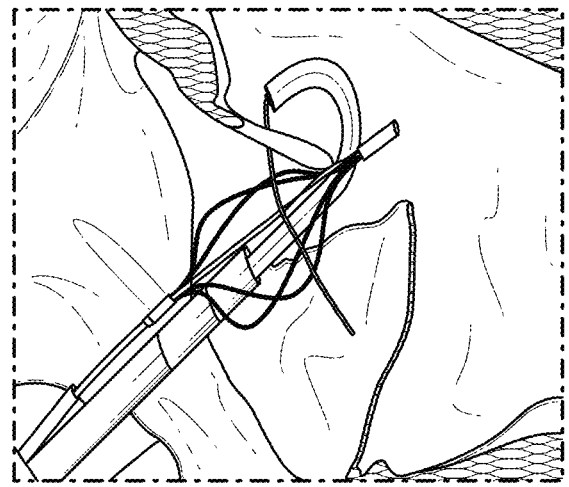

Once the crossing site is confirmed using echocardiography (e.g. a calcium free zone between 0.5 cm and 1 cm from the center edge of the leaflet), power can be delivered through the guidewire to the site to aid in traversing the leaflet tissue. The deployed wire capture basket can ensnare the traversal wire and externalize it down the IVC and out of the introducer sheath. FIGS. 84A-C depict a wire capture basket deployed with the traversal wire crossing through the basket (left), the traversal wire ensnared in the wire capture device (middle), and the traversal wire crossed through the leaflet with both ends externalized out of the introducer (right).

Figure 85:
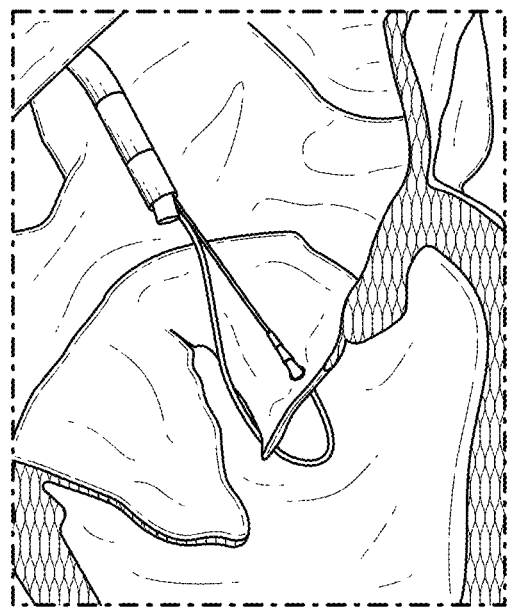
Figure 86:
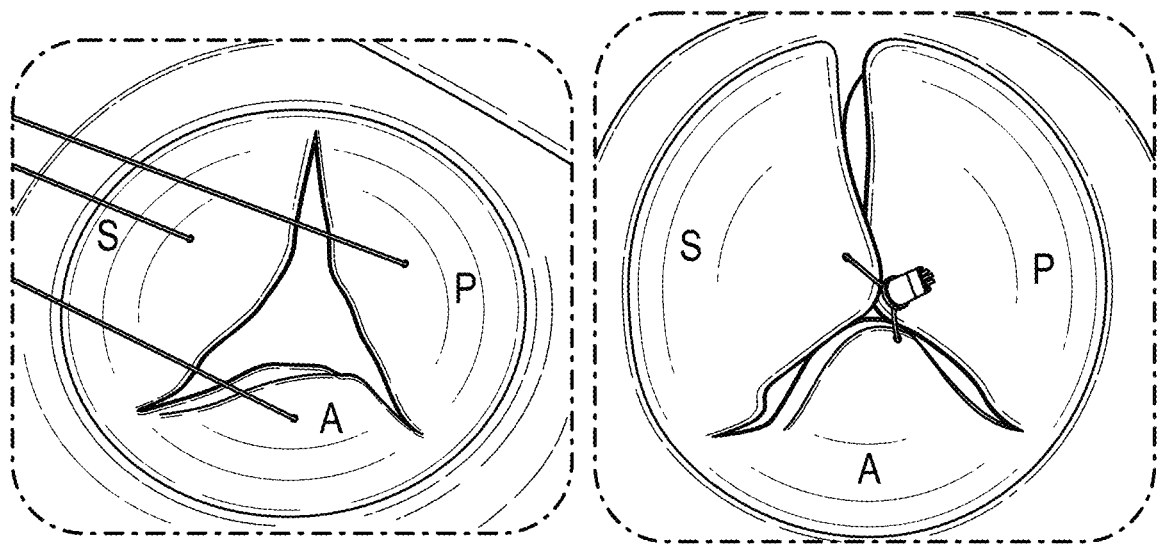

A suture loaded with a pledget can be exchanged with the traversal guidewire to be deployed through the trileaflet until the unpledgeted end of the suture is externalized. FIG. 85 illustrates delivery of pledgeted suture from the guide sheath. This whole process is repeated until each leaflet is tethered with a pledgeted suture. The sutures can be tensioned together, and can be fixated using a lock mechanism. Echocardiography can be used to assess the tension on the tricuspid tri-leaflets. Once the lock is placed, the sutures can be cut using a transcatheter suture cutter, which completes the implantation of the transcatheter trileaflet tricuspid suture repair system. FIGS. 86 (and 94) depicts tricuspid tri-leaflets tensioned with pledgeted sutures (left) and locked into place (right) reducing TR.

Figure 87:
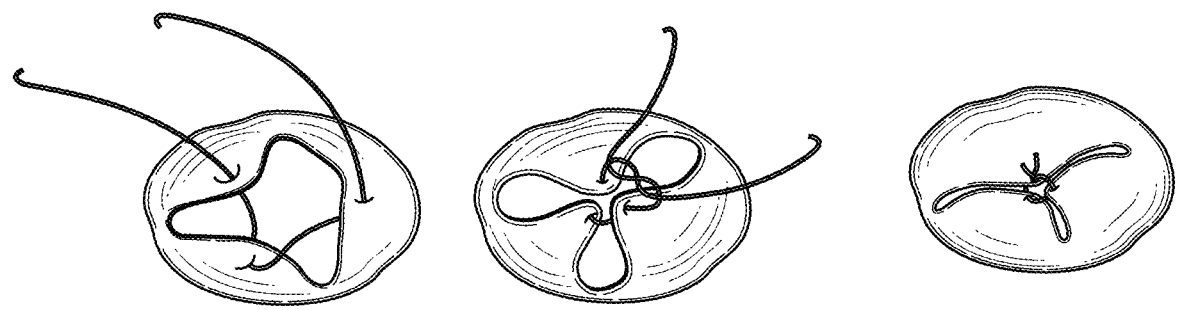
Figure 88:
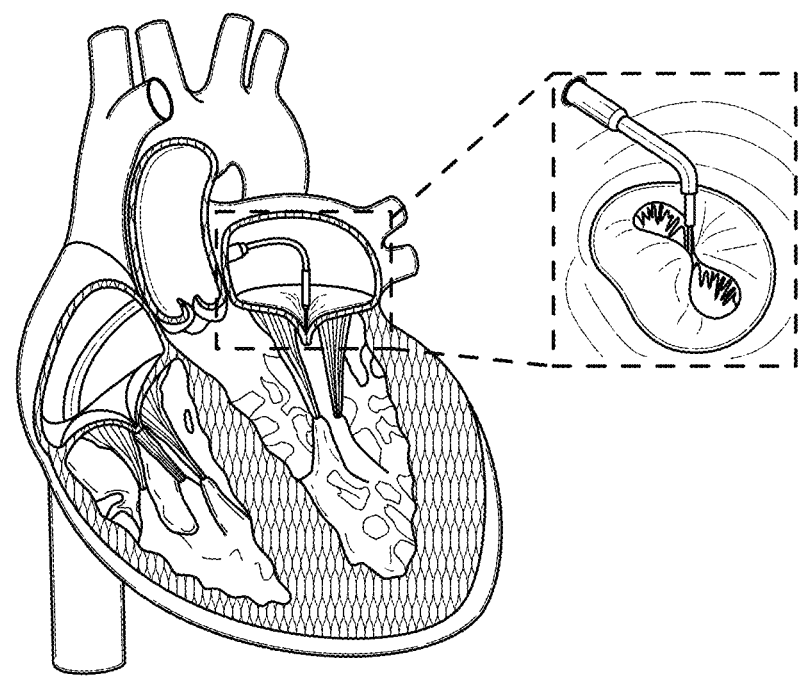
Figure 90:
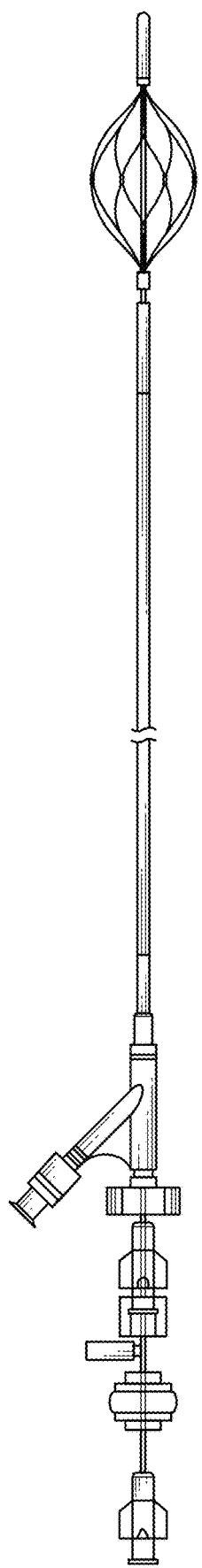
Figure 91:
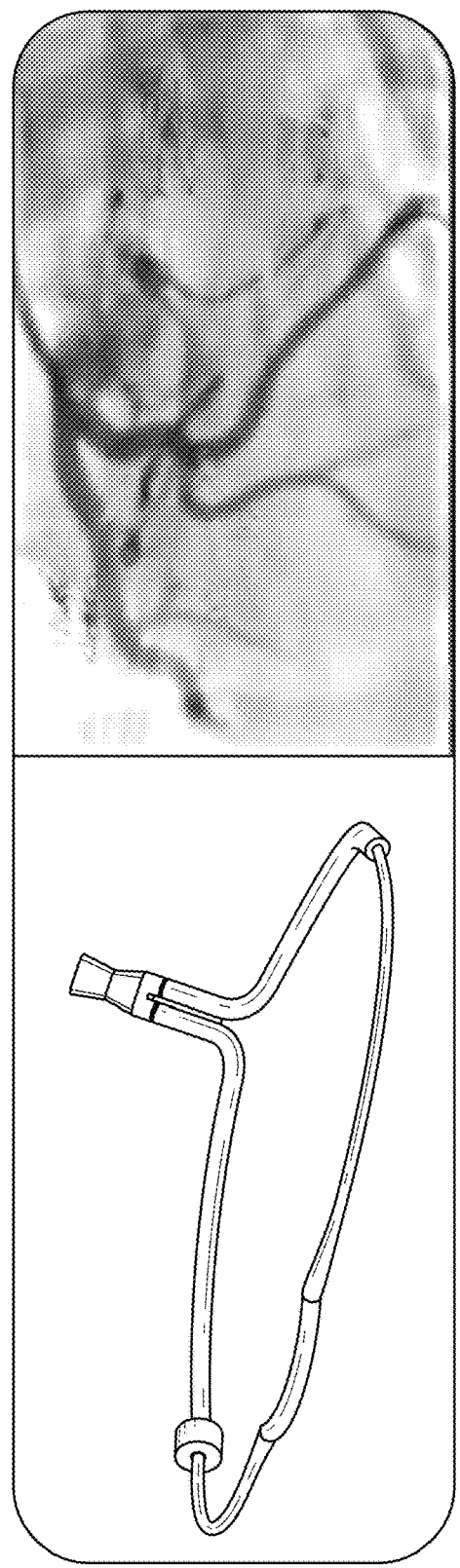
Figure 92:
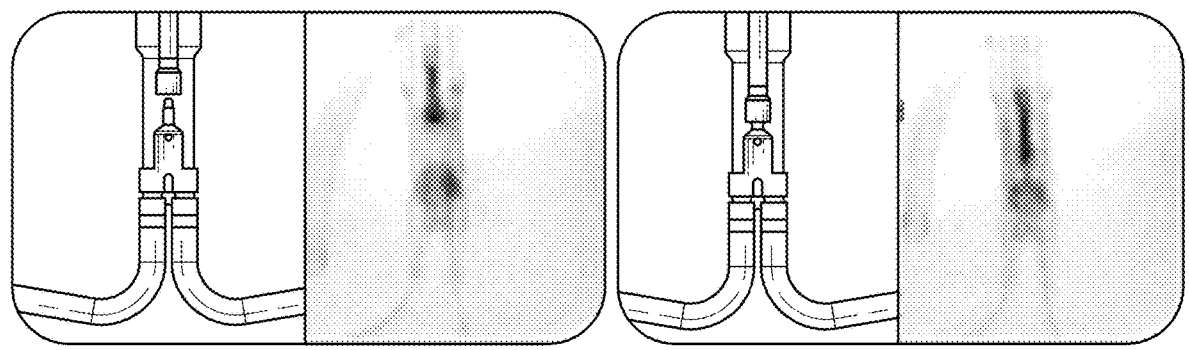
Figure 93:
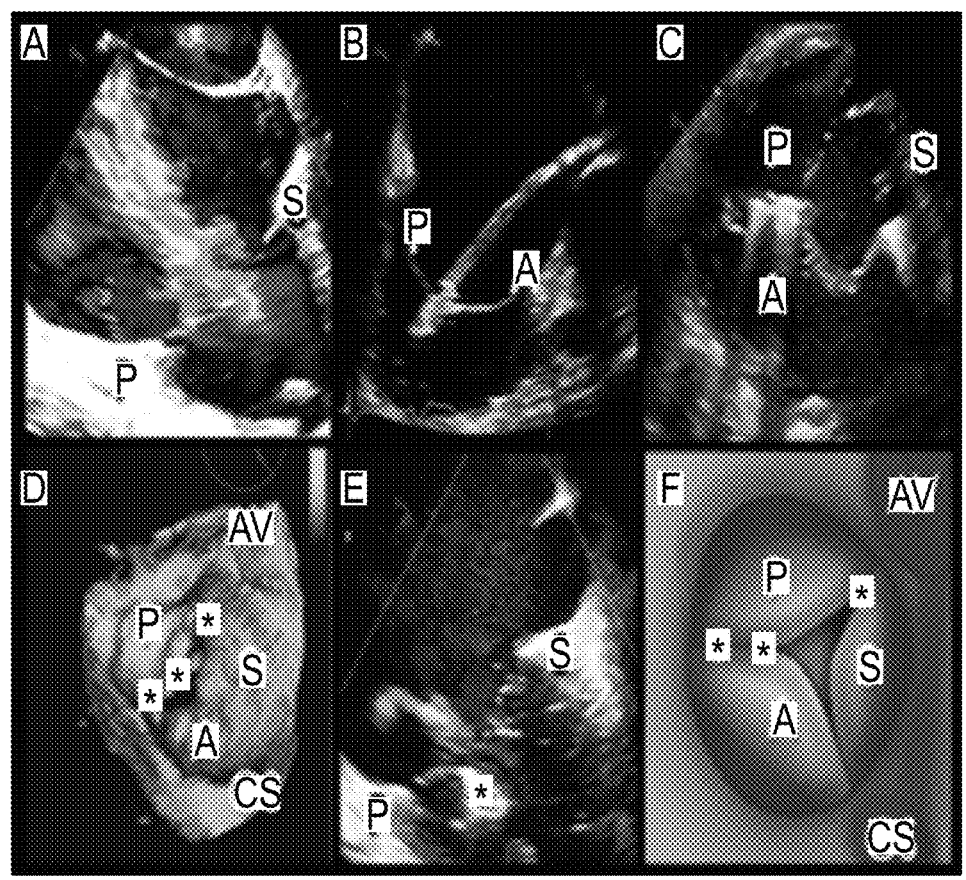

Previous relevant techniques include the Alfieri "clover technique" and PASTA (Pledget-Assisted Suture Tricuspid Annuloplasty). The "clover technique" is a surgical repair typically performed on a regurgitant tricuspid valve that sutures together the middle point of the free edges of the leaflets to create a "clover" shape. FIG. 87 depicts the "clover technique" (suturing together the middle point of the free edges of the tricuspid leaflets) for the treatment of TR. FIG. 88 depicts a MitraClip (Abbott Vascular, Santa Clara, CA), which is a percutaneous mitral valve repair using anterior-posterior edge-to-edge direct leaflet approximation.

FIG. 89 depicts an E. PASTA overview viewed from the ventricles: (A) A dilated tricuspid valve annulus, and (B) a double orifice valve created by PASTA pledgeted sutures between the postero-septal and mid-anterior annulus. MRI images before (C) and after (D) PASTA demonstrating reduced annular dimension from 10.4 cm 2 to 2.9 cm 2. (E) Necropsy 30 days after PASTA, viewed from the atrium. S 5 septum; A 5 anterior annulus; P 5 posterior leaflet.

Devices were designed and built to allow transcatheter mitral repair through cerclage annuloplasty procedure. Applicant's innovations from this project include, for example, a guidewire capture snare that uses a three-dimensional capture basket to snare and externalize various sized guidewires with ease (FIG. 90), a radiopaque implant tether that is tensioned and secured extrinsically around the mitral valve with a novel locking mechanism (FIG. 91), a lock, and delivery system, that can fix multiple sutures under high tension and is adjustable and removable (FIG. 92), and a percutaneous suture cutter that can cut implanted, radiopaque sutures at various lengths (FIG. 82). The devices can be used as set forth herein to accomplish an edge-to-edge repair of tricuspid regurgitation (TR) (FIG. 93; wherein A, TR before clip implantation. B, Grasp of the anterior and posterior tricuspid valve leaflets. C, Transgastric view during diastole showing 3 clips in place and a bicuspidized tricuspid valve. D, 3-dimensional (3D) en-face view after Clip implantation. E, Residual TR. F, Sketch of the procedural strategy. A indicates anterior tricuspid valve leaflet; AV, aortic valve; CS, coronary sinus; P, posterior leaflet; and S, septal leaflet. *Clip device).

The devices and methods disclosed herein can be used for other procedures in an as-is condition, or can be modified as needed to suit the particular procedure. In view of the many possible embodiments to which the principles of this disclosure may be applied, it should be recognized that the illustrated embodiments are only preferred examples of the disclosure and should not be taken as limiting the scope of the disclosure. Each and every patent and patent application referenced herein is expressly incorporated by reference herein in its entirety for any purpose whatsoever.

What is claimed is:

1. A catheter having a proximal end, a distal end, and defining a longitudinal axis, the catheter comprising:
   a first elongate member having a proximal end, a distal end and defining a lumen at least partially along a length of the first elongate member, the first elongate member having a collapsible basket mounted thereon having an open distally facing end;
   a tether operably coupled to and at least partially surrounding a perimeter of the open distally facing end of the collapsible basket, the tether further extending proximally parallel to the longitudinal axis toward the proximal end of the catheter, wherein the open distally facing end of the collapsible basket is configured to be collapsed by applying tension to the tether along a proximal direction;
   a second elongate member slidably disposed within the lumen of the first elongate member, the second elongate member having a proximal end and a distal end, wherein the distal end of the second elongate member can be advanced distally beyond the distal end of the first elongate member;
   a cutting snare loop operably coupled to the distal end of the second elongate member, wherein:
   the cutting snare loop is configured to be laterally collapsed and withdrawn proximally into a distal end of the lumen of the first elongate member by withdrawing the second elongate member along the proximal direction into the lumen of the first elongate member;
   the cutting snare loop is configured to be deployed distally out of the distal end of the lumen of the first elongate member by advancing the second elongate member distally;
   the cutting snare loop is configured to self-orient into a first plane that is oriented transversely with respect to the longitudinal axis of the catheter when deployed distally outwardly from the lumen of the first elongate member, and further wherein a user can use the basket to at least partially surround an object attached to a tissue mass, collapse the basket around the object by applying tension to the actuator, and then sever the tissue mass by cutting through the tissue mass with the deployable cutting snare loop.

2. The catheter of claim 1, wherein cutting by way of the cutting snare loop is accomplished at least in part by withdrawing the cutting snare loop proximally into the lumen of the first elongate member.

3. The catheter of claim 1, wherein the collapsible basket is formed from a laser cut hypotube formed into a stent-like pattern defined by zig-zag rows of struts.

4. The catheter of claim 1, wherein a proximal end of the collapsible basket is fastened to the elongate member by a radiopaque marker band and the first elongate member further includes a second radiopaque marker at a distal end of the first elongate member.

5. The catheter of claim 1, further comprising a tissue grasper, wherein the tissue grasper can be advanced distally out of the collapsible basket to grasp tissue.

6. The catheter of claim 5, wherein the the tissue grasper includes a plurality of radially outwardly biased gripping arms, wherein the radially outwardly biased gripping arms collapse radially inwardly when the tissue grasper is advanced along a proximal direction with respect to the collapsible basket.

7. The catheter of claim 6, wherein each said gripping arm is formed from a planar strip of material that terminates in a radially inwardly converging distal tip and includes proximal end affixed to a distal end of an inner elongate member, and a preformed bend that bends the arm radially outwardly, and then bends radially inwardly as the arm approaches a tapered distal tip.

8. The catheter of claim 1, wherein the cutting snare loop is coupled to an electrical power source to electrify the cutting snare loop.

9. The catheter of claim 1, wherein the perimeter of the open distally facing end of the collapsible basket is disposed in a second plane that is oriented transversely with respect to the longitudinal axis of the catheter.

10. The catheter of claim 9, wherein the cutting snare loop is configured to align axially with the open distally facing end of the collapsible basket when the cutting snare loop is deployed to permit an object to be removed from a patient's anatomy to be received through the cutting snare loop and through the open distally facing end of the collapsible basket at the same time.

11. A method of removing a mitral clip coupled to two native mitral valve leaflets while a patient's heart is beating, comprising:
   providing a catheter according to claim 1;
   deploying the cutting snare loop;
   sliding the cutting snare loop around the mitral clip;

advancing the cutting snare loop along the mitral clip to a location where the mitral clip it adjoins native valve tissue;

at least partially surrounding the mitral clip with the collapsible basket;

collapsing the collapsible basket around the mitral clip to grip the mitral clip by applying tension to the tether;

severing the mitral clip from the native valve tissue by cutting the native valve tissue with the deployable cutting snare loop; and removing the mitral clip from the patient.

12. The method of claim 11, wherein the procedure is performed percutaneously.

13. The method of claim 11, wherein the procedure is performed apically.

14. A method of using the catheter to remove a mitral clip, comprising:

providing a catheter according to claim 5;

advancing a distal end of the catheter to a mitral clip attached to a pair of native mitral valve leaflets;

distally extending the tissue grasper to surround the mitral clip; and grasping the mitral clip with the tissue grasper to hold the mitral clip in place.

* * * * *